US012605437B2

(12) United States Patent (10) Patent No.: US 12,605,437 B2
Wressnigg et al. (45) **Date of Patent: *Apr. 21, 2026**

(54) SINGLE SHOT CHIKUNGUNYA VIRUS VACCINE

(71) Applicant: Valneva SE, Nantes (FR)

(72) Inventors: Nina Wressnigg, Gießhübl (AT); Romana Hochreiter, Vienna (AT)

(73) Assignee: Valneva SE, Nantes (FR)

( * ) Notice: Subject to any disclaimer, the term of this patent is extended or adjusted under 35 U.S.C. 154(b) by 1079 days.

This patent is subject to a terminal disclaimer.

(21) Appl. No.: 17/632,946

(22) PCT Filed: Aug. 10, 2020

(86) PCT No.: PCT/EP2020/072436
§ 371 (c)(1),
(2) Date: Feb. 4, 2022

(87) PCT Pub. No.: WO2021/028407
PCT Pub. Date: Feb. 18, 2021

(65) Prior Publication Data
US 2022/0313810 A1 Oct. 6, 2022

(30) Foreign Application Priority Data

Aug. 9, 2019 (EP) ..................................... 19191030
Feb. 20, 2020 (EP) ..................................... 20158557

(51) Int. Cl.
| A61K 39/12 | (2006.01) |
| A61P 31/14 | (2006.01) |
| A61K 39/00 | (2006.01) |

(52) U.S. Cl.
CPC .............. *A61K 39/12* (2013.01); *A61P 31/14* (2018.01); *A61K 2039/5254* (2013.01); *C12N 2770/36134* (2013.01)

(58) Field of Classification Search
None
See application file for complete search history.

(56) References Cited

U.S. PATENT DOCUMENTS

2017/0014502 A1 1/2017 Sumathy et al.

FOREIGN PATENT DOCUMENTS

| WO | WO 1998/013065 A1 | 4/1998 |
| WO | WO 2017/109223 A1 | 6/2017 |
| WO | WO 2017/109224 A1 | 6/2017 |
| WO | WO 2017/172643 A1 | 10/2017 |
| WO | WO 2019/057793 A1 | 3/2019 |

OTHER PUBLICATIONS

[No Author Listed], Structural polyprotein. Chikungunya virus (CHIKV). UNIPROT Accession No. D2KBQ0. Feb. 9, 2010. Accessible at https://www.uniprot.org/uniprotkb/D2KBQ0/entry. 3 pages.
Hallengärd et al., Novel attenuated Chikungunya vaccine candidates elicit protective immunity in C57BL/6 mice. J Virol. Mar. 2014;88(5):2858-66. doi: 10.1128/JVI.03453-13. Epub Dec. 26, 2013.
Milligan et al., Defining a correlate of protection for chikungunya virus vaccines. Vaccine. Nov. 28, 2019;37(50):7427-7436. doi: 10.1016/j.vaccine.2018.10.033. Epub Nov. 15, 2018.
Roques et al., Effectiveness of CHIKV vaccine VLA1553 demonstrated by passive transfer of human sera. JCI Insight. Jul. 22, 2022;7(14):e160173. doi: 10.1172/jci.insight.160173. 16 pages.
Zheng et al., Genetic analysis of chikungunya viruses imported to mainland China in 2008. Virol J. Jan. 18, 2010;7:8. doi: 10.1186/1743-422X-7-8. 6 pages.
PCT/EP2020/072435, Dec. 3, 2020, International Search Report and Written Opinion.
PCT/EP2020/072435, Feb. 17, 2022, International Preliminary Report on Patentability.
PCT/EP2020/072436, Dec. 3, 2020, International Search Report and Written Opinion.
PCT/EP2020/072436, Feb. 17, 2022, International Preliminary Report on Patentability.
[No Author Listed], Declaration of Helsinki. Bulletin of the World Health Organization. 2001;79(4):373-4.
[No Author Listed], International Conference on Harmonisation (ICH) of Technical Requirements for Registration of Pharmaceuticals for Human Use / Guideline for Good Clinical Practice. 1996. 59 pages.
[No Author Listed], Number of reported cases of chikungunya fever in the Americas by country or territory. World Health Organization. 2013-2016. Accessible at http://www.paho.org/hq/index.php?option=com_topics. 1 page.
[No Author Listed], Valneva Reports Positive 24-Month Antibody Persistence Data for its Single-Shot Chikungunya Vaccine IXCHIQ®. Valneva SE. Dec. 4, 2023. 5 pages.
Ahola et al., Therapeutics and vaccines against chikungunya virus. Vector Borne Zoonotic Dis. Apr. 2015;15(4):250-7. doi: 10.1089/vbz.2014.1681. Erratum in: Vector Borne Zoonotic Dis. Nov. 2015;15(11):712. Courderc, Therese [Corrected to Couderc, Therese].
Bandeira et al., Prolonged shedding of Chikungunya virus in semen and urine: A new perspective for diagnosis and implications for transmission. IDCases. Nov. 4, 2016;6:100-103. doi: 10.1016/j.idcr.2016.10.007.
Broeckel et al., Therapeutic administration of a recombinant human monoclonal antibody reduces the severity of chikungunya virus disease in rhesus macaques. PLoS Negl Trop Dis. Jun. 19, 2017;11(6):e0005637. doi: 10.1371/journal.pntd.0005637.
Chang et al., Effect of sorbitol and residual moisture on the stability of lyophilized antibodies: Implications for the mechanism of protein stabilization in the solid state. J Pharm Sci. Jul. 2005;94(7):1445-55. doi: 10.1002/jps.20363.

(Continued)

*Primary Examiner* — Stacy B Chen
(74) *Attorney, Agent, or Firm* — Wolf, Greenfield & Sacks, P.C.

(57) ABSTRACT

The present invention relates to a single-shot live attenuated vaccine against Chikungunya virus which is well-tolerated and induces long-lasting protective immunity in adult human subjects.

18 Claims, 26 Drawing Sheets

Specification includes a Sequence Listing.

(56)         References Cited

OTHER PUBLICATIONS

Chu et al., Deciphering the protective role of adaptive immunity to CHIKV/IRES a novel candidate vaccine against Chikungunya in the A129 mouse model. Vaccine. Jul. 18, 2013;31(33):3353-60. doi: 10.1016/j.vaccine.2013.05.059. Epub May 29, 2013. Author Manuscript. 19 pages.

Couderc et al., Prophylaxis and therapy for Chikungunya virus infection. J Infect Dis. Aug. 15, 2009;200(4):516-23. doi: 10.1086/600381.

Galatas et al., Long-Lasting Immune Protection and Other Epidemiological Findings after Chikungunya Emergence in a Cambodian Rural Community, Apr. 2012. PLoS Negl Trop Dis. Jan. 11, 2016;10(1):e0004281. doi: 10.1371/journal.pntd.0004281.

Gérardin et al., Chikungunya virus-associated encephalitis: A cohort study on La Réunion Island, 2005-2009. Neurology. Jan. 5, 2016;86(1):94-102. doi: 10.1212/WNL.0000000000002234. Epub Nov. 25, 2015.

Kam et al., Early neutralizing IgG response to Chikungunya virus in infected patients targets a dominant linear epitope on the E2 glycoprotein. EMBO Mol Med. Apr. 2012;4(4):330-43. doi: 10.1002/emmm.201200213. Epub Mar. 5, 2012.

Linn et al., Alphavirus-specific cytotoxic T lymphocytes recognize a cross-reactive epitope from the capsid protein and can eliminate virus from persistently infected macrophages. J Virol. Jun. 1998;72(6):5146-53. doi: 10.1128/JVI.72.6.5146-5153.1998.

Lum et al., An essential role of antibodies in the control of Chikungunya virus infection. J Immunol. Jun. 15, 2013;190(12):6295-302. doi: 10.4049/jimmunol.1300304. Epub May 13, 2013.

Musso et al., Detection of chikungunya virus in saliva and urine. Virol J. Jun. 16, 2016;13:102. doi: 10.1186/s12985-016-0556-9. Erratum in: Virol J. 2016;13(1):120.

Muturi-Kioi et al., Neutropenia as an Adverse Event following Vaccination: Results from Randomized Clinical Trials in Healthy Adults and Systematic Review. PLoS One. Aug. 4, 2016;11(8):e0157385. doi: 10.1371/journal.pone.0157385.

Nitatpattana et al., Long-term persistence of Chikungunya virus neutralizing antibodies in human populations of North Eastern Thailand. Virol J. Oct. 21, 2014;11:183. doi: 10.1186/1743-422X-11-183.

Pal et al., Development of a highly protective combination monoclonal antibody therapy against Chikungunya virus. PLoS Pathog. 2013;9(4):e1003312. doi: 10.1371/journal.ppat.1003312. Epub Apr. 18, 2013. 16 pages.

Panning et al., Chikungunya fever in travelers returning to Europe from the Indian Ocean region, 2006. Emerg Infect Dis. Mar. 2008;14(3):416-22. doi: 10.3201/eid1403.070906.

Pastorino et al., Development of a TaqMan RT-PCR assay without RNA extraction step for the detection and quantification of African Chikungunya viruses. J Virol Methods. Mar. 2005;124(1-2):65-71. doi: 10.1016/j.jviromet.2004.11.002. Epub Dec. 15, 2004.

Reed et al., A simple method of estimating fifty percent endpoints. Am J Hygiene. 1938;27:493-497.

Reisinger et al., Immunogenicity, safety, and tolerability of the measles-vectored chikungunya virus vaccine MV-CHIK: a double-blind, randomised, placebo-controlled and active-controlled phase 2 trial. Lancet. Dec. 22, 2019;392(10165):2718-2727. doi: 10.1016/S0140-6736(18)32488-7. Epub Nov. 5, 2018.

Roques et al., Attenuated and vectored vaccines protect nonhuman primates against Chikungunya virus. JCI Insight. Mar. 23, 2017;2(6):e83527. doi: 10.1172/jci.insight.83527.

Schwartz et al., Formulation and Stability of a Chikungunya Virus-Like Particle (ChikV VLP) Based Vaccine. From Vaccine Technology IV. University College London, UK. Wyeth Vaccine Research Eds, ECI Symposium Series. Accessible at http://dc.engconfintl.org/vaccine_jv/17.2012. 22 pages.

Vega-Rúa et al., Chikungunya virus transmission potential by local Aedes mosquitoes in the Americas and Europe. PLoS Negl Trop Dis. May 20, 2015;9(5):e0003780. doi: 10.1371/journal.pntd.0003780. 18 pages.

Weaver, Arrival of chikungunya virus in the new world: prospects for spread and impact on public health. PLoS Negl Trop Dis. Jun. 26, 2014;8(6):e2921. doi: 10.1371/journal.pntd.0002921. 4 pages.

Wressnigg et al., Single-shot live-attenuated chikungunya vaccine in healthy adults: a phase 1, randomised controlled trial. Lancet Infect Dis. Oct. 2020;20(10):1193-1203. doi: 10.1016/S1473-3099(20)30238-3. Epub Jun. 1, 2020.

Xie et al., Mechanism of the stabilization of ribonuclease A by sorbitol: preferential hydration is greater for the denatured then for the native protein. Protein Sci. Jan. 1997;6(1):211-21. doi: 10.1002/pro.5560060123.

Yoon et al., High rate of subclinical chikungunya virus infection and association of neutralizing antibody with protection in a prospective cohort in the Philippines. PLoS Negl Trop Dis. May 7, 2015;9(5):e0003764. doi: 10.1371/journal.pntd.0003764. 14 pages.

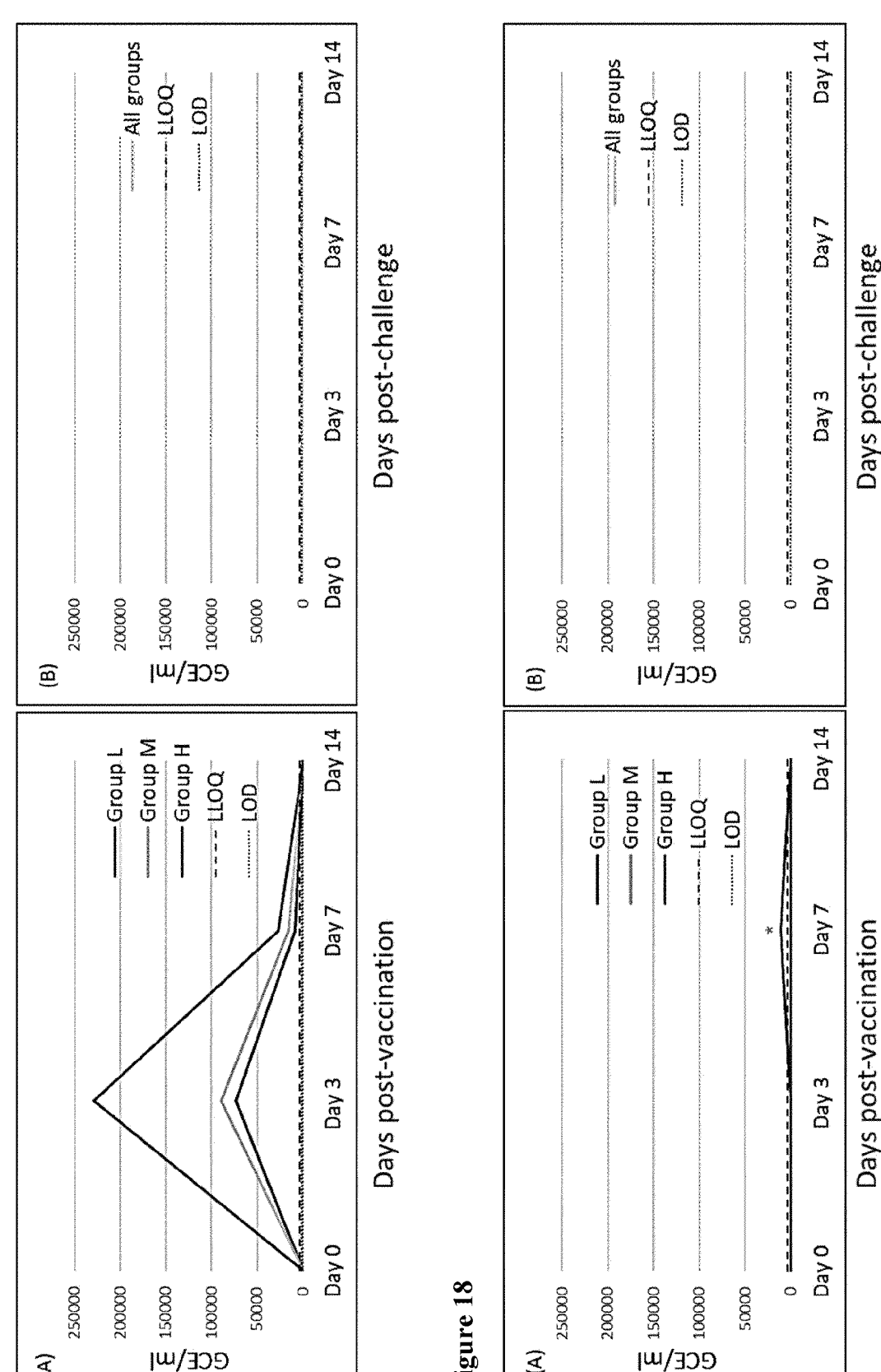

Figure 19
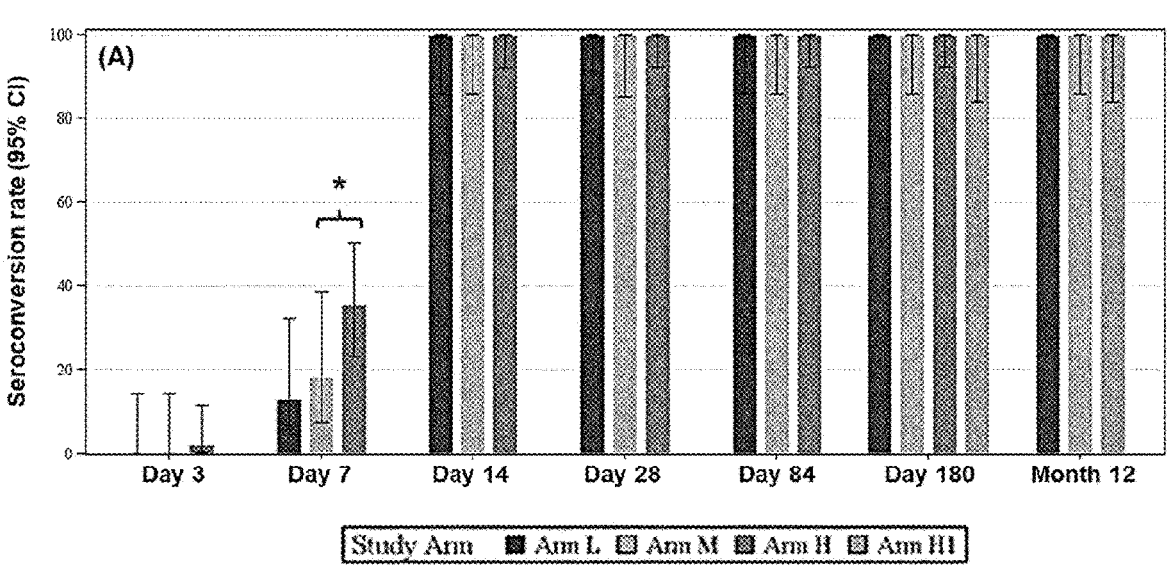
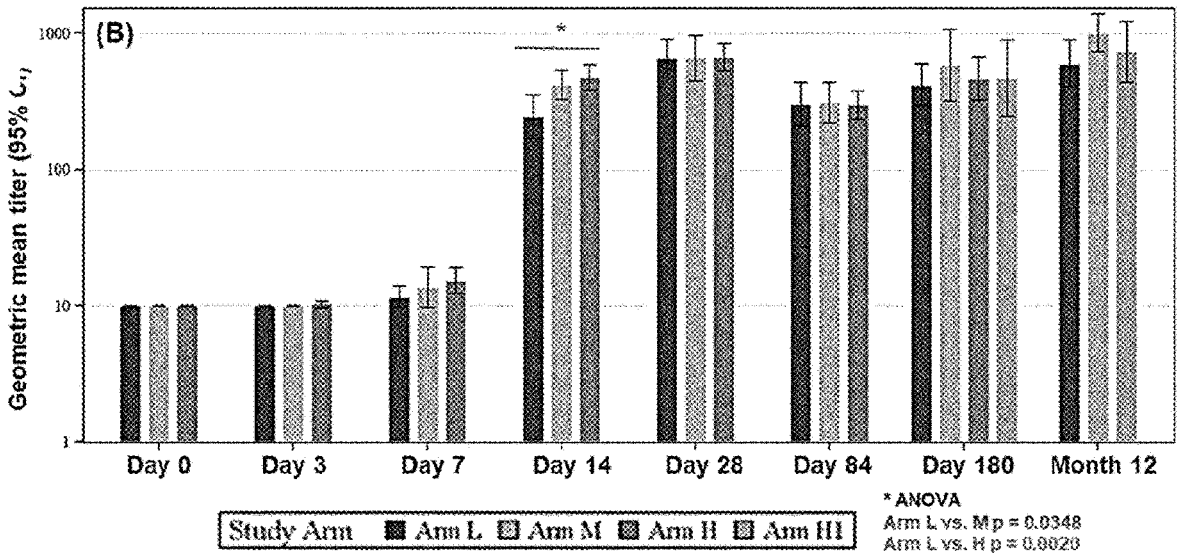

Figure 20
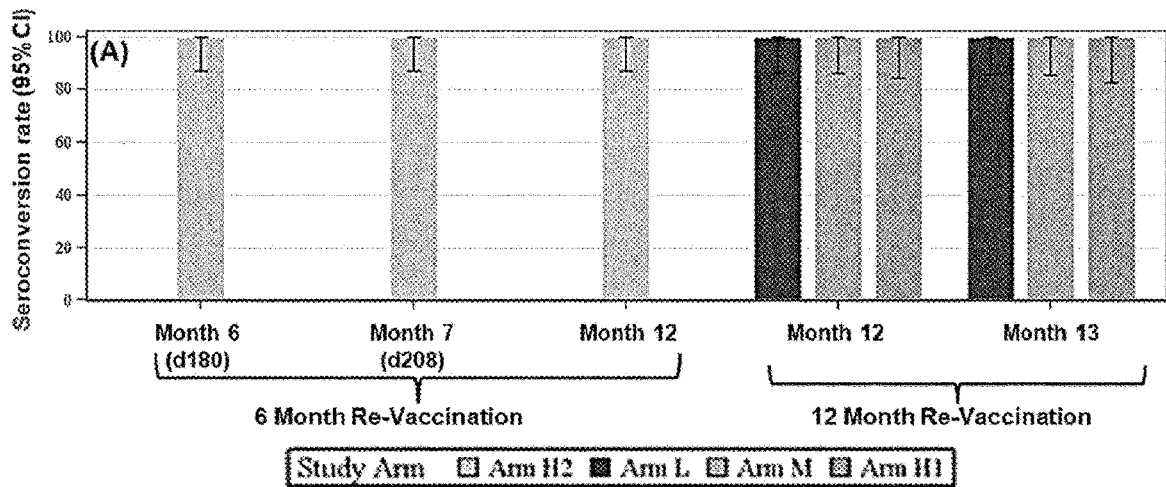
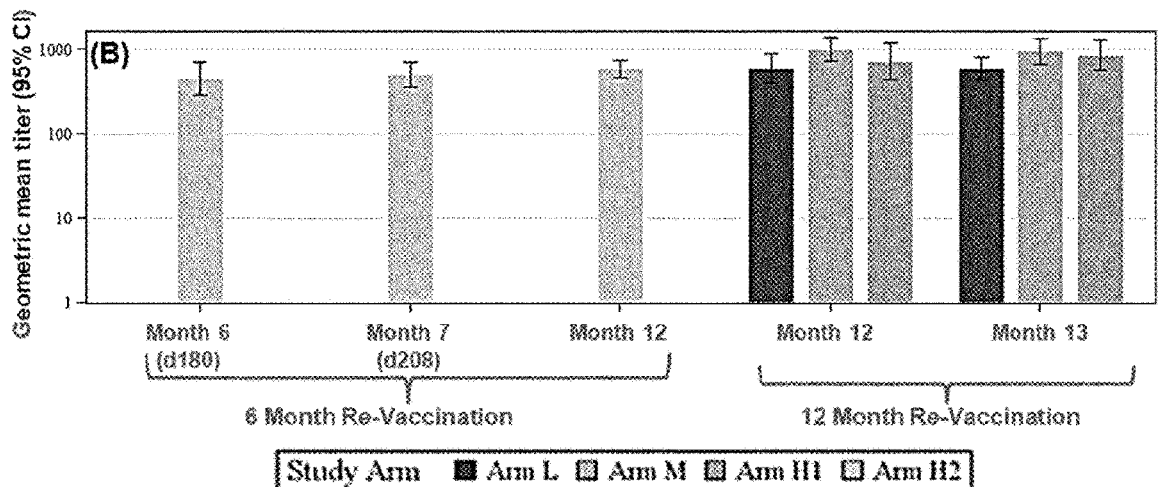

Figure 21
(A) 1:40
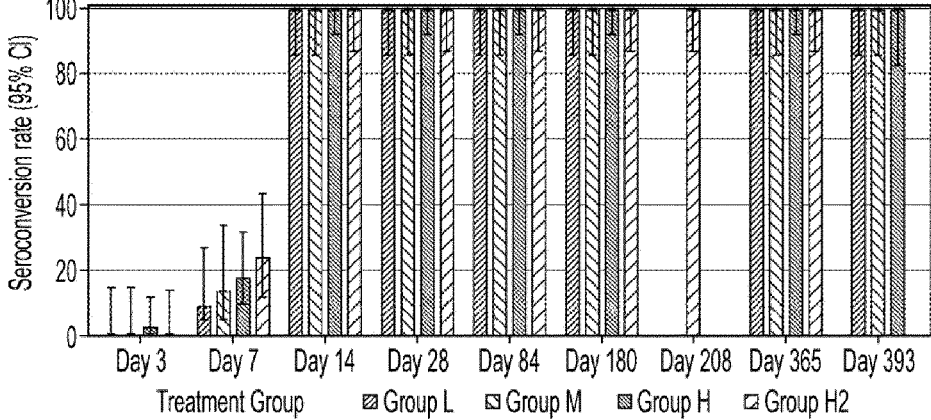
(B) 1:80
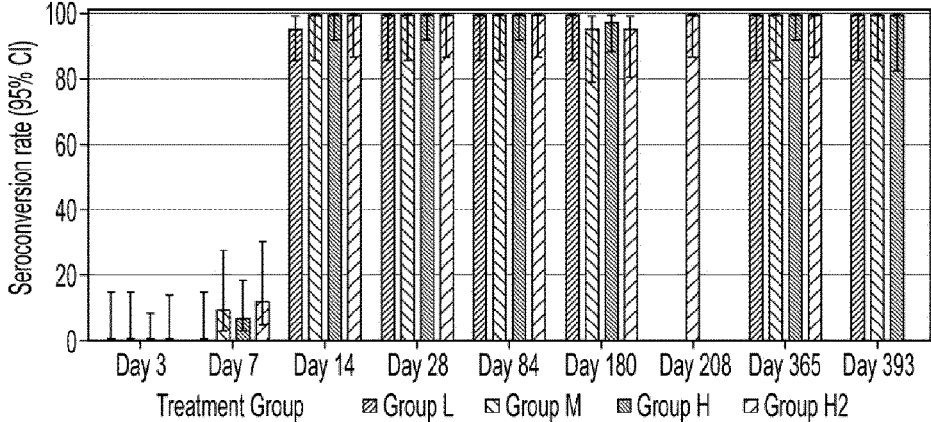
(C) 1:160
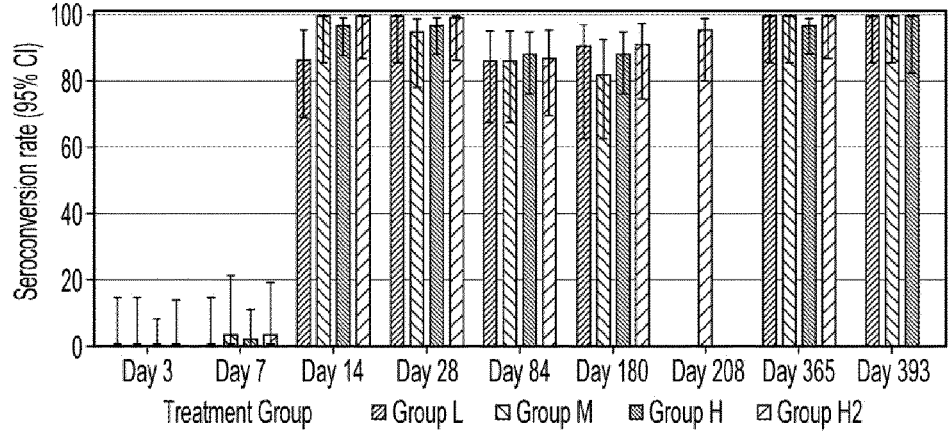

(A)

(B)

Figure 23
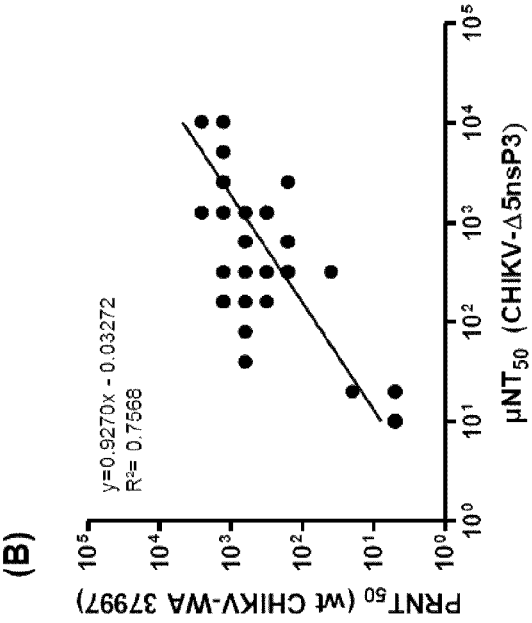
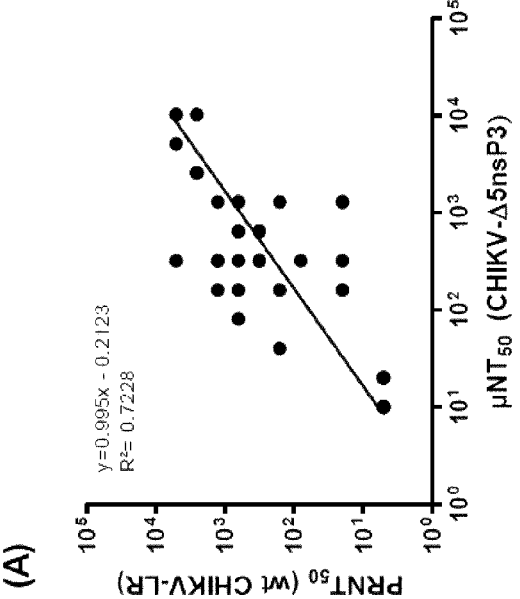

SEQUENCE LISTING

```
<160> NUMBER OF SEQ ID NOS: 7

<210> SEQ ID NO 1
<211> LENGTH: 11674
<212> TYPE: DNA
<213> ORGANISM: Chikungunya virus

<400> SEQUENCE: 1
gatggctgcg tgagacacac gtagcctacc agtttcttac tgctctactc tgcaaagcaa      60
gagattaata acccatcatg gatcctgtgt acgtggacat agacgctgac agcgcctttt     120
tgaaggccct gcaacgtgcg tacccccatgt ttgaggtgga accaaggcag gtcacaccga     180
atgaccatgc taatgctaga gcgttctcgc atctagctat aaaactaata gagcaggaaa     240
ttgaccccga ctcaaccatc ctggatatcg gcagtgcgcc agcaaggagg atgatgtcgg     300
acaggaagta ccactgcgtc tgcccgatgc gcagtgcgga gatcccgag agactcgcca     360 attatgcgag aaagctagca tctgccgcag gaaaagtcct ggacagaaac atctctggaa     420
agatcgggga cttacaagca gtaatggccg tgccagacac ggagacgcca acattctgct     480
```

-continued

```
tacacacaga cgtctcatgt agacagagag cagacgtcgc tatataccaa gacgtctatg     540
ctgtacacgc acccacgtcg ctataccacc aggcgattaa aggggtccga gtggcgtact     600
gggttgggtt cgacacaacc ccgttcatgt acaatgccat ggcgggtgcc tacccctcat     660
actcgacaaa ctgggcagat gagcaggtac tgaaggctaa gaacatagga ttatgttcaa     720
cagacctgac ggaaggtaga cgaggcaagt tgtctattat gagagggaaa aagctaaaac     780
cgtgcgaccg tgtgctgttc tcagtagggt caacgctcta cccggaaagc cgcaagctac     840
ttaagagctg gcacctgcca tcggtgttcc atttaaaggg caaactcagc ttcacatgcc     900
gctgtgatac agtggtttcg tgtgagggct acgtcgttaa gagaataacg atgagcccag     960
gcctttatgg aaaaaccaca gggtatgcgg taacccacca cgcagacgga ttcctgatgt    1020
gcaagactac cgacacggtt gacggcgaaa gaatgtcatt ctcggtgtgc acatacgtgc    1080
cggcgaccat ttgtgatcaa atgaccggca tccttgctac agaagtcacg ccggaggatg    1140
cacagaagct gttggtgggg ctgaaccaga gaatagtggt taacggcaga acgcaacgga    1200
atacgaacac catgaaaaat tatctgcttc ccgtggtcgc ccaagccttc agtaagtggg    1260
caaaggagtg ccggaaagac atggaagatg aaaaactcct gggggtcaga gaaagaacac    1320
tgacctgctg ctgtctatgg gcattcaaga agcagaaaac acacacggtc tacaagaggc    1380
ctgataccca gtcaattcag aaggttcagg ccgagtttga cagctttgtg gtaccgagtc    1440
tgtggtcgtc cggggttgtca atccctttga ggactagaat caaatggttg ttaagcaagg    1500
tgccaaaaac cgacctgatc ccatacagcg gagacgcccg agaagcccgg gacgcagaaa    1560
aagaagcaga ggaagaacga gaagcagaac tgactcgcga agccctacca cctctacagg    1620
cagcacagga agatgttcag gtcgaaatcg acgtggaaca gcttgaggac agagcgggcg    1680
caggaataat agagactccg agaggagcta tcaaagttac tgcccaacca acagaccacg    1740
tcgtgggaga gtacctggta ctctccccgc agaccgtact acgtagccag aagctcagtc    1800
tgattcacgc tttggcggag caagtgaaga cgtgcacgca caacgacga gcagggaggt     1860 atgcggtcga agcgtacgac ggccgagtcc tagtgccctc aggctatgca atctcgcctg    1920
aagacttcca gagtctaagc gaaagcgcaa cgatggtgta taacgaaaga gagttcgtaa    1980
acagaaagct acaccatatt gcgatgcacg accagccct gaacaccgac gaagagtcgt     2040
atgagctggt gagggcagag aggacagaac acgagtacgt ctacgacgtg gatcagagaa    2100
gatgctgtaa gaaggaagaa gccgcaggac tggtactggt gggcgacttg actaatccgc    2160
cctaccacga attcgcatat gaagggctaa aaatccgccc tgcctgccca tacaaaattg    2220
cagtcatagg agtcttcgga gtaccgggat ctggcaagtc agctattatc aagaacctag    2280
ttaccaggca ggacctggtg actagcggaa agaaagaaaa ctgccaagaa atcaccaccg    2340
acgtgatgag acagagaggt ctagagatat ctgcacgtac ggttgactcg ctgctcttga    2400
atggatgcaa cagaccagtc gacgtgttgt acgtagacga ggcgtttgcg tgccactctg    2460
gaacgctact tgctttgatc gccttggtga gaccaaggca gaaagttgta ctttgtggtg    2520
acccgaagca gtgcggcttc ttcaatatga tgcagatgaa agtcaactat aatcacaaca    2580
tctgcaccca gtgtaccac aaaagtatct ccaggcggtg tacactgcct gtgaccgcca    2640
ttgtgtcatc gttgcattac gaaggcaaaa tgcgcactac gaatgagtac aacaagccga    2700
ttgtagtgga cactacaggc tcaacaaac ctgaccctgg agacctcgtg ttaacgtgct    2760
tcagagggtg ggtaaacaa ctgcaaattg actatcgtgg atacgaggtc atgacagcag    2820
ccgcatccca agggttaacc agaaaaggag tttacgcagt tagacaaaaa gttaatgaaa    2880
```

```
acccgctcta tgcatcaacg tcagagcacg tcaacgtact cctaacgcgt acggaaggta      2940
aactggtatg gaagacactt tccggcgacc cgtggataaa gacgctgcag aacccaccga      3000
aaggaaactt caaagcaact attaaggagt gggaggtgga gcatgcatca ataatggcgg      3060
gcatctgcag tcaccaaatg accttcgata cattccaaaa taaagccaac gtttgttggg      3120
ctaagagctt ggtccctatc ctcgaaacag cggggataaa actaaatgat aggcagtggt      3180
ctcagataat tcaagccttc aaagaagaca aagcatactc acctgaagta gccctgaatg      3240
aaatatgtac gcgcatgtat ggggtggatc tagacagcgg gctattttct aaaccgttgg      3300
tgtctgtgta ttacgcggat aaccactggg ataataggcc tggagggaaa atgttcggat      3360
ttaaccccga ggcagcatcc attctagaaa gaaagtatcc attcacaaaa gggaagtgga      3420
acatcaacaa gcagatctgc gtgactacca ggaggataga agactttaac cctaccacca      3480
acatcatacc ggccaacagg agactaccac actcattagt ggccgaacac cgcccagtaa      3540
aaggggaaag aatggaatgg ctggttaaca agataaacgg ccaccacgtg ctcctggtca      3600
gtggctataa ccttgcactg cctactaaga gagtcacttg ggtagcgccg ttaggtgtcc      3660
gcggagcgga ctacacatac aacctagagt tgggtctgcc agcaacgctt ggtaggtatg      3720
acctagtggt cataaacatc cacacacctt ttcgcataca ccattaccaa cagtgcgtcg      3780
accacgcaat gaaactgcaa atgctcgggg gtgactcatt gagactgctc aaaccgggcg      3840
gctctctatt gatcagagca tatggttacg cagatagaac cagtgaacga gtcatctgcg      3900
tattgggacg caagtttaga tcgtctagag cgttgaaacc accatgtgtc accagcaaca      3960
ctgagatgtt tttcctattc agcaactttg acaatggcag aaggaatttc acaactcatg      4020
tcatgaacaa tcaactgaat gcagccttcg taggacaggt cacccgagca ggatgtgcac      4080
cgtcgtaccg ggtaaaacgc atggacatcg cgaagaacga tgaagagtgc gtagtcaacg      4140
ccgctaaccc tcgcgggtta ccgggtggcg gtgtttgcaa ggcagtatac aaaaaatggc      4200
cggagtcctt taagaacagt gcaacaccag tgggaaccgc aaaaacagtt atgtgcggta      4260
cgtatccagt aatccacgct gttggaccaa acttctctaa ttattcggag tctgaagggg      4320
accgggaatt ggcagctgcc tatcgagaag tcgcaaagga agtaactagg ctgggagtaa      4380
atagtgtagc tatacctctc ctctccacag gtgtatactc aggagggaaa gacaggctga      4440
cccagtcact gaaccacctc tttacagcca tggactcgac ggatgcagac gtggtcatct      4500
actgccgcga caaagaatgg gagaagaaaa tatctgaggc catacagatg cggacccaag      4560
tagagctgct ggatgagcac atctccatag actgcgatat tgttcgcgtg caccctgaca      4620
gcagcttggc aggcagaaaa ggatacagca ccacggaagg cgcactgtac tcatatctag      4680
aagggacccg ttttcatcag acggctgtgg atatggcgga gatacatact atgtggccaa      4740
agcaaacaga ggccaatgag caagtctgcc tatatgccct gggggaaagt attgaatcga      4800
tcaggcagaa atgcccggtg gatgatgcag acgcatcatc tcccccaaa actgtccgt       4860 gcctttgccg ttacgctatg actccagaac gcgtcacccg gcttcgcatg aaccacgtca      4920
caagcataat tgtgtgttct tcgtttcccc tcccaaagta caaaatagaa ggagtgcaaa      4980
aagtcaaatg ctctaaggta atgctatttg accacaacgt gccatcgcgc gtaagtccaa      5040
gggcttatag aggtgccgct gccggtaacc ttgcggccgt gtctgattgg gtaatgagca      5100
ccgtacctgt cgcgccgccc agaagaaggc gagggagaaa cctgactgtg acatgtgacg      5160
agagagaagg gaatataaca cccatggcta gcgtccgatt ctttagggca gagctgtgtc      5220
```

-continued

```
cggtcgtaca agaaacagcg gagacgcgtg acacagcaat gtctcttcag gcaccaccga    5280
gtaccgccac ggaaccgaat catccgccga tctccttcgg agcatcaagc gagacgttcc    5340
ccattacatt tggggacttc aacgaaggag aaatcgaaag cttgtcttct gagctactaa    5400
ctttcggaga cttcttacca ggagaagtgg atgacttgac agacagcgac tggtccacgt    5460
gctcagacac ggacgacgag ttaagactag acagggcagg tgggtatata ttctcgtcgg    5520
acaccggtcc aggtcattta caacagaagt cagtacgcca gtcagtgctg ccggtgaaca    5580
ccctggagga agtccacgag gagaagtgtt acccacctaa gctggatgaa gcaaaggagc    5640
aactattact taagaaactc caggagagtg catccatggc caacagaagc aggtatcagt    5700
cgcgcaaagt agaaaacatg aaagcagcaa tcatccagag actaaagaga ggctgtagac    5760
tatacttaat gtcagagacc ccaaaagtcc ctacttaccg gactacatat ccggcgcctg    5820
tgtactcgcc tccgatcaac gtccgattgt ccaatcccga gtccgcagtg gcagcatgca    5880
atgagttctt agctagaaac tatccaactg tctcatcata ccaaattacc gacgagtatg    5940
atgcatatct agacatggtg gacgggtcgg agagttgcct ggaccgagcg acattcaatc    6000
cgtcaaaact caggagctac ccgaaacagc acgcttacca cgcgccctcc atcagaagcg    6060
ctgtaccgtc cccattccag aacacactac agaatgtact ggcagcagcc acgaaaagaa    6120
actgcaacgt cacacagatg agggaattac ccactttgga ctcagcagta ttcaacgtgg    6180
agtgtttcaa aaaattcgca tgcaaccaag aatactggga agaatttgct gccagcccta    6240
ttaggataac aactgagaat ttagcaacct atgttactaa actaaaaggg ccaaaagcag    6300
cagcgctatt cgcaaaaacc cataatctac tgccactaca ggaagtacca atggataggt    6360
tcacagtaga tatgaaaagg gacgtaaagg tgactcctgg tacaaagcat acagaggaaa    6420
gacctaaggt gcaggttata caggcggctg aaccccttggc gacagcatac ctatgtggga    6480
ttcacagaga gctggttagg aggctgaacg ccgtcctcct acccaatgta catacactat    6540
ttgacatgtc tgccgaggat ttcgatgcca tcatagccgc acactttaag ccaggagaca    6600 ctgtttttgga aacggacata gcctcctttg ataagagcca agatgattca cttgcgctta    6660
ctgctttgat gctgttagag gatttagggg tggatcactc cctgctggac ttgatagagg    6720
ctgctttcgg agagatttcc agctgtcacc taccgacagg tacgcgcttc aagttcggcg    6780
ccatgatgaa atcaggtatg ttcctaactc tgttcgtcaa cacattgtta aacatcacca    6840
tcgccagccg agtgctggaa gatcgtctga caaaatccgc gtgcgcggcc ttcatcggcg    6900
acgacaacat aatacatgga gtcgtctccg atgaattgat ggcagccaga tgtgccactt    6960
ggatgaacat ggaagtgaag atcatagatg cagttgtatc cttgaaagcc ccttactttt    7020
gtggagggtt tatactgcac gatactgtga caggaacagc ttgcagagtg gcagacccgc    7080
taaaaaggct ttttaaactg ggcaaaccgc tagcggcagg tgacgaacaa gatgaagata    7140
gaagacgagc gctggctgac gaagtgatca gatggcaacg aacagggcta attgatgagc    7200
tggagaaagc ggtatactct aggtacgaag tgcagggtat atcagttgtg gtaatgtcca    7260
tggccacctt tgcaagctcc agatccaact tcgagaagct cagaggaccc gtcataactt    7320 tgtacgcgg tcctaaatag gtacgcacta cagctaccta ttttgcagaa gccgacagca    7380
agtatctaaa cactaatcag ctacaatgga gttcatccca acccaaactt tttacaatag    7440
gaggtaccag cctcgaccct ggactccgcg ccctactatc caagtcatca ggcccagacc    7500
gcgccctcag aggcaagctg ggcaacttgc ccagctgatc tcagcagtta ataaactgac    7560
aatgcgcgcg gtaccacaac agaagccacg caggaatcgg aagaataaga agcaaaagca    7620
```

-continued

```
aaaacaacag gcgccacaaa acaacacaaa tcaaaagaag cagccaccta aaaagaaacc     7680
ggctcaaaag aaaaagaagc cgggccgcag agagaggatg tgcatgaaaa tcgaaaatga     7740
ttgtattttc gaagtcaagc acgaaggtaa ggtaacaggt tacgcgtgcc tggtggggga     7800
caaagtaatg aaaccagcac acgtaaaggg gaccatcgat aacgcggacc tggccaaact     7860
ggcctttaag cggtcatcta agtatgacct tgaatgcgcg cagatacccg tgcacatgaa     7920
gtccgacgct tcgaagttca cccatgagaa accggagggg tactacaact ggcaccacgg     7980
agcagtacag tactcaggag gccggttcac catccctaca ggtgctggca aaccagggga     8040
cagcggcaga ccgatcttcg acaacaaggg acgcgtggtg gccatagtct taggaggagc     8100
taatgaagga gcccgtacag ccctctcggt ggtgacctgg aataaagaca ttgtcactaa     8160
aatcaccccc gagggggccg aagagtggag tcttgccatc ccagttatgt gcctgttggc     8220
aaacaccacg ttcccctgct cccagccccc ttgcacgccc tgctgctacg aaaaggaacc     8280
ggaggaaacc ctacgcatgc ttgaggacaa cgtcatgaga cctgggtact atcagctgct     8340
acaagcatcc ttaacatgtt ctccccaccg ccagcgacgc agcaccaagg acaacttcaa     8400
tgtctataaa gccacaagac catacttagc tcactgtccc gactgtggag aagggcactc     8460
gtgccatagt cccgtagcac tagaacgcat cagaaatgaa gcgacagacg ggacgctgaa     8520
aatccaggtc tccttgcaaa tcggaataaa gacggatgac agccacgatt ggaccaagct     8580
gcgttatatg gacaaccaca tgccagcaga cgcagagagg gcggggctat ttgtaagaac     8640
atcagcaccg tgtacgatta ctggaacaat gggacacttc atcctggccc gatgtccaaa     8700
aggggaaact ctgacggtgg gattcactga cagtaggaag attagtcact catgtacgca     8760
cccatttcac cacgaccctc ctgtgatagg tcgggaaaaa ttccattccc gaccgcagca     8820
cggtaaagag ctaccttgca gcacgtacgt gcagagcacc gccgcaacta ccgaggagat     8880
agaggtacac atgcccccag acacccctga tcgcacatta atgtcacaac agtccggcaa     8940
cgtaaagatc acagtcaatg gccagacggt gcggtacaag tgtaattgcg gtggctcaaa     9000
tgaaggacta acaactacag acaaagtgat taataactgc aaggttgatc aatgtcatgc     9060
cgcggtcacc aatcacaaaa agtggcagta taactcccct ctggtcccgc gtaatgctga     9120
acttggggac cgaaaaggaa aaattcacat cccgtttccg ctggcaaatg taacatgcag     9180
ggtgcctaaa gcaaggaacc ccaccgtgac gtacgggaaa aaccaagtca tcatgctact     9240
gtatcctgac cacccaacac tcctgtccta ccggaatatg ggagaagaac caaactatca     9300
agaagagtgg gtgatgcata agaaggaagt cgtgctaacc gtgccgactg aagggctcga     9360
ggtcacgtgg ggcaacaacg agccgtataa gtattggccg cagttatcta caaacggtac     9420
agcccatggc caccgcatg agataattct gtattattat gagctgtacc ccactatgac     9480
tgtagtagtt gtgtcagtgg ccacgttcat actcctgtcg atggtgggta tggcagcggg     9540
gatgtgcatg tgtgcacgac gcagatgcat cacaccgtat gaactgacac caggagctac     9600
cgtccctttc ctgcttagcc taatatgctg catcagaaca gctaaagcgg ccacatacca     9660
agaggctgcg atatacctgt ggaacgagca gcaacctttg ttttggctac aagcccttat     9720
tccgctggca gccctgattg ttctatgcaa ctgtctgaga ctcttaccat gctgctgtaa     9780
aacgttggct tttttagccg taatgagcgt cggtgcccac actgtgagcg cgtacgaaca     9840
cgtaacagtg atcccgaaca cggtgggagt accgtataag actctagtca atagacctgg     9900
ctacagcccc atggtattgg agatggaact actgtcagtc actttggagc caacactatc     9960
```

-continued

```
gcttgattac atcacgtgcg agtacaaaac cgtcatcccg tctccgtacg tgaagtgctg  10020
cggtacagca gagtgcaagg acaaaaacct acctgactac agctgtaagg tcttcaccgg  10080
cgtctaccca tttatgtggg gcggcgccta ctgcttctgc gacgctgaaa acacgcagtt  10140
gagcgaagca cacgtggaga agtccgaatc atgcaaaaca gaatttgcat cagcatacag  10200
ggctcatacc gcatctgcat cagctaagct ccgcgtcctt taccaaggaa ataacatcac  10260
tgtaactgcc tatgcaaacg gcgaccatgc cgtcacagtt aaggacgcca aattcattgt  10320
ggggccaatg tcttcagcct ggacaccttt cgacaacaaa attgtggtgt acaaaggtga  10380
cgtctataac atggactacc gcccctttgg cgcaggaaga ccaggacaat ttggcgatat  10440
ccaaagtcgc acacctgaga gtaaagacgt ctatgctaat acacaactgg tactgcagag  10500
accggctgtg ggtacggtac acgtgccata ctctcaggca ccatctggct ttaagtattg  10560
gctaaaagaa cgcggggcgt cgctgcagca cacagcacca tttggctgcc aaatagcaac  10620
aaacccggta agagcggtga actgcgccgt agggaacatg cccatctcca tcgacatacc  10680
ggaagcggcc ttcactaggg tcgtcgacgc gccctcttta acggacatgt cgtgcgaggt  10740
accagcctgc acccattcct cagactttgg gggcgtcgcc attattaaat atgcagccag  10800
caagaaaggc aagtgtgcgg tgcattcgat gactaacgcc gtcactattc gggaagctga  10860
gatagaagtt gaagggaatt ctcagctgca aatctctttc tcgacggcct tagccagcgc  10920
cgaattccgc gtacaagtct gttctacaca agtacactgt gcagccgagt gccacccccc  10980
gaaggaccac atagtcaact acccggcgtc acataccacc ctcggggtcc aggacatctc  11040
cgctacggcg atgtcatggg tgcagaagat cacgggaggt gtgggactgg ttgttgctgt  11100
tgccgcactg attctaatcg tggtgctatg cgtgtcgttc agcaggcact aacttgacaa  11160
ttaagtatga aggtatatgt gtcccctaag agacacactg tacatagcaa ataatctata  11220
gatcaaaggg ctacgcaacc cctgaatagt aacaaaatac aaaatcacta aaaattataa  11280
aaacagaaaa atacataaat aggtatacgt gtcccctaag agacacattg tatgtaggtg  11340
ataagtatag atcaaagggc cgaataaccc ctgaatagta acaaaatatg aaaatcaata  11400
aaaatcataa aatagaaaaa ccataaacag aagtagttca aagggctata aaacccctga  11460
atagtaacaa aacataaaat taataaaaat caaatgaata ccataattgg caaacggaag  11520
agatgtaggt acttaagctt cctaaaagca gccgaactca ctttgagaag taggcatagc  11580
ataccgaact cttccacgat tctccgaacc cacagggacg taggagatgt tattttgttt  11640
ttaatatttc aaaaaaaaaa aaaaaaaaaa aaaa                              11674
```

```
<210> SEQ ID NO 2
<211> LENGTH: 423
<212> TYPE: PRT
<213> ORGANISM: Chikungunya virus

<400> SEQUENCE: 2

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Asp Ser His Asp Trp
        50                  55                  60

Thr Lys Leu Arg Tyr Met Asp Asn His Met Pro Ala Asp Ala Glu Arg
```

-continued

```
65                    70                    75                    80

Ala Gly Leu Phe Val Arg Thr Ser Ala Pro Cys Thr Ile Thr Gly Thr
                85                    90                    95

Met Gly His Phe Ile Leu Ala Arg Cys Pro Lys Gly Glu Thr Leu Thr
                100                   105                   110

Val Gly Phe Thr Asp Ser Arg Lys Ile Ser His Ser Cys Thr His Pro
                115                   120                   125

Phe His His Asp Pro Pro Val Ile Gly Arg Glu Lys Phe His Ser Arg
        130                   135                   140

Pro Gln His Gly Lys Glu Leu Pro Cys Ser Thr Tyr Val Gln Ser Thr
145                   150                   155                   160

Ala Ala Thr Thr Glu Glu Ile Glu Val His Met Pro Pro Asp Thr Pro
                165                   170                   175

Asp His Thr Leu Met Ser Gln Gln Ser Gly Asn Val Lys Ile Thr Val
                180                   185                   190

Asn Gly Gln Thr Val Arg Tyr Lys Cys Asn Cys Gly Gly Ser Asn Glu
                195                   200                   205

Gly Leu Thr Thr Thr Asp Lys Val Ile Asn Asn Cys Lys Val Asp Gln
        210                   215                   220

Cys His Ala Ala Val Thr Asn His Lys Lys Trp Gln Tyr Asn Ser Pro
225                   230                   235                   240

Leu Val Pro Arg Asn Ala Glu Leu Gly Asp Arg Lys Gly Lys Ile His
                245                   250                   255

Ile Pro Phe Pro Leu Ala Asn Val Thr Cys Arg Val Pro Lys Ala Arg
                260                   265                   270

Asn Pro Thr Val Thr Tyr Gly Lys Asn Gln Val Ile Met Leu Leu Tyr
                275                   280                   285

Pro Asp His Pro Thr Leu Leu Ser Tyr Arg Asn Met Gly Glu Glu Pro
        290                   295                   300

Asn Tyr Gln Glu Glu Trp Val Met His Lys Lys Glu Val Val Leu Thr
305                   310                   315                   320

Val Pro Thr Glu Gly Leu Glu Val Thr Trp Gly Asn Asn Glu Pro Tyr
                325                   330                   335

Lys Tyr Trp Pro Gln Leu Ser Thr Asn Gly Thr Ala His Gly His Pro
                340                   345                   350

His Glu Ile Ile Leu Tyr Tyr Tyr Glu Leu Tyr Pro Thr Met Thr Val
                355                   360                   365

Val Val Val Ser Val Ala Thr Phe Ile Leu Leu Ser Met Val Gly Met
        370                   375                   380

Ala Ala Gly Met Cys Met Cys Ala Arg Arg Arg Cys Ile Thr Pro Tyr
385                   390                   395                   400

Glu Leu Thr Pro Gly Ala Thr Val Pro Phe Leu Leu Ser Leu Ile Cys
                405                   410                   415

Cys Ile Arg Thr Ala Lys Ala
                420
```

<210> SEQ ID NO 3
<211> LENGTH: 423
<212> TYPE: PRT
<213> ORGANISM: Artificial Sequence
<220> FEATURE:
<223> OTHER INFORMATION: mutation arising from Vero passaging

<400> SEQUENCE: 3

Ser Thr Lys Asp Asn Phe Asn Val Tyr Lys Ala Thr Arg Pro Tyr Leu

-continued

```
1                 5                 10                15

Ala His Cys Pro Asp Cys Gly Glu Gly His Ser Cys His Ser Pro Val
            20                25                30

Ala Leu Glu Arg Ile Arg Asn Glu Ala Thr Asp Gly Thr Leu Lys Ile
            35                40                45

Gln Val Ser Leu Gln Ile Gly Ile Lys Thr Asp Asp Ser His Asp Trp
        50                55                60

Thr Lys Leu Arg Tyr Met Asp Asn His Met Pro Ala Asp Ala Glu Arg
65                70                75                80

Ala Gly Leu Phe Val Arg Thr Ser Ala Pro Cys Thr Ile Thr Gly Thr
            85                90                95

Met Gly His Phe Ile Leu Ala Arg Cys Pro Lys Gly Glu Thr Leu Thr
            100               105               110

Val Gly Phe Thr Asp Ser Arg Lys Ile Ser His Ser Cys Thr His Pro
        115               120               125

Phe His His Asp Pro Pro Val Ile Gly Arg Glu Lys Phe His Ser Arg
        130               135               140

Pro Gln His Gly Lys Glu Leu Pro Cys Ser Thr Tyr Val Gln Ser Thr
145               150               155               160

Ala Ala Thr Thr Glu Glu Ile Lys Val His Met Pro Pro Asp Thr Pro
            165               170               175

Asp His Thr Leu Met Ser Gln Gln Ser Gly Asn Val Lys Ile Thr Val
            180               185               190

Asn Gly Gln Thr Val Arg Tyr Lys Cys Asn Cys Gly Gly Ser Asn Glu
            195               200               205

Gly Leu Thr Thr Thr Asp Lys Val Ile Asn Asn Cys Lys Val Asp Gln
        210               215               220

Cys His Ala Ala Val Thr Asn His Lys Lys Trp Gln Tyr Asn Ser Pro
225               230               235               240

Leu Val Pro Arg Asn Ala Glu Leu Gly Asp Arg Lys Gly Lys Ile His
            245               250               255

Ile Pro Phe Pro Leu Ala Asn Val Thr Cys Arg Val Pro Lys Ala Arg
            260               265               270

Asn Pro Thr Val Thr Tyr Gly Lys Asn Gln Val Ile Met Leu Leu Tyr
        275               280               285

Pro Asp His Pro Thr Leu Leu Ser Tyr Arg Asn Met Gly Glu Glu Pro
        290               295               300

Asn Tyr Gln Glu Glu Trp Val Met His Lys Lys Glu Val Val Leu Thr
305               310               315               320

Val Pro Thr Glu Gly Leu Glu Val Thr Trp Gly Asn Asn Glu Pro Tyr
            325               330               335

Lys Tyr Trp Pro Gln Leu Ser Thr Asn Gly Thr Ala His Gly His Pro
            340               345               350

His Glu Ile Ile Leu Tyr Tyr Tyr Glu Leu Tyr Pro Thr Met Thr Val
        355               360               365

Val Val Val Ser Val Ala Thr Phe Ile Leu Leu Ser Met Val Gly Met
        370               375               380

Ala Ala Gly Met Cys Met Cys Ala Arg Arg Arg Cys Ile Thr Pro Tyr
385               390               395               400

Glu Leu Thr Pro Gly Ala Thr Val Pro Phe Leu Leu Ser Leu Ile Cys
            405               410               415

Cys Ile Arg Thr Ala Lys Ala
            420
```

-continued

```
<210> SEQ ID NO 4
<211> LENGTH: 423
<212> TYPE: PRT
<213> ORGANISM: Artificial Sequence
<220> FEATURE:
<223> OTHER INFORMATION: mutation arising from Vero passaging

<400> SEQUENCE: 4

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
        35                  40                  45

Gln Val Ser Leu Gln Ile Arg Ile Lys Thr Asp Asp Ser His Asp Trp
    50                  55                  60

Thr Lys Leu Arg Tyr Met Asp Asn His Met Pro Ala Asp Ala Glu Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
        115                 120                 125

Phe His His Asp Pro Pro Val Ile Gly Arg Glu Lys Phe His Ser Arg
        130                 135                 140

Pro Gln His Gly Lys Glu Leu Pro Cys Ser Thr Tyr Val Gln Ser Thr
145                 150                 155                 160

Ala Ala Thr Thr Glu Glu Ile Glu Val His Met Pro Pro Asp Thr Pro
                165                 170                 175

Asp His Thr Leu Met Ser Gln Gln Ser Gly Asn Val Lys Ile Thr Val
            180                 185                 190

Asn Gly Gln Thr Val Arg Tyr Lys Cys Asn Cys Gly Gly Ser Asn Glu
        195                 200                 205

Gly Leu Thr Thr Thr Asp Lys Val Ile Asn Asn Cys Lys Val Asp Gln
    210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Ile Met Leu Leu Tyr
            275                 280                 285

Pro Asp His Pro Thr Leu Leu Ser Tyr Arg Asn Met Gly Glu Glu Pro
    290                 295                 300

Asn Tyr Gln Glu Glu Trp Val Met His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
            340                 345                 350

His Glu Ile Ile Leu Tyr Tyr Tyr Glu Leu Tyr Pro Thr Met Thr Val
            355                 360                 365
```

-continued

```
Val Val Val Ser Val Ala Thr Phe Ile Leu Leu Ser Met Val Gly Met
    370             375             380

Ala Ala Gly Met Cys Met Cys Ala Arg Arg Arg Cys Ile Thr Pro Tyr
385             390             395             400

Glu Leu Thr Pro Gly Ala Thr Val Pro Phe Leu Leu Ser Leu Ile Cys
            405             410             415

Cys Ile Arg Thr Ala Lys Ala
            420

<210> SEQ ID NO 5
<211> LENGTH: 423
<212> TYPE: PRT
<213> ORGANISM: Artificial Sequence
<220> FEATURE:
<223> OTHER INFORMATION: mutation arising from Vero passaging

<400> SEQUENCE: 5

Ser Thr Lys Asp Asn Phe Asn Val Tyr Lys Ala Thr Arg Pro Tyr Leu
1               5               10              15

Ala His Cys Pro Asp Cys Gly Glu Gly His Ser Cys His Ser Pro Val
            20              25              30

Ala Leu Glu Arg Ile Arg Asn Glu Ala Thr Asp Gly Thr Leu Lys Ile
        35              40              45

Gln Val Ser Leu Gln Ile Gly Ile Lys Thr Asp Asp Ser His Asp Trp
    50              55              60

Thr Lys Leu Arg Tyr Met Asp Asn His Met Pro Ala Asp Ala Glu Arg
65              70              75              80

Ala Gly Leu Phe Val Arg Thr Ser Ala Pro Cys Thr Ile Thr Gly Thr
            85              90              95

Met Gly His Phe Ile Leu Ala Arg Cys Pro Lys Gly Glu Thr Leu Thr
            100             105             110

Val Gly Phe Thr Asp Ser Arg Lys Ile Ser His Ser Cys Thr His Pro
        115             120             125

Phe His His Asp Pro Pro Val Ile Gly Arg Glu Lys Phe His Ser Arg
    130             135             140

Pro Gln His Gly Lys Glu Leu Pro Cys Ser Thr Tyr Val Gln Ser Thr
145             150             155             160

Ala Ala Thr Thr Glu Glu Ile Glu Val His Met Pro Pro Asp Thr Pro
            165             170             175

Asp His Thr Leu Met Ser Gln Gln Ser Gly Asn Val Lys Ile Thr Val
            180             185             190

Asn Gly Gln Thr Val Arg Tyr Lys Cys Asn Cys Gly Gly Ser Asn Glu
        195             200             205

Gly Leu Thr Thr Thr Asp Lys Val Ile Asn Asn Cys Lys Val Asp Gln
        210             215             220

Cys His Ala Ala Val Thr Asn His Lys Lys Trp Gln Tyr Asn Ser Pro
225             230             235             240

Leu Val Pro Arg Asn Ala Lys Leu Gly Asp Arg Lys Gly Lys Ile His
            245             250             255

Ile Pro Phe Pro Leu Ala Asn Val Thr Cys Arg Val Pro Lys Ala Arg
            260             265             270

Asn Pro Thr Val Thr Tyr Gly Lys Asn Gln Val Ile Met Leu Leu Tyr
        275             280             285

Pro Asp His Pro Thr Leu Leu Ser Tyr Arg Asn Met Gly Glu Glu Pro
    290             295             300
```

-continued

```
Asn Tyr Gln Glu Glu Trp Val Met His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
            340                 345                 350

His Glu Ile Ile Leu Tyr Tyr Tyr Glu Leu Tyr Pro Thr Met Thr Val
            355                 360                 365

Val Val Val Ser Val Ala Thr Phe Ile Leu Leu Ser Met Val Gly Met
        370                 375                 380

Ala Ala Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala
            420
```

<210> SEQ ID NO 6
<211> LENGTH: 423
<212> TYPE: PRT
<213> ORGANISM: Artificial Sequence
<220> FEATURE:
<223> OTHER INFORMATION: mutation arising from Vero passaging

<400> SEQUENCE: 6

```
Ser Thr Lys Asp Asn Phe Asn Val Tyr Lys Ala Thr Arg Pro Tyr Leu
1                   5                   10                  15

Ala His Cys Pro Asp Cys Gly Glu Gly His Ser Cys His Ser Pro Val
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Asp Ser His Asp Trp
        50                  55                  60

Thr Lys Leu Arg Tyr Met Asp Asn His Met Pro Ala Asp Ala Glu Arg
65                  70                  75                  80

Ala Arg Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
        115                 120                 125

Phe His His Asp Pro Pro Val Ile Gly Arg Glu Lys Phe His Ser Arg
        130                 135                 140

Pro Gln His Gly Lys Glu Leu Pro Cys Ser Thr Tyr Val Gln Ser Thr
145                 150                 155                 160

Ala Ala Thr Thr Glu Glu Ile Glu Val His Met Pro Pro Asp Thr Pro
                165                 170                 175

Asp His Thr Leu Met Ser Gln Gln Ser Gly Asn Val Lys Ile Thr Val
            180                 185                 190

Asn Gly Gln Thr Val Arg Tyr Lys Cys Asn Cys Gly Gly Ser Asn Glu
            195                 200                 205

Gly Leu Thr Thr Thr Asp Lys Val Ile Asn Asn Cys Lys Val Asp Gln
        210                 215                 220

Cys His Ala Ala Val Thr Asn His Lys Lys Trp Gln Tyr Asn Ser Pro
225                 230                 235                 240
```

-continued

```
Leu Val Pro Arg Asn Ala Glu Leu Gly Asp Arg Lys Gly Lys Ile His
        245             250             255

Ile Pro Phe Pro Leu Ala Asn Val Thr Cys Arg Val Pro Lys Ala Arg
        260             265             270

Asn Pro Thr Val Thr Tyr Gly Lys Asn Gln Val Ile Met Leu Leu Tyr
        275             280             285

Pro Asp His Pro Thr Leu Leu Ser Tyr Arg Asn Met Gly Glu Glu Pro
    290             295             300

Asn Tyr Gln Glu Glu Trp Val Met His Lys Lys Glu Val Val Leu Thr
305             310             315             320

Val Pro Thr Glu Gly Leu Glu Val Thr Trp Gly Asn Asn Glu Pro Tyr
        325             330             335

Lys Tyr Trp Pro Gln Leu Ser Thr Asn Gly Thr Ala His Gly His Pro
        340             345             350

His Glu Ile Ile Leu Tyr Tyr Tyr Glu Leu Tyr Pro Thr Met Thr Val
        355             360             365

Val Val Val Ser Val Ala Thr Phe Ile Leu Leu Ser Met Val Gly Met
    370             375             380

Ala Ala Gly Met Cys Met Cys Ala Arg Arg Arg Cys Ile Thr Pro Tyr
385             390             395             400

Glu Leu Thr Pro Gly Ala Thr Val Pro Phe Leu Leu Ser Leu Ile Cys
        405             410             415

Cys Ile Arg Thr Ala Lys Ala
        420
```

```
<210> SEQ ID NO 7
<211> LENGTH: 423
<212> TYPE: PRT
<213> ORGANISM: Artificial Sequence
<220> FEATURE:
<223> OTHER INFORMATION: mutation arising from Vero passaging

<400> SEQUENCE: 7

Ser Thr Lys Asp Asn Phe Asn Val Tyr Lys Ala Thr Arg Pro Tyr Leu
1               5               10              15

Ala His Cys Pro Asp Cys Gly Glu Gly His Ser Cys His Ser Pro Val
        20              25              30

Ala Leu Glu Arg Ile Arg Asn Glu Ala Thr Asp Gly Thr Leu Lys Ile
        35              40              45

Gln Val Ser Leu Gln Ile Gly Ile Lys Thr Asp Asp Ser His Asp Trp
    50              55              60

Thr Lys Leu Arg Tyr Met Asp Asn His Met Pro Ala Asp Ala Glu Arg
65              70              75              80

Ala Gly Leu Phe Val Arg Thr Ser Ala Pro Cys Thr Ile Thr Gly Thr
        85              90              95

Met Gly His Phe Ile Leu Ala Arg Cys Pro Lys Gly Glu Thr Leu Thr
        100             105             110

Val Gly Phe Thr Asp Ser Arg Lys Ile Ser His Ser Cys Thr His Pro
        115             120             125

Phe His His Asp Pro Pro Val Ile Gly Arg Glu Lys Phe His Ser Arg
        130             135             140

Pro Gln His Gly Lys Glu Leu Pro Cys Ser Thr Tyr Val Gln Ser Thr
145             150             155             160

Ala Ala Thr Thr Glu Glu Ile Glu Val His Met Pro Pro Asp Thr Pro
        165             170             175
```

-continued

```
Asp His Thr Leu Met Ser Gln Gln Ser Gly Asn Val Lys Ile Thr Val
            180                 185                 190

Asn Gly Gln Thr Val Arg Tyr Lys Cys Asn Cys Gly Gly Ser Asn Glu
            195                 200                 205

Gly Leu Thr Thr Thr Asp Lys Val Ile Asn Asn Cys Lys Val Asp Gln
    210                 215                 220

Cys His Ala Ala Val Thr Asn Tyr Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Ile Met Leu Leu Tyr
            275                 280                 285

Pro Asp His Pro Thr Leu Leu Ser Tyr Arg Asn Met Gly Glu Glu Pro
    290                 295                 300

Asn Tyr Gln Glu Glu Trp Val Met His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
                340                 345                 350

His Glu Ile Ile Leu Tyr Tyr Tyr Glu Leu Tyr Pro Thr Met Thr Val
            355                 360                 365

Val Val Val Ser Val Ala Thr Phe Ile Leu Leu Ser Met Val Gly Met
    370                 375                 380

Ala Ala Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala
                420
```

SINGLE SHOT CHIKUNGUNYA VIRUS VACCINE

RELATED APPLICATION

This Application is a national stage filing under 35 U.S.C. 371 of International Patent Application Serial No. PCT/EP2020/072436, filed Aug. 10, 2020, the content of which is incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jan. 12, 2022, is named I0422.70142US00-SEQ-JRV, and is 37,989 bytes in size.

FIELD OF THE INVENTION

The invention relates to a single-shot vaccine against Chikungunya virus comprising a live-attenuated virus and delivered at an optimized dose for long-lasting protection from CHIKV disease.

BACKGROUND OF THE INVENTION

Chikungunya virus (CHIKV) is a positive-sense, single-stranded RNA virus from the genus Alphavirus, family Togaviridae. Transmitted to humans via a mosquito vector, Chikungunya virus disease is mainly an outbreak disease and is associated with high attack rates. CHIKV is currently regarded as one of the most-likely re-emerged viruses to spread globally, and morbidity to this virus is considered a serious threat to global public health raising an urgent demand for efficient prophylaxis. Due to climate change, furthermore, the threat posed by Chikungunya may be amplified, increasing the size of the human population at risk of infection. However, at present there is no treatment or vaccine available against this CHIKV-induced debilitating disease and its various symptoms. CHIKV has been reported in over 100 countries with more than 2.2 million suspected cases in the Americas alone.

CHIKV is a small spherical RNA virus that is closely related to other viruses in Africa, South America and Australia that cause similar symptoms, such as Ross River Virus, Mayaro-virus and O'nyong-nyong-virus. The CHIK virus is vectored by the daytime-biting *Aedes aegypti* mosquito, which also transmits yellow fever, Zika and dengue viruses. CHIKV can also be transmitted by *Aedes albopictus* mosquitoes, a more cold-tolerant mosquito that could readily promote the spread of Chikungunya to more temperate areas of the world (Vega-Rua A, et al., Chikungunya Virus Transmission Potential by Local *Aedes* Mosquitoes in the Americas and Europe (2015) PLOS Neglected Tropical Diseases DOI:10.1371/journal.pntd.0003780). Outbreaks in the past have occurred mainly in Africa, but the East-Central South African (ECSA) genotype has recently expanded its geographical range, resulting in outbreaks in India, Asia, and even temperate Europe (Weaver, S., Arrival of Chikungunya Virus in the New World: Prospects for Spread and Impact on Public Health (2014) PLOS Neglected Tropical Diseases 8(6): e2921). Although CHIKV has been repeatedly imported into the Americas since 1995, autochthonous transmission had not been reported until 2013 in the Caribbean. Further epidemics may been aided in part by the spread of the CHIKV mosquito vector into non-endemic regions, as well as the ability of CHIKV to adapt to local mosquito species. Infection with CHIKV results in chronic and incapacitating arthralgia affecting all gender and age groups, accompanied by an acute febrile disease with headache, muscle pain, and skin rashes. The severe, often debilitating joint pain in infected patients can persist for years, especially in adults. In some cases, neurological, renal, cardiac, respiratory or hepatic complications can also occur. Individuals who are at higher risk of more serious complications include infants, the elderly and individuals with chronic medical conditions. Although infections with CHIKV usually resolve spontaneously, higher risk groups can develop CNS infection (CHIKV encephalitis), which had an overall mortality rate of about 16% in the La Reunion Outbreak of 2005-2006 and a rate of persistent disabilities in children following CHIKV encephalitis of between 30 and 45 percent (Gerardin P, et al. Chikungunya virus-associated encephalitis A cohort study on La Reunion Island, 2005-2009 (2016) Neurology 86:1-9). Since neither a specific antiviral treatment nor a vaccine is available to prevent CHIKV infection, prevention against CHIKV infection is therefore limited to non-treatment interventions such as the employment of insecticides, wearing long sleeves and pants, and other means to restrict exposure to vector mosquitos.

Preclinical studies in mice and Non-human primates (NHPs) have demonstrated the important role of antibodies in protection against CHIKV infection. For example, B cell deficient mice were unable to clear CHIKV viremia, while wild-type mice were competent (Lum F-M. et al., 2013). Specifically, passive transfer of immune sera conferred protection against disease in recipient mice, in contrast to adoptive transfer of primed CD8+ T cells, which had no impact on viremia (Couderc T. et al., 2009; Chu H. et al., 2013; Kam Y-W. et al. 2012; Linn M L. et al., 1998). A combination of neutralizing monoclonal antibodies protected against a lethal challenge with CHIKV in a mouse model (Pal P. et al. 2013). Additionally, the administration of a human neutralizing monoclonal-antibody blocked CHIKV spread and inflammation in NHPs (Broeckel R. et al., 2017).

Importantly, the findings of a prospective longitudinal cohort study in the Philippines further supports the surrogate endpoint for development of the CHIKV-Δ5nsP3 attenuated vaccine. Briefly, acute febrile illnesses were investigated via community-based active surveillance over a period of 12 months in 853 subjects (Yoon I-K et al. (2015) High Rate of Subclinical Chikungunya Virus Infection and Association of Neutralizing Antibody with Protection in a Prospective Cohort in The Philippines. PLoS Negl Trop Dis 9(5): e0003764. doi:10.1371/journal.pntd.0003764). PRNT assays were performed from blood samples obtained at enrolment and at 12 months. In addition, symptomatic CHIKV infections were identified by positive CHIKV PCR in acute blood samples and/or CHIKV IgM/IgG ELISA seroconversion in paired acute/convalescent samples. The authors reported that a baseline CHIKV $PRNT_{80}$ titer $\geq 10$ was associated with 100% (95% CI: 46.1, 100.0) protection from symptomatic CHIKV infection. The aforementioned studies in humans as well as in animals suggest that the induction of CHIKV neutralizing antibodies is likely to predict clinical benefit.

Adding further support to the importance of neutralizing antibodies are studies with several vaccine candidates in development, which have demonstrated that vaccines which induced neutralizing antibodies protected against infection, whereas those inducing mainly CD8-specific T-cells did not (Ahola T. et al, 2015). These preclinical and clinical observations are strongly supported by findings from natural CHIKV infections in humans, such as the Yoon et al. study cited above. Robust IgM/IgG antibody responses are elicited following CHIKV infection in humans that primarily target E1/E2 structural proteins. In addition, it is known that natural CHIKV infection induces a durable antibody response that is believed to confer life-long immunity (Galatas B. et al., 2016; Nitatpattana N. et al.; 2014).

A vaccine for the prevention of Chikungunya infection would be highly advantageous. The vaccine would be important for protecting travelers to endemic regions, as well as for protecting endemic populations. In the case of outbreaks, a vaccine which is quick to produce and distribute, as well as stimulating a quick protective immune response, would be a boon. Currently, a Measles virus-based CHIKV (MV-CHIK) vaccine is in clinical trials and has been shown to confer full seroconversion to some treatment groups (Reisinger, E., et al., 2018, Immunogenicity, safety, and tolerability of the measles-vectored chikungunya virus vaccine MV-CHIK: a double-blind, randomized, placebo-controlled and active-controlled phase 2 trial; The Lancet (392):2718-2727). Based on the relatively low titers elicited by the MV-CHIK and the strong booster effect observed following a second dose, indicating that MV-CHIK does not stimulate sterilizing immunity in vaccinated subjects, MV-CHIK is probably not suitable as a one-shot vaccine. For many travelers, a vaccine requiring a booster weeks or months after the initial vaccination would not be practicable. With regard to vaccine compliance as well, vaccines requiring a booster shot are often problematic. A more desirable candidate in any target population would be a single-shot vaccine that confers long-lasting protective immunity within a matter of days.

In this regard, pre-clinical data with preparations comprising the live-attenuated deletion mutant CHIKV-Δ5nsP3 have previously demonstrated stimulation of CHIKV-neutralizing antibodies and protection against CHIKV challenge in both mouse and non-human primate models. As disclosed herein, data from a phase 1 clinical study of a CHIKV-Δ5nsP3-containing vaccine (referred to herein as "CHIKV-Δ5nsP3-inv" or "CHIKV vaccine candidate") supports the feasibility of developing a safe and effective live-attenuated CHIKV vaccine, which provides long-term protection after only a single immunization. The inclusion in the trial of an intrinsic human virus challenge provides the opportunity to generate early data on efficacy of the single-dose vaccination schedule and supports the advancement of this Chikungunya virus vaccine candidate in response to the urgent medical need for a prophylactic CHIKV vaccine.

SUMMARY OF THE INVENTION

The current invention relates to a live-attenuated Chikungunya virus vaccine candidate (CHIKV-Δ5nsP3-mv) designed for active immunization for the prevention of disease caused by CHIKV in populations living in endemic regions, as well as for travelers to endemic areas or areas at risk for outbreak. The replicating CHIKV vaccine candidate comprises a deletion of 60 amino acids in the non-structural protein (nsP)3 gene encoding the non-structural replicase complex protein nsP3 (see FIG. 1), leading to attenuation of the virus in vivo. The vaccine, based on the La Reunion strain of the East Central South African genotype (LR2006-OPY), is produced in Vero cells and purified by centrifugation, ultrafiltration, batch-chromatography and sucrose gradient centrifugation. Pre-clinical development focused on small animal and non-human primate models. In C57BL/6 mice, the vaccine elicited high titers of binding and neutralizing antibodies after a single immunization and mice were subsequently protected from a high dose CHIKV challenge. Additionally, a single immunization in non-human primates protected against a wild-type CHIKV infection. The novel vaccine is designed to protect against all circulating genotypes of CHIKV throughout the world and potentially against closely related alphaviruses.

The current invention focuses on a clinical dose-finding study designed to investigate the safety and immunogenicity of three escalating dose levels of the live-attenuated CHIKV vaccine candidate in healthy adults. The trial design included an intrinsic homologous human viral challenge, i.e. a re-vaccination with the high dose CHIKV-Δ5nsP3 vaccine, administered at six months or 12 months following a single vaccination. Herein, "challenge" and "re-vaccination" are used interchangeably.

Data collected up to Month 7 after a single immunization of 120 healthy volunteers showed an excellent immunogenicity profile with 100% seroconversion rates already achieved at Day 14 in all dose groups. Mean peak antibody titers at Day 28 range from 592.6 to 686.9 geometric mean titer (GMT) from Groups L (Low dose) to H (High dose), respectively, with maximum titers reaching 2560 GMT. A single vaccination was sufficient to induce sustained high titer neutralizing antibodies, as demonstrated by the absence of an anamnestic response following challenge and the development of sterilizing immunity (96.2% of participants). The vaccine was generally safe and well-tolerated in the Low and Medium dosage groups, with both doses demonstrating a superior reactogenicity profile compared to the High dosage group. Following challenge, vaccinated subjects were protected from vaccine-induced viremia. No adverse events of special interest and no vaccine related serious adverse events were reported.

The present invention relates to a pharmaceutical composition comprising a sufficient amount of immunogenic Chikungunya virus to elicit a neutralizing immune response in a subject; i.e., an immune response that is protective against infection with and/or disease caused by Chikungunya virus. In particular, the invention provides a pharmaceutical composition comprising live-attenuated CHIKV-Δ5nsP3 particles wherein the percentage of said viral particles with immunogenicity-reducing mutations, particularly immunogenicity-reducing mutations in the E2 protein, are minimized. A previous application (WO2019057793, incorporated herein by reference in its entirety) provides a process for producing a pharmaceutical composition comprising a live-attenuated CHIKV-Δ5nsP3, wherein the process minimizes the presence of immunogenicity-reducing mutations in the viral genome, particularly mutations at E168 of viral E2 protein and/or other E2 residues and/or residues in other structural or non-structural CHIKV proteins. The current disclosure further provides pharmaceutical compositions comprising an immunogenic live-attenuated Chikungunya virus obtainable by the process of the invention.

In the course of clinical trials relating to the current invention, it was observed that a vaccine composition comprising live-attenuated CHIKV-Δ5nsP3 particles is generally safe across all three dosage levels (Low, Medium and High; $3.2\times10^3$, $3.2\times10^4$ and $3.2\times10^5$ $TCID_{50}$/dose, respectively), is well-tolerated in the Low and Medium doses and has an excellent immunogenicity profile, stimulating high neutralizing antibody titers after a single vaccination in healthy adults, clearly supporting further development. No adverse events (AEs) of special interest (i.e. AEs resembling a CHIKV-like infection) and no vaccine-related serious adverse events were reported. Injection site reactogenicity was excellent, with less than 7% of vaccines reporting any local AE, all of which were exclusively of mild severity. Reported systemic adverse events were predominantly headache, fever and fatigue, followed by muscle and joint pain; all of which are typical reactions following immunization and comparable to those reported after vaccination with other vaccines in the general population. Severe fever, i.e. a temperature of 38.9° C. (102.1° F.) or higher ($>=38.9°$ C.), was reported in seven subjects, starting 2-4 days after vaccination and lasting for 1-3 days, with maximum temperatures ranging between 38.9 and 39.2° C. in all but one individual who developed a temperature of 40° C. Importantly, five of these fever cases were reported in the High dose group, rendering this dose unsuitable for further development. None of the participants required medical attention. AEs almost exclusively occurred after the single vaccination and not after the challenge dose at Day 180 and Month 12. Furthermore, transient cases of neutropenia, lymphopenia or leukopenia, all in the absence of accompanying clinical signs or symptoms, were also noted. Three cases of severe related neutropenia were reported as AEs in one individual in Group M (n=1) and two in Group L (n=2) following the single vaccination and based on the FDA "Toxicity Grading Scale for Healthy Adult and Adolescent Volunteers Enrolled in Preventive Vaccine Clinical Trials". It should be noted that none of these cases would have been considered severe in clinical practice. Post-vaccination neutropenia is not uncommon, generally transient and clinically benign as reported in a systematic review of live-attenuated licensed as well as candidate vaccines such as dengue, influenza or varicella-zoster (Muturi-Kioi, et al., 2017, PLOS ONE; DOI:10.1371/journal.pone.015738).

The attenuation of the vaccine candidate CHIKV-Δ5nsP3 results in reduced replication capability of the virus. Thus, as demonstrated in preclinical studies, viremia was both delayed and strongly reduced and no clinical manifestations typically associated with wild-type CHIKV infections occurred in non-human primates. Within the phase 1 study individuals were closely monitored for the occurrence of viremia in plasma and urine following vaccination as measured by quantitative real-time PCR. In accordance with other licensed live-attenuated viral vaccines data on viremia in vaccinated subjects, the findings indicated that persistence of the vaccine was indeed short-lived, reaching a peak at Day 3 ($<2.3 \times 10^5$ genomes/mL). Other licensed live-attenuated viral vaccines, such as Influenza (i.e. Flu Mist®, Fluenz Tetra®), Measles-Mumps-Rubella (Varicella) (i.e. Priorix®, M-M-R® II, MMRVAXPRO, ProQuad), Yellow fever (i.e. Stamaril) and Polio (i.e. Polio Sabin) persist over a period of a few days to even weeks. Reassuringly, in contrast to Bandeira et al., who described prolonged shedding in urinary specimens upon infection with Chikungunya, we observed shedding only in a single subject, confirming the attenuated phenotype of CHIKV-Δ5nsP3. These results are in line with Musso et al., who showed that urine as a non-invasive alternative sample to blood as used for many other arboviruses does not enlarge the window of detection for CHIKV RNA.

Epidemiological data from the outbreak in the Americas has illustrated that the occurrence and geographical spread of Chikungunya is of unpredictable nature, characterized by epidemics that are explosive and rapidly moving. Additionally, the clinical development of a CHIKV vaccine is further complicated by the very short time lag from the first identified cases to the peak of the epidemic—often only a single month. As a result, realization of a typical vaccine efficacy trial to demonstrate disease prevention in the course of clinical development appears not to be feasible. Case numbers rise exponentially, but then drop as the immunity of the population increases. To set up and initiate a clinical efficacy trial in less than a month is logistically impossible, therefore one needs a valuable predictor for efficacy. Human challenge models were used successfully as predictive tool for efficacy previously. In the phase 1 study described herein, an intrinsic human viral challenge with the highest dose of the live-attenuated vaccine candidate was incorporated six months after the single vaccination to assess efficacy of the vaccine early in clinical development. Following challenge, not a single positive viremia result was reported among challenged individuals, indicating that vaccines are protected from vaccine-induced viremia—an early indication of efficacy. Furthermore, among challenged participants, rates of vaccine-related adverse events were significantly reduced, including the occurrence of abnormal hematology findings. Since GMTs were comparable across the three dose groups, the finding also suggests that the vaccine is a promising candidate at all dose levels to prevent CHIKV infection.

The live-attenuated vaccine candidate was highly immunogenic in all three dose groups after a single vaccination and induced a potent and durable neutralizing antibody response against CHIKV. Following challenges at both M6 (d180) and M12, GMTs remained unchanged and persisted at the same levels as prior to challenge. Consequently, the challenges did not induce a >4-fold rise in serum neutralizing antibody titers. Only two subjects had an anamnestic antibody response following challenge, demonstrating that the live-attenuated vaccine induced sterilizing humoral immunity in nearly all vaccines for at least twelve months following the single vaccination. Hence, a single-dose vaccination schedule is sufficient to induce sustained high titer neutralizing antibodies.

Accordingly, it is an object of the current invention to provide a stable, well-defined, safe and effective pharmaceutical composition such as, e.g. a vaccine, against Chikungunya virus, which confers quick and long-lasting protection with only one vaccination; i.e., a so called "one-shot" vaccine, and is well-tolerated and safe. The one-shot CHIKV vaccine candidate provided herein has demonstrated surprising results in that it stimulates a very fast onset of protective immunity, leading to complete seroconversion in all vaccinated subjects in a short time frame. Furthermore, no booster effect was observed on challenge, indicating that sterile immunity was conferred.

BRIEF DESCRIPTION OF THE DRAWINGS

The accompanying drawings are not intended to be drawn to scale. The Figures are illustrative only and are not required for enablement of the disclosure. For purposes of clarity, not every component may be labeled in every drawing. In the drawings:

FIG. 15 Clinical trial design (A) and profile (B).

FIG. 17 Viremia in plasma at Days 0, 3, 7 and 14 after immunization (A) and any challenge (B). Limit of Detection (LOD)=1087 GCE/mL, Lower Limit of Quantification (LLOQ)=3261 GCE/mL. Time points with no available results in the treatment group were graphed as 500. GCE/mL—Genome copy equivalents per mL determined by quantitative real-time PCR.

FIG. 18 Shedding of viral particles in urine at Days 0, 3, 7 and 14 after vaccination (A) and any challenge (B). Limit of Detection (LOD)=1087 GCE/mL, Lower Limit of Quantification (LLOQ)=3261 GCE/mL. Time points with no available results in the treatment group were graphed as 500 GCE/mL—Genome copy equivalents per mL determined by quantitative real-time PCR; *Single subject in Group L.

FIG. 19 Assessment of neutralizing antibodies after single vaccination. Seroconversion rates (A) and Geometric Mean Titer (B) after single vaccination by study group. The seroconversion rate was defined for the purposes of the trial as the percentage of subjects reaching a CHIKV-specific antibody titer of at least 20 ($\mu NT_{50} \geq 20$). *Pairwise test p=0.0092.

FIG. 20 Assessment of neutralizing antibodies after challenge at Day 180 (M6) or Month 12 (M12). Seroconversion rates (A) and Geometric Mean Titer (B) in Groups L, M, H1 and H2 before and after re-vaccination with the highest dose at Month 6 or Month 12. Seroconversion was defined for the purposes of the trial as the percentage of subjects reaching a CHIKV-specific antibody titer of at least 20 ($\mu NT_{50} \geq 20$).

FIG. 21 Assessment of seroconversion rates using increasingly stringent cutoff values. Seroconversion rate defined as percentage of subjects reaching a CHIKV-specific antibody titer of at least (A) 40 ($\mu NT_{50}$ 1:40), (B) 80 ($\mu NT_{50}$ 1:80) and (C) 160 ($\mu NT_{50}$ 1:160) after single and re-vaccination by study day and treatment groups.

FIG. 23 Pair-wise comparison of neutralization titers of CHIKV-Δ5nsP3 trial sera collected at different visits of individual subjects measured against the vaccine strain CHIKV-Δ5nsP3 ($\mu NT_{50}$) and (A) the wild-type La Reunion strain ($PRNT_{50}$ wt CHIKV-LR) and (B) the wild type West African strain 37997 ($PRNT_{50}$ wt CHIKV-WA 37997). Three samples having a titer >5,120 in the $PRNT_{50}$ wt CHIKV-LR assay are plotted as 5,120. Negative samples were imputed with half the LLOQ for each method ($\mu NT_{50}$=10, $PRNT_{50}$=5).

DETAILED DESCRIPTION OF THE INVENTION

The present invention provides a pharmaceutical composition comprising a live-attenuated chikungunya virus particle which can be delivered to a subject in need thereof, providing protection against infection with chikungunya virus and/or the development of chikungunya fever after only one shot, i.e., vaccination. In one embodiment, the pharmaceutical composition is an immunogenic composition. In a preferred embodiment, the pharmaceutical composition is a vaccine.

Figure 1:
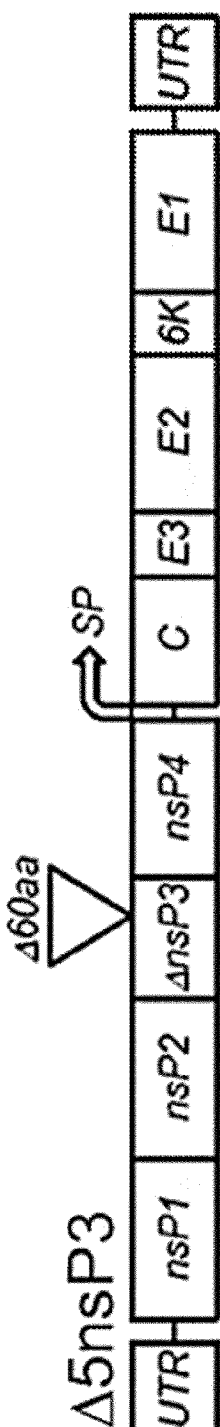
FIG. 1 Schematic representation of the CHIKV-Δ5nsP3 genome structure. The Chikungunya virus genome encodes two polyproteins: non-structural proteins 1-4 (nsP1-4) and structural proteins (C, E3, E2, 6K, E1). Compared with the wild-type genomic sequence, the CHIKV-Δ5nsP3 sequence contains a 183-bp deletion in the 3' part of the sequence encoding nsP3 (amino acids 1656 to 1717 in the nsP1-4 polyprotein), which results in a 60 amino acid deletion in the nsP3 replicase protein (indicated by Δ60aa). SP, subgenomic promoter; UTR, untranslated region. (Figure adapted from Hallengard D, et al., Novel attenuated Chikungunya vaccine candidates elicit protective immunity in C57Bl/6 mice (2014) J. Virol. 88:2858-2866).

The live-attenuated chikungunya virus of the invention is a CHIK virus with an introduced deletion mutation in the nsP3 coding region ("CHIKV-Δ5nsP3") comprising the nucleic acid sequence of SEQ ID NO: 1 or a sequence variant thereof. The live attenuated CHIKV-Δ5nsP3 virus according to SEQ ID NO: 1 and the sequence variants thereof contain a 183-bp deletion in the 3' part of the sequence encoding the nsP3 replicase protein (amino acids 1656 to 1717 in the nsP1-4 polyprotein), which results in a 60 amino acid deletion in nsP3 (indicated by "Δ60aa", FIG. 1), i.e. a truncated nsP3 replicase protein.

Due to its RNA make-up and rapid adaptation to growth on host cells, the CHIKV-Δ5nsP3 attenuated virus is highly prone to mutation during passaging. In this regard, we have previously reported that generation of a CHIKV-Δ5nsP3 seed bank results in different populations of particles, some of which acquire mutations leading to loss or reduction of immunogenicity (see WO2019057793, which is incorporated herein by reference in its entirety). Furthermore, once produced, the virus is unstable and degrades rapidly. The production of a CHIKV-Δ5nsP3 composition and providing a stable formulation thereof, which will ensure that an optimal immunogenic dose is consistently available in each batch even after long-term storage of the vaccine product, therefore, requires careful consideration and is not a trivial matter. In this regard, another important aspect of the one-shot CHIKV-Δ5nsP3-inv vaccine of the current invention is the production process for the formulations; specifically, the lyophilized formulation as set forth in Example 3 and the liquid frozen formulation as set forth in Example 4.

In one aspect, the pharmaceutical composition of the current invention comprises a live attenuated Chikungunya virus. In one aspect, the pharmaceutical composition of the current invention comprises a live attenuated CHIKV comprising an RNA genome defined by the DNA sequence provided by SEQ ID NO: 1. In a preferred embodiment, the pharmaceutical composition of the current invention comprises a mixture of a) the CHIKV-Δ5nsP3 live attenuated virus comprising an RNA genome corresponding to the DNA sequence as provided by SEQ ID NO: 1 and b) sequence variants thereof (mixture referred to herein as "CHIKV-Δ5nsP3-inv"). As used herein, "sequence variant" and "variant" are used interchangeably. In one embodiment, the sequence variants of CHIKV-Δ5nsP3, with an RNA genome corresponding to the DNA sequence as defined by SEQ ID NO: 1 have at least 90-95% sequence identity, at least 96%, 97%, 98% sequence identity, at least 99% sequence identity, preferably greater than 99% sequence identity to the nucleic acid sequence provided by SEQ ID NO: 1, and all encode a truncated nsP3 replicase protein; i.e., maintain the entire 60 aa deletion of nsP3 corresponding to the 60 amino acid deletion in CHIKV-Δ5nsP3. In one embodiment, the sequence variants of CHIKV-Δ5nsP3 express a wild-type E2 protein according to SEQ ID NO: 2. In one aspect, the E2 structural protein of the variants contains one or more point mutations that do not affect the immunogenicity of the virus, i.e., are not immunogenicity reducing. In one embodiment, the point mutations that do not affect the immunogenicity of the virus may be at amino acids 232 and/or 247 of the E2 protein, such as H232Y and/or E247K. In one aspect, the E2 structural protein of the CHIKV-Δ5nsP3 variants contain one or more point mutations that reduce or abolish the immunogenicity of the virus, also referred to as "non-immunogenic" variants such as e.g. E168K. As defined herein, a non-immunogenic CHIKV-Δ5nsP3 sequence variant is a CHIKV-Δ5nsP3 sequence variant which elicits levels of neutralizing antibodies in a vaccinated subject inadequate to prevent signs or symptoms of Chikungunya virus disease. A non-immunogenic CHIKV- Δ5nsP3 sequence variant is further defined as eliciting antibodies in an immunized subject which show poor capacity to neutralize infection of cells with Chikungunya virus (wild-type or attenuated) in an in vitro assay such as e.g., a $PRNT_{50}$ or $\mu NT_{50}$ assay. In particular, a non-immunogenic CHIKV-Δ5nsP3 is defined as eliciting levels of neutralizing antibodies in an immunized subject which provide less than 60%, less than 50%, less than 40%, less than 30%, less than 20%, especially less than 10%, neutralization of Chikungunya virus in an in vitro neutralization assay at a 1:80 or higher serum dilution.

In one embodiment, the E2 structural protein of the CHIKV-Δ5nsP3 sequence variants contains no more than about ten point mutations. In one embodiment, the E2 structural protein of the CHIKV-Δ5nsP3 contains no more than 9, 8, 7, 6, 5 or 4 point mutations. In a preferred embodiment, the E2 structural protein of the CHIKV-Δ5nsP3 sequence variants contains three or less point mutations, most preferably only one or two point mutations, especially only one mutation. In a preferred embodiment, said mutation is an E168K, G55R, E247K G82R or H232Y mutation as defined by SEQ ID Nos: 3-7, respectively, most preferably an E168K mutation as set forth in SEQ ID NO: 3.

In one embodiment, the mixture of CHIKV-Δ5nsP3 and sequence variants thereof comprises at least 25% to 75% of CHIKV-Δ5nsP3 particles comprising an RNA genome corresponding to the DNA sequence provided by SEQ ID NO: 1, preferably at least 40%, preferably at least 50%, preferably more than 60%, preferably more than 70%, preferably more than 80%, most preferably between 40% and 60%. It should be noted that the CHIKV-Δ5nsP3 particles comprising an RNA genome corresponding to the DNA sequence provided by SEQ ID NO: 1 express an E2 protein with the amino acid sequence provided by SEQ ID NO: 2. In one aspect, the sequence variants of CHIKV-Δ5nsP3 are present in the mixture as a heterogeneous population In one aspect, the major sequence variant in the mixture of CHIKV-Δ5nsP3 and sequence variants thereof is the variant expressing an E2 protein with an E168K mutation as set forth in SEQ ID NO: 3. In a preferred aspect, the mixture essentially consists of about 50% CHIKV-Δ5nsP3 according to SEQ ID NO: 1 and about 50% of the variant expressing an E2 protein with an E168K mutation as set forth in SEQ ID NO: 3, especially about 25%:75%, about 30%:70%, about 40%:60%, about 60%:40%, about 70%:30%, about 75%:25%, most preferably about 50%:50%.

The pharmaceutical composition of the invention comprising a mixture of CHIKV-Δ5nsP3 and sequence variants thereof is also herein referred to as "CHIKV-Δ5nsP3-inv". The vaccine was produced in Vero cells and purified according to processes described elsewhere (see WO2019057793, WO2017109223, WO2017109224). CHIKV-Δ5nsP3-inv is referred to herein as CHIKV candidate or CHIKV candidate of the invention.

In preferred embodiments the compositions are provided as unit dosage forms, e.g. comprising a defined dosage of the antigen suitable for administration to a subject in a single dose. The unit dosage forms may be packaged individually, e.g. in single containers, vials, pre-filled syringes or the like. The unit dosage forms may be suitable for immediate administration to the subject (e.g. may comprise a physiologically acceptable concentration of salts) or the unit dosage forms may be provided in concentrated or lyophilized form (e.g. for dilution with sterile saline solution or WFI before use).

In a preferred embodiment, the composition is used as a "one-shot" vaccine, i.e., requires only one vaccination of a subject to be effective, e.g. for the prevention or treatment of chikungunya virus infection. Thus the pharmaceutical composition may be administered as a single dose (e.g. of a unit dosage form as described herein) to a subject in need of vaccination against chikungunya virus infection, without administration of a subsequent or booster dose of the composition. In one embodiment, the composition may be used to induce protective immunity against two or more strains of chikungunya virus, e.g. due to the ability of the composition to induce production of neutralizing antibodies that are cross-reactive for multiple CHIKV strains. As defined herein, prevention of chikungunya virus infection can also mean protection from chikungunya virus infection or disease caused by chikungunya virus infection (such as, e.g., chikungunya fever).

In one embodiment, the pharmaceutical composition of the invention is delivered at a dosage of between about $10^2$ and $10^6$ $TCID_{50}$. As is well-known in the art, $TCID_{50}$ refers the 50 percent tissue culture infective dose and is a measure of infectious viral titer. The $TCID_{50}$ value is a measure of the amount of virus required to infect (and/or induce a cytopathic effect) in 50% of inoculated tissue culture cells. $TCID_{50}$ can be determined using standard assays, such as e.g. an endpoint dilution assay.

In one embodiment, the $TCID_{50}$ value is determined in Vero cells. Preferably the viral titer is calculated according to the Reed and Muench method (e.g. as described in Reed, L. J.; Muench, H. A simple method of estimating fifty percent endpoints (1938) The American Journal of Hygiene 27:493-497). Most preferably the $TCID_{50}$ value is determined substantially as described in Example 3 below.

In one embodiment, the dosage is between about $10^3$ and $10^5$ $TCID_{50}$. In a preferred embodiment, the dosage is about $10^3$ to $2\times10^4$ $TCID_{50}$, most preferably about $5\times10^3$ $TCID_{50}$. In this regard, dosages of $3.2\times10^3$ $TCID_{50}$ (herein, "Low dose"), and $3.2\times10^4$ $TCID_{50}$/ml (herein "Medium dose") showed highly favorable safety profiles (see Example 1). Both also elicited 100% seroconversion in immunized subjects (see Example 2). Furthermore, seroconversion was sustained over the 12 months following vaccination. It should be noted that the Medium dose group had a slightly quicker onset of immune response and a higher GMT value at 12 months when compared with the Low dose group. A desirable dosage for the live attenuated CHIKV of the invention is one that confers the highest and most sustained protective immune response while at the same time being well tolerated. In a preferred embodiment, the dosage of the pharmaceutical composition of the invention is about $3.2\times10^4$ $TCID_{50}$ at the time of manufacture and remains at a $TCID_{50}$ of greater than or equal to about $10^3$ $TCID_{50}$/dose, preferably greater than or equal to about $5\times10^3$ $TCID_{50}$/dose until the time of administration. In one embodiment, the pharmaceutical composition is provided as a liquid frozen composition. In a preferred embodiment, the pharmaceutical composition is provided as a lyophilized composition.

In one embodiment, the pharmaceutical composition comprises a pharmaceutically acceptable excipient or excipients. In one aspect, the pharmaceutically acceptable excipients are selected from the group comprising sugars, salts, amino acids, peptides and proteins. In a preferred embodiment, the pharmaceutically acceptable excipients include sucrose, potassium phosphate, sodium citrate, magnesium chloride, D-sorbitol, L-methionine and recombinant human serum albumin (rHSA). In one embodiment, the pharmaceutically acceptable excipients in the pharmaceutical composition essentially consist of about 5% (w/v) sucrose, about 10 mM potassium phosphate, about 25 mM sodium citrate and about 0.01% (w/v) recombinant human serum albumin (rHSA). In one embodiment, the pharmaceutically acceptable excipients in the pharmaceutical composition essentially consist of about 5% (w/v) sucrose; about 5 mM potassium phosphate; about 25 mM sodium citrate; about 5 mM $MgCl_2$; about 0.5% (w/v) D-sorbitol; about 10 mM L-methionine; and about 0.01% (w/v) recombinant human serum albumin (rHSA). In a preferred embodiment, the pharmaceutical composition comprises sucrose at a concentration of about 5% (w/v); potassium phosphate at a concentration of about 5 mM to about 10 mM; sodium citrate at a concentration of about 25 mM sodium; $MgCl_2$ at a concentration of about 10 mM; D-sorbitol at a concentration of about 0.5% (w/v); L-methionine at a concentration of about 10 mM; and recombinant human serum albumin at a concentration of about 0.01% (w/v).

In one embodiment, the pharmaceutical composition increases serum antibody titers in a vaccinated human subject by at least 1 log, relative to a control, within about 5 to 28 days. In a preferred embodiment, the pharmaceutical composition increases serum antibody titers in a vaccinated human subject by at least 1 log, relative to a control, within about 14 days. In a preferred embodiment, the pharmaceutical composition increases serum antibody titers in a vaccinated human subject by at least 1 log, relative to a control, within about 7 days. In one embodiment, said control is pre-immune sera from the same human subject; e.g., collected before vaccination. In one embodiment, said control is sera from a placebo-treated subject or subjects.

In one embodiment, the pharmaceutical composition of the invention stimulates seroconversion in at least 25%, at least 30%, at least 40%, at least 50%, at least 60%, at least 70%, at least 80%, at least 90%, at least 91%, 92%, 93%, 94%, 95%, 96%, 97%, 98%, 99%, up to 100% of vaccinated subjects within 14 days of a single vaccination. In one embodiment, the pharmaceutical composition of the invention stimulates seroconversion in at least 25%, at least 30%, at least 40%, at least 50%, at least 60%, at least 70%, at least 80%, at least 90%, at least 91%, 92%, 93%, 94%, 95%, 96%, 97%, 98%, 99%, up to 100% of vaccinated subjects within 7 days of a single vaccination. In one embodiment, seroconversion is defined as reaching a CHIKV-specific antibody titer, i.e., a neutralizing antibody titer of at least 10 or at least 20, preferably at least 20. The neutralization of Chikungunya virus may be assessed in an in vitro assay, such as a neutralization assay wherein a range of serum dilutions are tested for neutralization of CHIKV infectivity and calculating the dilution that neutralizes 50% of infectivity compared with a negative control. The 50% reduction of CHIKV virus infectivity in a neutralizing assay (such as, for example, a PRNT assay, a µPRNT assay or microneutralization assay, i.e., a µNT assay) by a 1:10 or higher dilution, preferably at least a 1:20 dilution, of immune sera is defined herein as seroconversion. The value is reported as the reciprocal of the dilution factor, e.g., 50% CHIKV neutralization at a 1:10 immune serum dilution is referred to as a neutralizing titer of 10, e.g., a $µNT_{50}$ titer of 10 or $PRNT_{50}$ titer of 10. Any neutralizing titer values of 20 or higher are all defined as seroconversion herein, with 20 being the minimum possible value.

In one embodiment, the pharmaceutical composition of the invention confers a protective immune response against CHIK virus disease that is long-lasting. In one embodiment, the pharmaceutical composition of the invention confers lifelong protection against CHIK virus disease. In one embodiment, the protective immune response is sustained from at least 6 months up to a lifetime, e.g., several decades, such as 10 to 70 years or beyond. In one embodiment, the protective immune response is sustained up to at least 50 years, at least 40 years, at least 30 years, at least 25 years, at least 20 years, at least 19, 18, 17, 16, 15, 14, 13, 12, 11, 10, 9, 8, 7, 6, 5, 4, 3, 2 years, at least 1 year. In a preferred embodiment, the protective immune response lasts at least 6 months, at least 12 months, at least 24 months, preferably at least 10 years, most preferably for the lifetime of the subject. A protective immune response is an immune response in which levels of elicited neutralizing antibodies are sufficient for reducing or preventing signs or symptoms of Chikungunya virus disease in an immunized subject.

In one embodiment, the pharmaceutical composition is suitable for use in a method of treating or preventing a Chikungunya virus infection. Particularly, the pharmaceutical composition is suitable for use in vaccinating a human subject and stimulating a protective immune response in said subject. In a preferred embodiment, the method of treating or preventing a Chikungunya virus infection according to the current invention comprises administering an effective amount of the pharmaceutical composition as defined herein to a subject in need thereof. A subject in need of vaccination against CHIKV according to the current disclosure can be any human subject in danger of exposure to the virus, such as a traveller to an endemic or outbreak country or an inhabitant of an endemic or outbreak country or a country in danger of an outbreak. Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

Abbreviations

| | |
|---|---|
| CHIKV | Chikungunya virus |
| CPE | Cytopathic effect |
| CRO | Contract research organization |
| ED | Effective dose |
| ELISA | Enzyme-linked immunosorbent assay |
| ELU/ml | ELISA units per ml |
| ECSA | East Central South African |
| GMC | Genome copy equivalents |
| CMT | Geometric Mean Titer |
| GMFI | Geometric Mean Fold Increase |
| HRP | Horseradish peroxidase |
| IgG | Immunoglobulin G |
| IgM | Immunoglobulin M |
| IOL | Indian Ocean Lineage |
| i.m. | Intramuscularly |
| LLOQ | Lower limit of quantification |
| (μ)PRNT | (Micro-) plaque reduction neutralization test |

14

-continued

| | |
|---|---|
| μNT | Micro-neutralization test |
| PAHO | Pan American Health Organization |
| PBS | Phosphate-buffered saline |
| PFU | Plaque forming unit |
| RNA | Ribonucleic acid |
| TCID | Tissue culture infectious dose |
| TMB | Teramothylbenzidine |
| VLP | Virus-like particle |
| WA | West African |

EXAMPLES

Example 1. Safety and Tolerability of the Attenuated CHIKV-Δ5nsP3 Vaccine

A randomized, observer-blinded, multicenter phase 1 trial to assess the safety, immunogenicity and antibody persistence of three escalating dosages of the live-attenuated Chikungunya virus vaccine candidate CHIKV-Δ5nsP3 (a.k.a. CHIKV-Δ5nsP3-inv; i.e., a mixture of CHIKV-Δ5nsP3 and variants) in healthy male and female volunteers was conducted. For the trial, the liquid frozen formulations as disclosed herein were used. Healthy volunteers aged 18 to 45 years were randomly assigned 1:1:2 to Low, Medium and High dose groups (L=3.2×10³ TCID$_{50}$/0.1 ml dose, M=3.2× 10⁴ TCID$_{50}$/1 ml dose, H=3.2×10⁵ TCID$_{50}$/1 ml dose) and each received a single-shot immunization on Day 0. Half of the individuals in Group H (Group H2) were challenged with the High dose at Month 6 and followed up 28 days post-challenge until Month 12. Individuals in Groups L, M and H1 were challenged with the High dose vaccine at Month 12 and followed up to 28 days post-challenge. (See FIGS. 15A and B.)

The study was conducted in compliance with the current International Conference on Harmonisation (ICH) of Technical Requirements for Registration of Pharmaceuticals for Human Use/Guideline for Good Clinical Practice and in accordance with the principles set forth in the Declaration of Helsinki. Throughout the study, an independent data safety monitoring board consisting of four external medical experts performed periodic reviews of accruing safety information. All enrolled subjects provided their written informed consent prior to any study-related procedure.

Healthy adults of both genders, aged 18 to 45 years, were eligible for inclusion in the trial. The baseline characteristics of the subjects are provided in Table 1. Female participants were eligible if they were of non-childbearing potential (i.e. surgically sterile or five years post-menopause). The main exclusion criteria included prior CHIKV infection, history of immune-mediated or chronic arthritis/arthralgia or immunization with an inactivated vaccine within 4 weeks or a live vaccine within 8 weeks prior to vaccination in the study. A full list of inclusion and exclusion criteria is provided in Table 2. One hundred and twenty participants were selected and randomly assigned to receive the single vaccination on Day 0 (FIG. 15B). Twenty-nine vaccines terminated the study prior to Month 13, six were lost to follow-up and 20 withdrew their consent (none due to AEs). One subject was withdrawn from challenge due to an AE (syncope). Two other subjects were withdrawn due to unknown reasons. Baseline characteristics across all dosage groups were similar, with the exception that the majority of volunteers were male (Table 1). This gender disparity is reflected by the inclusion criterion allowing the enrollment of female subjects of non-childbearing potential only (Table 2).

TABLE 1

| | | | | All |
|---|---|---|---|---|
| Baseline Characteristics of Participants | | | | |
| | Group L (N = 31) | Group M (N = 30) | Group H (N = 59) | Participants N = 120 |
| Sex n (%) | | | | |
| Male | 28 (90 · 3) | 23 (76 · 7) | 55 (93 · 2) | 106 (88 · 3) |
| Female | 3 (9 · 7) | 7 (23 · 3) | 4 (6 · 8) | 14 (11 · 7) |
| Ethnic origin (%) | | | | |
| American Indian or Alaskan Native | 0 (0 · 0) | 0 (0 · 0) | 1 (1 · 7) | 1 (0 · 8) |
| Asian | 2 (6 · 5) | 1 (3 · 3) | 2 (3 · 4) | 5 (4 · 2) |
| African American | 6 (19 · 4) | 3 (10 · 0) | 8 (13 · 6) | 17 (14 · 2) |
| Native Hawaiian or Other Pacific Islander | 0 (0 · 0) | 0 (0 · 0) | 0 (0 · 0) | 0 (0 · 0) |
| Caucasian | 22 (71 · 0) | 26 (86 · 7) | 48 (81 · 4) | 96 (80 · 0) |
| Other | 1 (3 · 2) | 0 (0 · 0) | 0 (0 · 0) | 1 (0 · 8) |
| Age at screening [years] Mean | 32 · 8 | 32 · 3 | 32 · 5 | 32 · 5 |
| (Min/Max) | (21 · 0/43 · 0) | (21 · 0/45·0) | (19 · 0/45 · 0) | (19 · 0/45 · 0) |
| Height [cm] Mean | 179 · 3 | 174 · 8 | 179 · 1 | 178 · 1 |
| (Min/Max) | (157 · 5/195 · .6) | (152 · 4/190 · 5) | (160 · 0/200 · 7) | (152 · 4/200 · 7) |
| Weight [kg] Mean | 84 · 1 | 77 · 1 | 83 · 7 | 82 · 1 |
| (Min/Max) | (63 · 0/104 · 0) | (45 · 7/100 · 7) | (57 · 6/118 0) | (45 · 7/118 · 0) |
| BMI [kg/m$^2$] Mean | 26 · 2 | 25 · 1 | 26 · 0 | 25 · 8 |
| (Min/Max) | (20 · 8/29 · 4) | (19 · 0/29 · 9) | (20 · 1/29 · 8) | (19 · 0/29 · 7) |

TABLE 2

Inclusion and Exclusion Criteria for Participants

Inclusion Criteria
Subjects who meet ALL of the following criteria are eligible for this study:

1. Subject is 18 to 45 years of age on the Day of screening (Visit 0);
2. Subject has a BMI of ≥18.5 and <30 kg/m2 on the Day of screening (Visit 0);
3. Subject has an understanding of the study and its procedures, agrees to its provisions, and gives written informed consent prior to any study-related procedures;
4. Subject is generally healthy as determined by the Investigator's clinical judgement based on medical history, physical examination and screening laboratory tests;
5. If subject is of childbearing potential:
a) Subject has practiced an adequate method of contraception (see below) during the 30 days before screening (Visit 0);
b) Subject has a negative serum pregnancy test at screening (Visit 0);
c) Subject agrees to employ adequate birth control measures for the duration of the study. This includes one of the following measures:
Hormonal contraceptives (e.g. implants, birth control pills, patches);
Intrauterine device;
Barrier type of birth control measure (e.g. condoms, diaphragms, cervical caps);
Vasectomy in the male sex partner ≥3 months prior to first vaccination.
Exclusion Criteria
Subjects who meet ANY of the following criteria are NOT eligible for this study:

1. Subject has a history of known CHIKV infection;
2. Subject has plans to travel to areas with active CHIKV transmission during the course of the study or has travelled to an endemic CHIKV area within 4 weeks prior to study enrollment;
3. Subject has participated in a clinical study involving an investigational CHIKV vaccine;
4. Subject has received an inactivated vaccine within 4 weeks or live vaccine within 8 weeks prior to vaccination in this study;
5. Subject tests positive for human immunodeficiency virus (HIV), hepatitis B surface antigen (HBsAg) or hepatitis C virus (HCV);
6. Subject has at screening (Visit 0): (1) abnormal laboratory liver function values (≥grade 1), (2) any grade 1 abnormal lab values deemed clinically relevant by the Investigator, or (3) any ≥grade 2 abnormal lab values irrespective of clinical significance;
7. Subject has a clinically significant abnormal ECG at screening (Visit 0);
8. Subject currently has or has a history of significant cardiovascular, respiratory (including asthma), metabolic, neurological, hepatic, heumatic, autoimmune, hematological, gastrointestinal or renal disorder;
9. Subject has a history of immune-mediated or clinically significant arthritis/arthralgia;
10. Subject has a history of malignancy other than squamous cell or basal cell skin cancer, unless there has been surgical excision that is considered to have achieved a cure. A history of hematologic malignancy is a permanent exclusion. Subjects with a history of skin cancer must not be vaccinated at the previous tumor site;

TABLE 2-continued

Inclusion and Exclusion Criteria for Participants

11. Subject has a disease or is undergoing a form of treatment or was undergoing a form of treatment that can be expected
    to influence immune response. Such treatment includes, but is not limited to, systemic or high dose inhaled (>800
    μg/day of beclomethasone dipropionate or equivalent) corticosteroids within 4 weeks prior to study entry, radiation
    therapy or immunosuppressive cytotoxic drugs/monoclonal antibodies in the previous 3 years;
12. Subject has a history of severe hypersensitivity reactions or anaphylaxis;
13. Subject has a history of any vaccine related contraindicating event (e.g., anaphylaxis, allergy to components of the
    candidate vaccine, other known contraindications);
14. Subject had acute febrile infections within two weeks prior to vaccination;
15. Subject has plans to become pregnant during the course of the study, or is pregnant (positive serum pregnancy test at
    screening) or lactating at the time of enrollment;
16. Subject has donated blood within 30 days or received blood-derived products (e.g. plasma) within 90 days prior to
    vaccination in this study or plans to donate blood or use blood products during the course of the study;
17. Subject has a rash, dermatological condition or tattoos that would, in the opinion of the Investigator, interfere with
    injection site reaction rating;
18. Subject has a known or suspected problem with alcohol or drug abuse as determined by the Investigator;
19. Subject has any condition that, in the opinion of the Investigator, may compromise the subjects well-being, might
    interfere with evaluation of study endpoints, or would limit the subject's ability to complete the study;
20. Subject is committed to an institution (by virtue of an order issued either by the judicial or the administrative
    authorities);
21. Subject has participated in another clinical study involving an investigational medicinal product (IMP) or device
    within 30 days prior to study enrollment or is scheduled to participate in another clinical study involving an IMP, or
    device during the course of this study;
22. Subject is a member of the team conducting the study or in a dependent relationship with one of the study team
    members. Dependent relationships include close relatives (i.e., children, partner/spouse, siblings, parents) as well as
    employees of the Investigator or site personnel conducting the study.

Figure 15A:
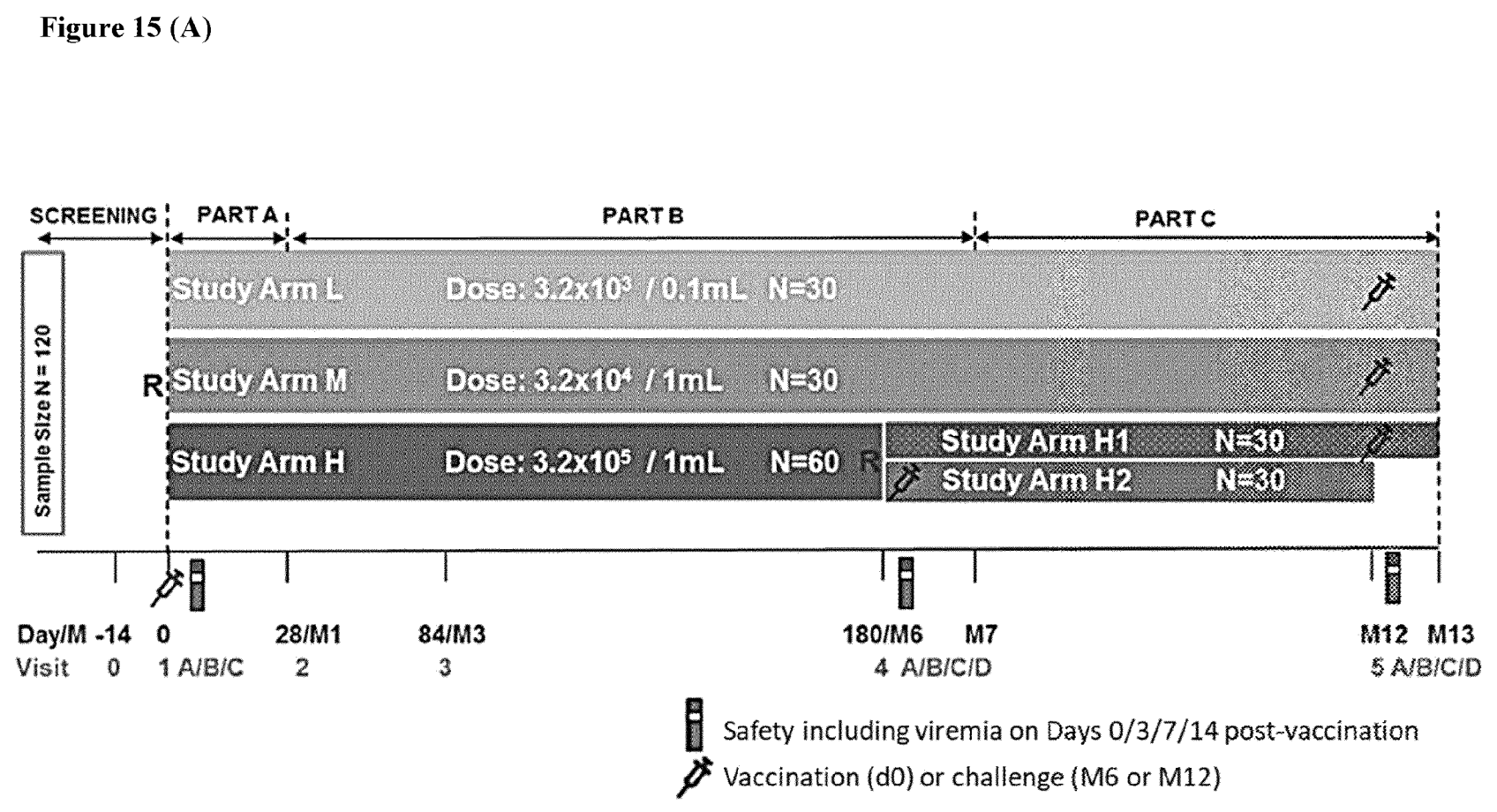
Figure 15B:
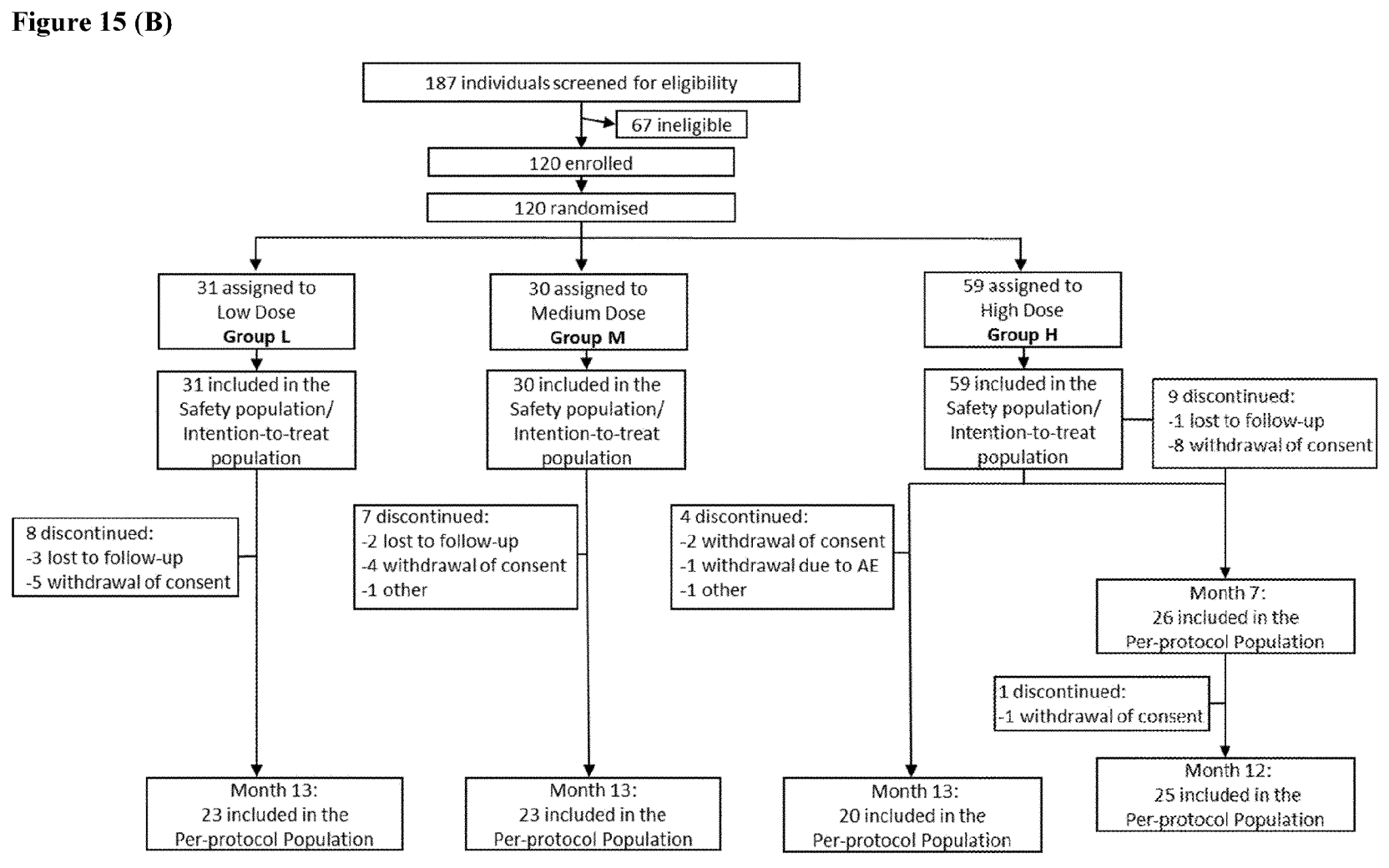

As shown in FIG. 15A, individuals were randomized 1:1:2 to Low dose (Group L) $3.2\times10^3$ $TCID_{50}$/0.1 ml dose, Medium dose (Group M) $3.2\times10^4$ $TCID_{50}$/ml dose or High dose (Group H) $3.2\times10^5$ $TCID_{50}$/ml dose to receive a single i.m. vaccination on Day 0. Dosing was adjusted by injection volume. Participants in dose Group H were re-randomized 1:1 at Month 6 to receive either a challenge with the High dose at Month 6 or Month 12. Participants in the Low and Medium dose groups were challenged with the High dose vaccine at Month 12 only. Participants and investigators were blinded to the assignment into dose groups. Randomization was performed via randomization envelopes in ascending order. The vaccine was prepared by unblinded study staff, unobserved by blinded staff members and the participant. Syringe content was masked prior to administration. For safety and immunogenicity evaluations, blood was drawn before the vaccinations (Day 0), at Days three, seven, 14, 28 and 180 post-vaccination, as well as at 84 days and 12 months after the single vaccination.

The primary objective was to assess safety and tolerability of the vaccine after a single vaccination. Participant diaries were used for the collection of daily oral body temperature, solicited injection and systemic reactions up to 14 days post-vaccination, which are assessed using FDA's toxicity grading scale. In addition, participants were monitored for symptoms suggesting an acute stage of CHIKV-associated events manifested by systemic symptoms presenting with sudden onset of fever, myalgia, headache, back pain and macular to maculopapular rash, sometimes with cutaneous pruritus (foot arch) and edema of the face and extremities, polyadenopathies, acute (poly)arthritis most frequently in the extremities (wrists, ankles and phalanges), tenosynovitis, neurological symptoms or cardiac symptoms.

For determination of viremia and shedding after vaccination and challenge, plasma and urine from subjects were analyzed for the presence of CHIKV genomic RNA by Reverse Transcriptase quantitative PCR (RT-qPCR) (Panning, M. et al., 2008, Chikungunya Fever in Travelers Returning to Europe from the Indian Ocean Region, 2006. Emerging Infectious Diseases 14(3):416-422; Pastorino B. et al., 2015, Development of a TaqMan RT-PCR assay without RNA extraction step for detection and quantification of African Chikungunya viruses, Journal of Virological Methods, 65-71). In brief, total RNA was extracted from individual specimens and subjected to RT-qPCR using a hydrolysis probe and primers specific to the CHIKV nsP1 gene. The read-out was quantitative and reported as the number of CHIKV genome copy equivalents (GCE) per 1 mL of initial subject specimen. The assay was qualified for precision and specificity. The limits of detection and quantification were defined as 1087 GCE/mL (10 GCE/reaction) and 3261 GCE/mL (30 GCE/reaction), respectively. Time points with no available results in the treatment group were plotted at 500.

Statistical analysis. The sample size of 120 participants allowed for the detection of AEs, which commonly have a close relationship to vaccination, and with a true underlying prevalence of 2.5% with a probability of 95%. The study was not powered to detect uncommon or rare AEs, thus a placebo group was not included. All participants who received a single vaccination at Day 0 were included in the safety dataset. The number and percentage of individuals with solicited injection site and systemic reactions up to 14 days after each vaccination, and with unsolicited AEs and SAEs were presented for each dose group overall and by body system/preferred term and were compared using Fisher's exact test for differences between groups; a significant overall test was amended by pair-wise tests between individual groups.

The primary outcome of the study was to assess the safety and tolerability of the vaccine. The live-attenuated CHIKV-Δ5nsP3 vaccine was generally safe and well-tolerated up to Month 12 after the single vaccination in the Low and Medium dosage groups and generally safe in all dosage groups. A summary of adverse events after the single vaccination is provided in Table 3. The Low and Medium dosages showed a superior reactogenicity profile compared to the High dosage group (p-value 0.0089; pairwise test M vs. H 0.0042). The vast majority of AEs across the dose groups were assessed as mild or moderate and the majority of AEs were reported after the single vaccination. No adverse event of special interest and no vaccine related serious adverse events were reported. Two unrelated serious adverse events occurred; one event of polytrauma following a car accident and one event of atrial ectopy 62 days following the 6 month re-vaccination (Table 3). Following any challenge, rates of AEs were substantially diminished, only six participants reported related AEs occurring within 28 days after any challenge, indicating that participants were protected from challenge-induced AEs (summary provided in Table 4).

TABLE 3

| | | Summary of Adverse Events after Single Vaccination up to M12 | | | |
|---|---|---|---|---|---|
| | Statistics | Group L (N = 31) | Group M (N = 30) | Group H (N = 59) | p-value (Overall) |
| Any AE | n (%) Obs | 21 (67 · 7) 57 | 19 (63 · 3) 69 | 48 (81 · 4) 209 | 0 · 1349 |
| | [95% CI] | [50 · 1, 81 · 4] | [45 · 5, 78 · 1] | [69 · 6, 89 · 3] | |
| Any related AE | n (%) Obs | 18 (58 · 1) 43 | 14 (46 · 7) 49 | 46 (78 · 0) 168 | 0 · 0089 |
| | [95% CI] | [40 · 8, 73 · 6] | [30 · 2, 63 · 9] | [65 · 9, 86 · 6] | |
| Pairwise test | vs. M | 0 · 4462 | · · · | · · · | |
| | vs. H | 0 · 0550 | 0 · 0042 | · · · | |
| Any severe AE | n (%) Obs | 4 (12 · 9) 4 | 3 (10 · 0) 3 | 7 (11 · 9) 8 | 1 · 0000 |
| | [95% CI] | [5 · 1, 28 · 9] | [3 · 5, 25 · 6] | [5 · 9, 22 · 5] | |
| Any related severe AE | n (%) Obs | 4 (12 · 9) 4 | 2 (6 · 7) 2 | 7 (11 · 9) 8 | 0 · 7998 |
| | [95% CI] | [5 · 1, 28 · 9] | [1 · 8, 21 · 3] | [5 · 9, 22 · 5] | |
| Any SAE | n (%) Obs | 0 (0 · 0) 0 | 1 (3 · 3) 1 | 0 (0 · 0) 0 | 0 · 2500 |
| | [95% CI] | [0 · 0, 11 · 0] | [0 · 6, 16 · 7] | [0 · 0, 6 · 1] | |
| Any related SAE | n (%) Obs | 0 (0 · 0) 0 | 0 (0 · 0) 0 | 0 (0 · 0) 0 | NC |
| | [95% CI] | [0 · 0, 11 · 0] | [0 · 0, 11 · 4] | [0 · 0, 6 · 1] | |
| Any medically attended AE | n (%) Obs | 2 (6 · 5) 4 | 5 (16 · 7) 5 | 10 (16 · 9) 15 | 0 · 3856 |
| | [95% CI] | [1 · 8, 20 · 7] | [7 · 3, 33 · 6] | [9 · 5, 28 · 5] | |
| Any related medically attended AE | n (%) Obs | 1 (3 · 2) 2 | 0 (0 · 0) 0 | 0 (0 · 0) 0 | 0 · 5083 |
| | [95% CI] | [0 · 6, 16 · 2] | [0 · 0, 11 · 4] | [0 · 0, 6 · 1] | |
| Any solicited AE | n (%) Obs | 11 (35 · 5) 23 | 12 (40 · 0) 41 | 40 (67 · 8) 107 | 0 · 0038 |
| | [95% CI] | [21 · 1, 53 · 1] | [24 · 6, 57 · 7] | [55 · 1, 78 · 3] | |
| Pairwise test | vs. M | 0 · 7946 | · · · | · · · | |
| | vs. H | 0 · 0040 | 0 · 0220 | · · · | |
| Any related solicited AE | n (%) Obs | 10 (32 · 3) 20 | 10 (33 · 3) 34 | 40 (67 · 8) 106 | 0 · 0007 |
| Pairwise test | [95% CI] | [18 · 6, 49 · 9] | [19 · 2, 51 · 2] | [55 · 1, 78 · 3] | |
| | vs. M | 1 · 0000 | · · · | · · · | |
| | vs. H | 0 · 0017 | 0 · 0031 | · · · | |
| Any severe solicited AE | n (%) Obs | 1 (3 · 2) 1 | 1 (3 · 3) 1 | 5 (8 · 5) 6 | 0.6796 |
| | [95% CI] | [0 · 6, 16 · 2] | [0 · 6, 16 · 7] | [3 · 7, 18 · 4] | |
| Any solicited local AE | n (%) Obs | 1 (3 · 2) 1 | 2 (6 · 7) 3 | 4 (6 · 8) 4 | 0 · 7827 |
| | [95% CI] | [0 · 6, 16 · 2] | [1 · 8, 21 · 3] | [2 · 7, 16 · 2] | |
| Any solicited systemic AE | n (%) Obs | 11 (35 · 5) 22 | 12 (40·0) 38 | 40 (67 · 8) 103 | 0 · 0038 |
| | [95% CI] | [21 · 1, 53 · 1] | [24 · 6, 57 · 7] | [55 · 1, 78 · 3] | |
| Pairwise test | vs. M | 0 · 7946 | · · · | · · · | |
| | vs. H | 0 · 0040 | 0 · 0220 | · · · | |
| Any severe solicited systemic AE | n (%) Obs | 1 (3 · 2) 1 | 1 (3 · 3) 1 | 5 (8 · 5) 6 | 0 · 6796 |
| | [95% CI] | [0 · 6, 16 · 2] | [0 · 6, 16 · 7] | [3 · 7, 18 · 4] | |
| Any unsolicited AE | n (%) Obs | 17 (54 · 8) 34 | 15 (50 · 0) 28 | 36 (61 · 0) 102 | 0 · 5849 |
| | [95% CI] | [37 · 8, 70 · 8] | [33 · 2, 66 · 8] | [48 · 3, 72 · 4] | |
| Any related unsolicited AE | n (%) Obs | 13 (41 · 9) 23 | 8 (26 · 7) 15 | 29 (49 · 2) 61 | 0 · 1310 |
| | [95% CI] | [26 · 4, 59 · 2] | [14 · 2, 44 · 4] | [36 · 8, 61 · 6] | |
| Any severe unsolicited AE | n (%) Obs | 3 (9 · 7) 3 | 2 (6 · 7) 2 | 2 (3 · 4) 2 | 0 · 4588 |
| | [95% CI] | [3 · 3, 24 · 9] | [1 · 8, 21 · 3] | [0 · 9, 11 · 5] | |
| Any related severe unsolicited AE | n (%) Obs | 3 (9 · 7) 3 | 1 (3 · 3) 1 | 2 (3 · 4) 2 | 0 · 5452 |
| | [95% CI] | [3 · 3, 24 · 9] | [0 · 6, 16 · 7] | [0 · 9, 11 · 5] | |
| Any AESI | n (%) Obs | 0 (0 · 0) 0 | 0 (0 · 0) 0 | 0 (0 · 0) 0 | NC |
| | [95% CI] | [0 · 0, 11 · 0] | [0 · 0, 11 · 4] | [0 · 0, 6 · 1] | | n . . . number of participants with AE, percentages are based on N, Obs . . . number of events p-value (Overall): Fisher-Freeman-Halton test between Groups L, M, H NC . . . not calculable

TABLE 4

Summary of Adverse Events after Challenge at M6 (H2) or M12 (L, M, H1)

Figure 16:
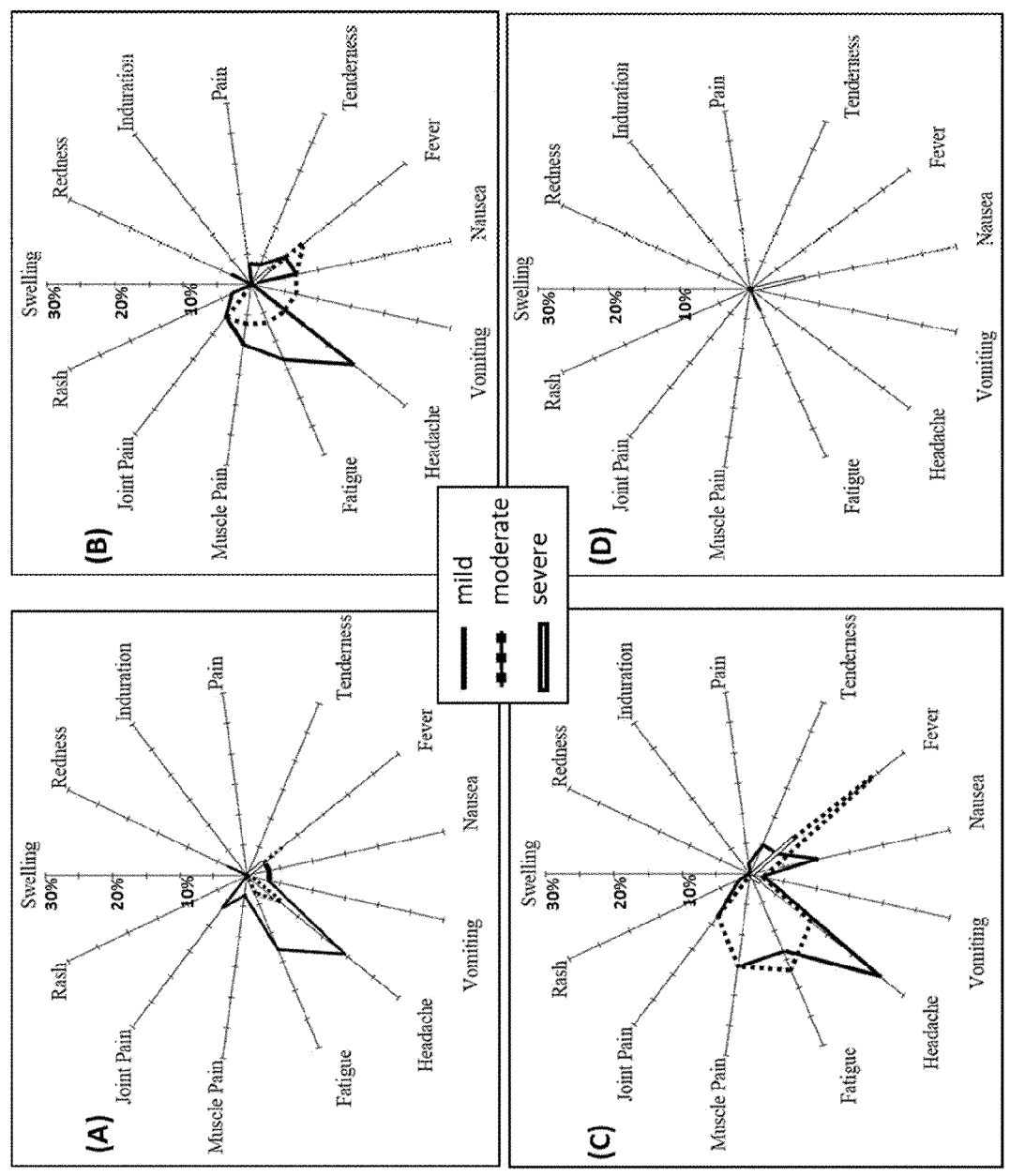
FIG. 16 Radar plot of solicited local and systemic symptoms after single vaccination and revaccination (challenge) including severity grading (Safety Population). Participants with solicited AEs within 14 days after single vaccination with (A) Low dose (Group L; $3.2 \times 10^3$ $TCID_{50}$/0.1 ml) (B) Medium dose (Group M; $3.2 \times 10^4$ $TCID_{50}$/1 ml) and (C) High dose (Groups H1 and H2; $3.2 \times 10^5$ $TCID_{50}$/1 ml); or after high dose revaccination at 6 months (D) group H2 at M6; or 12 months (E) group L at M12; (F) group M at M12; (G) group H1 at M12, by maximum severity. Solicited AEs were graded as mild (Grade 1), moderate (Grade 2) or severe (Grade 3).

| | Statistic | Group L (N = 24) | Group M (N = 23) | Group H1 (N = 21) | Group H2 (N = 26) |
|---|---|---|---|---|---|
| Any AE | n (%) Obs | 3 (12.5) 4 | 0 (0.0) 0 | 4 (19.0) 6 | 5 (19 · 2) 13 |
| | [95% CI] | [4.3, 31.0] | [0.0, 14.3] | [7.7, 40.0] | [8 · 5, 37 · 9] |
| Any related AE | n (%) Obs | 1 (4.2) 1 | 0 (0.0) 0 | 3 (14.3) 4 | 2 (7 · 7) 3 |
| | [95% CI] | [0.7, 20.2] | [0.0, 14.3] | [5.0, 34.6] | [2 · 1, 24 · 1] |
| Any severe AE | n (%) Obs | 0 (0.0) 0 | 0 (0.0) 0 | 0 (0.0) 0 | 2 (7 · 7) 2 |
| | [95% CI] | [0.0, 13.8] | [0.0, 14.3] | [0.0, 15.5] | [2 · 1, 24 · 1] |
| Any related severe AE | n (%) Obs | 0 (0.0) 0 | 0 (0.0) 0 | 0 (0.0) 0 | 2 (7 · 7) 2 |
| | [95% CI] | [0.0, 13.8] | [0.0, 14.3] | [0.0, 15.5] | [2 · 1, 24 · 1] |
| Any SAE | n (%) Obs | 0 (0.0) 0 | 0 (0.0) 0 | 0 (0.0) 0 | 0 (0 · 0) 0 |
| | [95% CI] | [0.0, 13.8] | [0.0, 14.3] | [0.0, 15.5] | [0 · 0, 12 · 9] |
| Any related SAE | n (%) Obs | 0 (0.0) 0 | 0 (0.0) 0 | 0 (0.0) 0 | 0 (0 · 0) 0 |
| | [95% CI] | [0.0, 13.8] | [0.0, 14.3] | [0.0, 15.5] | [0 · 0, 12 · 9] |
| Any medically attended AE | n (%) Obs | 0 (0.0) 0 | 0 (0.0) 0 | 1 (4.8) 1 | 2 (7 · 7) 3 |
| | [95% CI] | [0.0, 13.8] | [0.0, 14.3] | [0.8, 22.7] | [2 · 1, 24 · 1] |
| Any related medically attended AE | n (%) Obs | 0 (0.0) 0 | 0 (0.0) 0 | 0 (0.0) 0 | 1 (3 · 8) 1 |
| | [95% CI] | [0.0, 13.8] | [0.0, 14.3] | [0.0, 15.5] | [0 · 7, 18 · 9] |
| Any solicited AE | n (%) Obs | 1 (4.2) 1 | 0 (0.0) 0 | 3 (14.3) 4 | 2 (7 · 7) 3 |
| | [95% CI] | [0.7, 20.2] | [0.0, 14.3] | [5.0, 34.6] | [2 · 1, 24 · 1] |
| Any related solicited AE | n (%) Obs | 1 (4.2) 1 | 0 (0.0) 0 | 3 (14.3) 4 | 2 (7 · 7) 3 |
| | [95% CI] | [0.7, 20.2] | [0.0, 14.3] | [5.0, 34.6] | [2 · 1, 24 · 1] |
| Any severe solicited AE | n (%) Obs | 0 (0.0) 0 | 0 (0.0) 0 | 0 (0.0) 0 | 2 (7 · 7) 2 |
| | [95% CI] | [0.0, 13.8] | [0.0, 14.3] | [0.0, 15.5] | [2 · 1, 24 · 1] |
| Any solicited local AE | n (%) Obs | 1 (4.2) 1 | 0 (0.0) 0 | 2 (9.5) 2 | 0 (0 · 0) 0 |
| | [95% CI] | [0.7, 20.2] | [0.0, 14.3] | [2.7, 28.9] | [0 · 0, 12·9] |
| Any solicited systemic AE | n (%) Obs | 0 (0.0) 0 | 0 (0.0) 0 | 1 (4.8) 2 | 2 (7 · 7) 3 |
| | [95% CI] | [0.0, 13.8] | [0.0, 14.3] | [0.8, 22.7] | [2 · 1, 24 · 1] |
| Any severe solicited systemic AE | n (%) Obs | 0 (0.0) 0 | 0 (0.0) 0 | 0 (0.0) 0 | 2 (7 · 7) 2 |
| | [95% CI] | [0.0, 13.8] | [0.0, 14.3] | [0.0, 15.5] | [2 · 1, 24 · 1] |
| Any unsolicited AE | n (%) Obs | 2 (8.3) 3 | 0 (0.0) 0 | 2 (9.5) 2 | 4 (15 · 4) 10 |
| | [95% CI] | [2.3, 25.8] | [0.0, 14.3] | [2.7, 28.9] | [6 · 2, 33 · 5] |
| Any related unsolicited AE | n (%) Obs | 0 (0.0) 0 | 0 (0.0) 0 | 0 (0.0) 0 | 0 (0 · 0) 0 |
| | [95% CI] | [0.0, 13.8] | [0.0, 14.3] | [0.0, 15.5] | [0 · 0, 12 · 9] |
| Any severe unsolicited AE | n (%) Obs | 0 (0.0) 0 | 0 (0.0) 0 | 0 (0.0) 0 | 0 (0 · 0) 0 |
| | [95% CI] | [0.0, 13.8] | [0.0, 14.3] | [0.0, 15.5] | [0·0, 12 · 9] |
| Any AESI | n (%) Obs | 0 (0.0) 0 | 0 (0.0) 0 | 0 (0.0) 0 | 0 (0 · 0) 0 |
| | [95% CI] | [0.0, 13.8] | [0.0, 14.3] | [0.0, 15.5] | [0 · 0, 12 · 9] | n . . . number of participants with AE, percentages are based on N, Obs . . . number of events The local tolerability profile within 14 days after the single vaccination was considered excellent at all dose levels, with less than 7% of vaccinees (4/59 in Group H) reporting any local AE (p-value overall 0.7827). Tenderness was the most common injection site reaction after the single vaccination, affecting more than 5% of subjects (3/59 in Group H) (FIG. 16A-C). No injection site reactions were observed after challenge at Month 6 (FIG. 16D). One mild case each of pain, tenderness and swelling was reported after challenge at Month 12 (FIG. 16 E-G). Notable systemic adverse events included short-term fever, headache, fatigue and muscle pain. Rates of related systemic AEs were significantly lower in the Low and Medium dosage groups compared to the High dosage group (p-value overall 0.0007; pairwise test L vs. H 0.0017; M vs. H 0.0031). Nine individuals experienced ten related severe solicited systemic AEs (Tables 3 and 4), predominantly fever, occurring within two to four days after the single vaccination: one fever case each in the Low and Medium dosage groups and five cases in the High dosage group; and one severe case of headache (H) (Table 5). Following challenge at Month 6 or 12, none of the vaccines experienced fever; two individuals in dose group H2 reported severe nausea after 6 months challenge, one case each of moderate headache and mild joint pain were reported in dose group H1 after 12 months challenge (Table 6).

TABLE 5

Related Solicited Systemic AEs by Symptom within 14 Days after Single Vaccination

| | Statistic | Group L (N = 31) | Group M (N = 30) | Group H (N = 59) | p-value (Overall) |
|---|---|---|---|---|---|
| Fever | | | | | |
| severe (Grade 3) | n (%) Obs | 1 (3 · 2) 1 | 1 (3 · 3) 1 | 5 (8 · 5) 5 | 0 · 6796 |
| | [95% CI] | [0 · 6, 16 · 2] | [0 · 6, 16 · 7] | [3 · 7, 18 · 4] | |
| moderate (Grade 2) | n (%) Obs | 2 (6 · 5) 2 | 3 (10 · 0) 4 | 14 (23 · 7) 14 | 0 · 0894 |
| | [95% CI] | [1 · 8, 20 · 7] | [3 · 5, 25 · 6] | [14 · 7, 36 · 0] | |
| mild (Grade 1) | n (%) Obs | 0 (0 · 0) 0 | 2 (6 · 7) 3 | 3 (5 · 1) 3 | 0 · 5157 |
| | [95% CI] | [0 · 6, 16 · 2] | [1 · 8, 21 · 3] | [1 · 7, 13 · 9] | |

TABLE 5-continued

| | Statistic | Group L (N = 31) | Group M (N = 30) | Group H (N = 59) | p-value (Overall) |
|---|---|---|---|---|---|
| Nausea | | | | | |
| severe (Grade 3) | n (%) Obs | 0 (0 · 0) 0 | 0 (0 · 0) 0 | 0 (0 · 0) 0 | NC |
| | [95% CI] | [0 · 0, 11 · 0] | [0 · 0, 11 · 4] | [0 · 0, 6 · 1] | |
| moderate (Grade 2) | n (%) Obs | 0 (0 · 0) 0 | 1 (3 · 3) 1 | 2 (3 · 4) 2 | 0 · 6158 |
| | [95% CI] | [0 · 0, 11 · 0] | [0 · 6, 16 · 7] | [0 · 9, 11 · 5] | |
| mild (Grade 1) | n (%) Obs | 1 (3 · 2) 1 | 2 (6 · 7) 2 | 6 (10 · 2) 6 | 0 · 5509 |
| | [95% CI] | [0 · 6, 16 · 2] | [1 · 8, 21 · 3] | [4 · 7, 20 · 5] | |
| Vomiting | | | | | |
| severe (Grade 3) | n (%) Obs | 0 (0 · 0) 0 | 0 (0 · 0) 0 | 0 (0 · 0) 0 | NC |
| | [95% CI] | [0 · 0, 11 · 0] | [0 · 0, 11 · 4] | [0 · 0, 6 · 1] | |
| moderate (Grade 2) | n (%) Obs | 0 (0 · 0) 0 | 1 (3 · 3) 1 | 1 (1 · 7) 1 | 0 · 7438 |
| | [95% CI] | [0 · 0, 11 · 0] | [0 · 6, 16 · 7] | [0 · 3, 9 · 0] | |
| mild (Grade 1) | n (%) Obs | 1 (3 · 2) 1 | 0 (0 · 0) 0 | 1 (1 · 7) 1 | 1 · 0000 |
| | [95% CI] | [0 · 6, 16 · 2] | [0 · 0, 11 · 4] | [0 · 3, 9 · 0] | |
| Headache | | | | | |
| severe (Grade 3) | n (%) Obs | 0 (0 · 0) 0 | 0 (0 · 0) 0 | 1 (1 · 7) 1 | 1 · 0000 |
| | [95% CI] | [0 · 0, 11 · 0] | [0 · 0, 11 · 4] | [0 · 3, 9 · 0] | |
| moderate (Grade 2) | n (%) Obs | 2 (6 · 5) 2 | 1 (3 · 3) 1 | 7 (11 · 9) 7 | 0 · 4793 |
| | [95% CI] | [1 · 8, 20 · 7] | [0 · 6, 16 · 7] | [5 · 9, 22 · 5] | |
| mild (Grade 1) | n (%) Obs | 5 (16 · 1) 5 | 6 (20 · 0) 6 | 14 (23 · 7) 15 | 0 · 7364 |
| | [95% CI] | [7 · 1, 32 · 6] | [9 · 5, 37 · 3] | [14 · 7, 36 · 0] | |
| Fatigue | | | | | |
| severe (Grade 3) | n (%) Obs | 0 (0 · 0) 0 | 0 (0 · 0) 0 | 0 (0 · 0) 0 | NC |
| | [95% CI] | [0 · 0, 11 · 0] | [0 · 0, 11 · 4] | [0 · 0, 6 · 1] | |
| moderate (Grade 2) | n (%) Obs | 1 (3 · 2) 1 | 1 (3 · 3) 1 | 10 (16 · 9) 10 | 0 · 0725 |
| | [95% CI] | [0 · 6, 16 · 2] | [0 · 6, 16 · 7] | [9 · 5, 28 · 5] | |
| mild (Grade 1) | n (%) Obs | 4 (12 · 9) 4 | 4 (13 · 3) 4 | 8 (13 · 6) 8 | 1 · 0000 |
| | [95% CI] | [5 · 1, 28 · 9] | [5 · 3, 29 · 7] | [7 · 0, 24 · 5] | |
| Muscle Pain | | | | | |
| severe (Grade 3) | n (%) Obs | 0 (0 · 0) 0 | 0 (0 · 0) 0 | 0 (0 · 0) 0 | NC |
| | [95% CI] | [0 · 0, 11 · 0] | [0 · 0, 11 · 4] | [0 · 0, 6 · 1] | |
| moderate (Grade 2) | n (%) Obs | 0 (0 · 0) 0 | 1 (3 · 3) 1 | 9 (15 · 3) 9 | 0 · 0222 |
| | [95% CI] | [0 · 0, 11 · 0] | [0 · 6, 16 · 7] | [8 · 2, 26 · 5] | |
| Pairwise tests | vs. M | 0 · 4918 | · · · | · · · | |
| | vs. H | 0 · 0249 | 0 · 1548 | · · · | |
| mild (Grade 1) | n (%) Obs | 1 (3 · 2) 1 | 3 (10 · 0) 3 | 9 (15 · 3) 9 | 0 · 2227 |
| | [95% CI] | [0 · 6, 16 · 2] | [3 · 5, 25 · 6] | [8 · 2, 26 · 5] | |
| Joint Pain | | | | | |
| severe (Grade 3) | n (%) Obs | 0 (0 · 0) 0 | 0 (0 · 0) 0 | 0 (0 · 0) 0 | NC |
| | [95% CI] | [0 · 0, 11 · 0] | [0 · 0, 11 · 4] | [0 · 0, 6 · 1] | |
| moderate (Grade 2) | n (%) Obs | 0 (0 · 0) 0 | 1 (3 · 3) 1 | 5 (8 · 5) 5 | 0 · 2685 |
| | [95% CI] | [0 · 0, 11 · 0] | [0 · 6, 16 · 7] | [3 · 7, 18 · 4] | |
| mild (Grade 1) | n (%) Obs | 1 (3 · 2) 1 | 2 (6 · 7) 2 | 5 (8 · 5) 5 | 0 · 8073 |
| | [95% CI] | [0 · 6, 16 · 2] | [1 · 8, 21 · 3] | [3 · 7, 18 · 4] | |
| Rash | | | | | |
| severe (Grade 3) | n (%) Obs | 0 (0 · 0) 0 | 0 (0 · 0) 0 | 0 (0 · 0) 0 | NC |
| | [95% CI] | [0 · 0, 11 · 0] | [0 · 0, 11 · 4] | [0 · 0, 6 · 1] | |
| moderate (Grade 2) | n (%) Obs | 0 (0 · 0) 0 | 0 (0 · 0) 0 | 0 (0 · 0) 0 | NC |
| | [95% CI] | [0 · 0, 11 · 0] | [0 · 0, 11 · 4] | [0 · 0, 6 · 1] | |
| mild (Grade 1) | n (%) Obs | 0 (0 · 0) 0 | 0 (0 · 0) 0 | 1 (1 · 7) 1 | 1 · 0000 |
| | [95% CI] | [0 · 0, 11 · 0] | [0 · 0, 11 · 4] | [0 · 3, 9 · 0] | | n . . . number of participants with AE, percentages are based on N, Obs . . . number of events p-value (Overall): Fisher's exact test for overall differences between groups NC . . . not calculable

TABLE 6

Related Solicited Systemic AEs by Symptom within 14 Days after Challenge at M6 (H2) or M12 (L, M, H1)

| | Statistic | Group L (N = 24) | Group M (N = 23) | Group H1 (N = 21) | Group H2 (N = 26) | p-value (L vs. M vs. H1) |
|---|---|---|---|---|---|---|
| Fever | | | | | | |
| severe (Grade 3) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| moderate (Grade 2) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| mild (Grade 1) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| Nausea | | | | | | |
| severe (Grade 3) | n (%) Obs | 0 (0.0) 0 | 0 (0.0) 0 | 0 (0.0) 0 | 2 (7·7) 2 | NC |
| | [95% CI] | [0.0, 13.8] | [0.0, 14.3] | [0.0, 15.5] | [2·1, 24·1] | |
| moderate (Grade 2) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| mild (Grade 1) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| Vomiting | | | | | | |
| severe (Grade 3) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| moderate (Grade 2) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| mild (Grade 1) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| Headache | | | | | | |
| severe (Grade 3) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| moderate (Grade 2) | n (%) Obs | 0 (0.0) 0 | 0 (0.0) 0 | 1 (4.8) 1 | 0 (0·0) 0 | 0.3088 |
| | [95% CI] | [0.0, 13.8] | [0.0, 14.3] | [0.8, 22.7] | [0·0, 12·9] | |
| mild (Grade 1) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| Fatigue | | | | | | |
| severe (Grade 3) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| moderate (Grade 2) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| mild (Grade 1) | n (%) Obs | 0 (0.0) 0 | 0 (0.0) 0 | 0 (0.0) 0 | 1 (3·8) 1 | NC |
| | [95% CI] | [0.0, 13.8] | [0.0, 14.3] | [0.0, 15.5] | [0·7, 18·9] | |
| Muscle Pain | | | | | | |
| severe (Grade 3) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| moderate (Grade 2) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| mild (Grade 1) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| Joint Pain | | | | | | |
| severe (Grade 3) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| moderate (Grade 2) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| mild (Grade 1) | n (%) Obs | 0 (0.0) 0 | 0 (0.0) 0 | 1 (4.8) 1 | 0 (0·0) 0 | 0.3088 |
| | [95% CI] | [0.0, 13.8] | [0.0, 14.3] | [0.8, 22.7] | [0·0, 12·9] | |
| Rash | | | | | | |
| severe (Grade 3) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| moderate (Grade 2) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | |
| mild (Grade 1) | n (%) Obs | 0 (0.0) 0 | 0 (0.0) 0 | 0 (0.0) 0 | 0 (0·0) 0 | NC |
| | [95% CI] | [0.0, 13.8] | [0.0, 14.3] | [0.0, 15.5] | [0·0, 12·9] | | n . . . number of participants with AE, percentages are based on N, Obs . . . number of events Changes in blood cell counts were observed in one third of participants after the single vaccination; most commonly Leukopenia, Neutropenia and Lymphopenia (Table 7). Severe cases were observed across all groups: two cases of neutropenia in the Low and one case in the Medium dose group; two cases of lymphocytopenia in the High dose group. After challenge, no severe cases were reported and a significant reduction in the occurrence of these values in comparison to post single vaccination (paired signed rank test difference at Day 7 after single vs after challenge, p-value <0.0001, Table 7) was observed.

Example 2. Immunogenicity Studies

A. Neutralizing Antibody Titers and Seroprotection Conferred by the Single-Shot CHIKV-Δ5nsP3 Vaccine Secondary objectives of the clinical trial included the immune response after the single vaccination, measured by CHIKV-specific neutralizing antibodies, identification of the optimal dose level of the live-attenuated vaccine candidate, assessment of immunogenicity of CHIKV-Δ5nsP3 after challenge and assessment of antibody persistence up to Month 12 after a single vaccination. Neutralizing antibodies

TABLE 7

Related unsolicited AE up to 28 days after vaccination (Groups L, M and H) and re-vaccination (challenge) (Groups L, M, H1 and H2)

| | | After Vaccination | | | Group H1 (N = 18) | After Re-vaccination — Group H2 (N = 26); Group L (N = 22); Group M (N = 22) | Paired Signed rank test — Group L (N = 22) Day 7 after vaccination vs. Day 7 after re-vaccination | Group M (N = 22) Day 28 after vaccination vs. Day 28 after re-vaccination |
|---|---|---|---|---|---|---|---|---|
| | Statistics | Group L (N = 31) | Group M (N = 30) | Group H (N = 59) | | | | |
| Blood and lymphatic system disorders | n (%) Obs | 6 (19 · 4) 12 | 4 (13 · 3) 7 | 17 (28 · 8) 32 | 0 (0) 0 | | | |
| Leukopenia | n (%) Obs | 6 (19 · 4) 6 | 2 (6 · 7) 2 | 14 (23 · 7) 14 | 0 (0) 0 | | Group H2 < · 0001<br>Group L < · 0001<br>Group M < · 0001<br>Group H1 < · 0001 | 0 · 1751<br>0.9296<br>0.7215<br>0.5218 |
| Neutropenia | n (%) Obs | 5 (16 · 1) 5 | 1 (3 · 3) 3 | 10 (16 · 9) 10 | 0 (0) 0 | | Group H2 < · 0001<br>Group L < · 0001<br>Group M 0 · 0003<br>Group H1 < · 0001 | 0 · 1708<br>0.9765<br>0.7656<br>0.8801 |
| Lymphopenia | n (%) Obs | 1 (3 · 2) 1 | 2 (6 · 7) 2 | 4 (6 · 8) 5 | 0 (0) 0 | | Group H2 < · 0001<br>Group L 0 · 0002<br>Group M < · 0001<br>Group H1 < · 0001 | 0 · 8339<br>0.8831<br>0.2870<br>0.6995 | n . . . number of participants with AE, percentages are based on N, Obs . . . number of events Plasma and urine samples were screened for viremia and viral shedding by PCR as described above. Viremia peaked at Day 3 post immunization in all groups, with the highest mean genome copy equivalent (GCE) value in Group H ($2.3 \times 10^5$ GCE/mL). GCE values in Groups L and M were considerably lower, reaching mean titers of $7.4 \times 10^4$ and $8.9 \times 10^4$ GCE/mL, respectively. Seven days after a single vaccination, the numbers of subjects who showed reportable viremia results were notably decreased in all study arms, with mean values of plasma viral RNA ranging from 8814.0 GCE/mL (Group L) to 27,028.0 GCE/mL (Group H). No subject in any dose arm showed are portable viremia result on Day 14 (FIG. 17A). No viremia was detected after challenge at Day 180 or Month 12 (FIG. 17B). Urinary shedding was detected in a single subject from Group L at Day 7 following vaccination ($1.1 \times 10^4$ GCE/mL) (FIG. 18A) and was not detected at all after challenge at Day 180 or Month 12 (FIG. 18B).

Post-hoc analyses on solicited AEs were performed in order to separate AEs arising before and after re-vaccination. In addition, a statistical comparison of rates of abnormal lymphocyte, neutrophil, and leukocyte counts between 7 and 28 days after single and any re-vaccination was performed.

to the vaccine were evaluated using a microneutralization assay ($\mu$NT), which is based on a colorimetric CPE readout. Briefly, equal volumes of serial two-fold dilutions of serum samples were mixed with CHIKV-Δ5nsP3 (at a concentration resulting in 100% CPE) and incubated for 1-2 h at 37° C., prior to transfer onto Vero cells plated in 96 well plates. After several days, inhibition of Vero cell infection was observed by assessing cell viability. The neutralizing titer is defined as the reciprocal serum dilution which induces 50% protection from cell death ($\mu$NT$_{50}$) compared with the virus control lacking neutralizing antibody. Titers below the quantification limit ($\mu$NT$_{50}$<20) were given the value of 10. Seroconversion was defined as reaching a CHIKV-specific neutralizing antibody titer of at least 20 for baseline seronegative subjects; i.e., $\mu$NT$_{50}$≥20.

The immunogenicity analyses were a comparison of the Geometric Mean Titers (GMTs) and Seroconversion Rates (SCRs) in the per-protocol (PP) population between the dose Groups L, M and H, at Day 28 (i.e. 28 days after vaccination) by ANOVA (factors dose group covariate study site). In addition, GMTs and Geometric Mean Fold Increases (GMFIs) were compared overall and pair-wise (Tukey's HSD test) between dose groups at all time points. All analyses were done in SAS (Version 9.3).

All three vaccine dosages were highly immunogenic after a single vaccination. At 14 days after the single vaccination, 100% of subjects in all dosage groups seroconverted. (Seroconversion was defined as subjects achieving a CHIKV-specific neutralizing antibody titer of at least 20 [$\mu NT_{50} \geq 20$]). Furthermore, seroconversion rates in all dosage groups were sustained until Month 12 (FIG. 19A). At least a 16-fold increase in antibody titers at Day 28 was observed in 96.3% or more subjects in all dosage groups. By Day 28, the highest CHIKV-specific neutralizing GMTs ranged from 592.6 to 686.9, representing a more than 60-fold increase in titers over baseline (FIG. 19B). Peak measured titers of individuals reached up to 10,240 (Groups M and H).

A lack of an anamnestic response, i.e., a booster effect of the challenge dose, in 100%, 100%, 94.4% and 96.2% of subjects, in Groups L, M, H1 and H2, respectively, was observed following challenge, indicating sterilizing immunity as characterized by a less than or equal to a four-fold rise in antibody titers as compared to pre-challenge titers (FIG. 20A and Table 8). Prior to challenge, the Group H2 GMT persisted at 452.5 (range 40-2560) and remained unchanged 28 days post challenge at 490.2 (range 80-2560) (FIG. 20B). Similarly, 28 days after challenge at Month 12 (Month 13), antibody levels in Groups L, M and H1 remained the same as prior to challenge (FIG. 20B).

Figure 22:
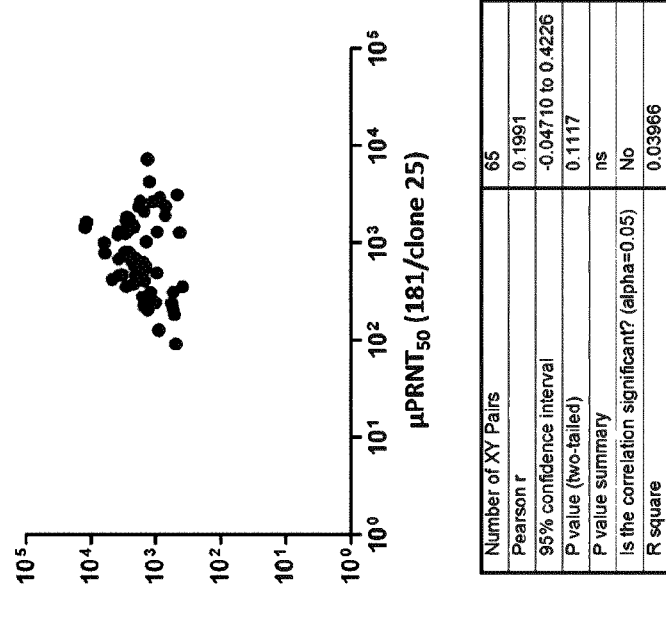
FIG. 22 (A) Correlation of neutralization titers of a panel of 111 CHIKV-Δ5nsP3 phase 1 sera from different time points tested in $\mu NT$ against the vaccine strain CHIKV-Δ5nsP3 (based on the La Reunion strain (LR2006-OPY1) of the East Central South African (ECSA) genotype) and in $\mu PRNT$ against the attenuated CHIKV strain 181/clone 25 of the Asian genotype. Correlation of titers was calculated by Pearson correlation coefficient using all samples with titers $\geq LLOQ$ in both assays (n=75) (Only samples with positive titers were shown.) (B) Correlation of neutralization titer of CHIKV-Δ5nsP3 sera tested in $\mu PRNT$ against CHIKV strain 181/clone 25 of the Asian genotype and CHIKV total IgG ELISA titer (based on viral proteins C, E1 and E2 from West African strain 37997). Correlation of titers was calculated by Pearson correlation coefficient using all samples with titers $\geq LLOQ$ in both assays (n=65) (Only positive titers were shown in the analysis.)

$\Delta 5 nsP3$, neutralizing antibody levels obtained should be well above the surrogate endpoint indicative of protection. Microneutralization PRNT Titers Against Asian CHIKV Strain Suggest Robust Cross-Neutralization Elicited by the CHIKV-$\Delta 5 nsP3$ Vaccine For assessment of cross-neutralizing activity of antibodies elicited by the CHIKV-$\Delta 5 nsP3$ vaccine, a panel of sera from the clinical study from different time points were also tested in a $\mu$PRNT assay for neutralizing capacity against the attenuated heterologous CHIKV strain 181/clone 25 of the Asian genotype. A total of 111 single sera (including 37 pre-vaccination samples) and 5 human serum pools associated with VLA1553-101 study were tested. One $\mu$PRNT result was invalid due to the sample crossing the 50% neutralization threshold twice. The correlation between positive titers (n=75) measured by $\mu$NT and $\mu$PRNT was calculated using the Pearson correlation coefficient. As shown in FIG. 22, there was a highly statistically significant correlation of the neutralization titers of sera tested against the vaccine strain CHIKV-$\Delta 5 nsP3$ (del5nsP3), based on LR2006-OPY1 of the East Central South African (ECSA) genotype and CHIKV strain 181/clone 25 of the Asian genotype. It was observed that antibodies induced by the CHIKV-$\Delta 5 nsP3$ vaccine also efficiently neutralized the 181/clone 25 Asian CHIKV strain. Furthermore, neutralizing antibody titer values against both strains were highly similar

TABLE 8

Rates of participants within ≤4-Fold Increase in Neutralizing Antibody Titer 28 days after Challenge at Month 6 and Month 12.

| Statistics | | Group L (N = 23) | Group M (N = 23) | Group H1 (N = 20) | Group H2 (N = 26) |
|---|---|---|---|---|---|
| Reaching <= 4-fold increase | n/N (%) [95% CI] | 22/22 (100) [85.1, 100] | 22/22 (100) [85.1, 100] | 17/18 (94.4) [74.2, 99.0] | 25/26 (96 · 2) [81.1, 99 · 3] | n . . . number of participants

Setting the seroprotective threshold When transposing the seroprotective threshold established by Yoon et al. 2015 (supra) to the results of the current study, a titer of >1:10 is achieved by Day 14 in 100% of the subjects. Since the PRNT assay used by Yoon et al. and the microneutralization assay used within our study are based on the same principle, albeit in a different format and tested against different viruses, results are not directly comparable. As discussed herein, the PRNT determines virus neutralization by reduction of plaques using the attenuated CHIKV strain 181/clone 25, whereas the $\mu$NT determines neutralization of the attenuated CHIKV-$\Delta 5 nsP3$ by reduction of virus-induced cytopathic effect. But even using the conservative seroprotective threshold of $\mu NT_{50} \geq 20$ as applied in the current Phase 1 study, all subjects developed neutralizing antibody titers by Day 14, which were sustained throughout Month 12 following a single vaccination (FIG. 19A). Stressing this even further by using an unlikely seroprotection threshold titer of $\mu NT_{50} \geq 40$ to $\geq 80$, still nearly 100% of subjects across the different doses would be protected after a single vaccination with CHIKV-$\Delta 5 nsP3$ by Day 14 (FIGS. 21A and 21B). When applying even an unreasonably high threshold titer of $\mu NT_{50} \geq 160$, greater than 90% of subjects across all doses would be protected after a single vaccination with CHIKV-$\Delta 5 nsP3$ at least until Month 12 (FIG. 21C). Based on the high and persisting geometric mean antibody titers elicited by the single-shot live-attenuated CHIKV vaccine CHIKV-in spite of being obtained using different assay formats ($\mu$NT v. $\mu$PRNT). This data strongly suggests that the CHIKV-$\Delta 5 nsP3$ vaccine may confer protection against more than one strain of CHIKV.

While cross-neutralization between different CHIKV genotypes has already been shown in the literature, the results obtained during the feasibility study provided further insight into the cross-neutralizing ability of the CHIKV-$\Delta 5 nsP3$-induced antibodies. Due to differences in assay systems, slight differences in the reported results were nevertheless expected. To support the results obtained from the $\mu$PRNT, anti-CHIKV total IgG antibodies were quantified by ELISA, using a CHIKV virus-like particle (E1, E2 and C1 proteins from West African strain 37997) and results were compared.

Methodology

In the course of clinical development, serum samples selected from the current study were tested using a microneutralization test ($\mu$NT) which measured the neutralization of CHIKV-$\Delta 5 nsP3$, a micro-plaque reduction neutralization test ($\mu$PRNT) which measured neutralization of 181/clone 25 CHIKV and a Chikungunya virus-like particle (VLP)-based IgG ELISA based on the 37997 West African 37997 CHIKV strain. The purified CHIKV virus-like particles (VLPs) for ELISA comprised viral proteins C, E1 and E2 from the West African strain. Serum samples were selected based on neutralization titer obtained during clinical testing to span the titer range and dependent on sample availability.

A panel of 111 CHIKV-Δ5nsP3 human serum samples were included in this comparability study. All three assays were compared in terms of correlation of results and assay characteristics.

Comparison of CHIKV μNT, μPRNT and IgG ELISA

A sub-set of the 111 clinical serum samples were analyzed in μNT, μPRNT and ELISA assays. The correlation between log-transformed titers measured with μNT, μPRNT and ELISA was calculated using the Pearson correlation coefficient (Pearson r), where a value of "1" indicates total positive linear correlation and a value of "0" indicates no linear correlation. Samples with titers below the lower limit of quantification (LLOQ) as well as positive controls were excluded from the correlation analysis. As shown in FIG. 22A, the value obtained for Pearson r with regard to μNT and μPRNT was 0.6724, indicating a moderately strong positive correlation. Moreover, the fact that titers obtained with μPRNT and μNT were comparable indicates a cross-protective ability of CHIKV-Δ5nsP3 against the Asian lineage of CHIKV (181/clone 25).

By contrast, the Pearson r value obtained for μPRNT and ELISA results was 0.1991, indicating only a weak positive correlation (see FIG. 22B). This finding is also reflected in the narrower distribution of titers measured by ELISA compared to titers measured with μPRNT. Presumably, functional differences of CHIKV antibodies, which become apparent in neutralization assays, are not detectable by ELISA. While ELISA measures only total CHIKV-specific IgG antibodies, μPRNT detects CHIKV-neutralizing antibodies of all isotypes. Nevertheless, all samples with positive ELISA titers also showed positive μPRNT titers, an observation supporting a predictive value of ELISA in anti-CHIKV immune responses. All post-vaccination samples from day 14 and later tested positive in ELISA. As CHIKV strains derived from different CHIKV lineages than the vaccine strain CHIKV-Δ5nsP3 (ECSA) were employed in both μPRNT (strain 181/clone 25 Asian) and ELISA (West African strain 37997), the ability of CHIKV-Δ5nsP3 to induce to cross-neutralizing antibodies is further supported.

Early seroconversion A total of ten Visit 1B samples (Day 7±1 day post vaccination) from all groups were included in a study to analyze test performance with samples collected during the early phase of the immune response (see Table A1). All of the samples tested had IgG levels below the LOD in the CHIKV IgG ELISA, indicating the absence of CHIKV-specific IgG antibodies at this early time point after vaccination. However, all except for two Visit 1B samples tested positive in μPRNT and all tested positive in μNT assays, due to the presence of CHIKV-neutralizing IgM antibodies at this early time point.

TABLE A1

| ELISA, μPRNT and μNT results for CHIKV-Δ5nsP3 trial sera from visit 1B (day 7 ± 1 post vaccination). | | |
|---|---|---|
| ELISA (ELU/mL) (VLP 37997 WA) | $\mu PRNT_{50}$ (CHIKV 181/ clone 25 Asian) | $\mu NT_{50}$ (CHIKV-Δ5nsP3 ECSA) |
| <14.7 | <10 | 20 |
| <14.7 | 21 | 40 |
| <14.7 | 29 | 20 |
| <14.7 | 14 | 20 |
| <14.7 | 40 | 40 |
| <14.7 | <10 | 20 |
| <14.7 | 30 | 40 |
| <14.7 | 45 | 20 |

TABLE A1-continued

| ELISA, μPRNT and μNT results for CHIKV-Δ5nsP3 trial sera from visit 1B (day 7 ± 1 post vaccination). | | |
|---|---|---|
| ELISA (ELU/mL) (VLP 37997 WA) | $\mu PRNT_{50}$ (CHIKV 181/ clone 25 Asian) | $\mu NT_{50}$ (CHIKV-Δ5nsP3 ECSA) |
| <14.7 | 76 | 40 |
| <14.7 | 31 | 20 |

Patient sera from CHIKV-Δ5nsP3 trial neutralized wild-type CHIKV Serum samples from the clinical trial (n=47 single sera) were analyzed to quantify wild-type chikungunya virus (Indian Ocean/ECSA lineage [La Reunion strain; wt CHIKV-LR] and West African strain; wt CHIKV-WA 3797) neutralizing antibodies. Sera collected at different visits of individual subjects were analyzed by PRNT (see FIG. 23). All post VLA1553-101 vaccination samples obtained at Day 14 or later demonstrated substantial neutralizing activity against both wild-type La Reunion CHIKV and a heterologous strain of the West African lineage.

Overall, the neutralization capacity of a particular serum for the attenuated CHIKV-Δ5nsP3 strain as assessed by μNT correlated well with its neutralization capacity for two wild-type CHIKV strains as assessed by PRNT. The results not only demonstrated the cross-neutralizing capacity of the CHIKV-Δ5nsP3 vaccine, but also showed the comparability of titer values obtained using the μNT assay and the PRNT assay.

B. GMT Values from CHIKV-Δ5nsP3 Clinical Trial Sera and Convalescent Human Sera Comparable GMTs conferred by natural exposure to CHIKV Antibodies conferred by natural infection are hypothesized to provide life-long protection against CHIKV fever (Galatas, et al. and Nitatpattana, et al.; supra); therefore, the μNT titers observed in the present clinical samples were compared with neutralizing antibody titers in individuals convalescing from natural infection. Fourteen serum samples from individuals recovered from Chikungunya infection (kindly provided by World Reference Center for Emerging Viruses and Arboviruses (WRCEVA) through the University of Texas Medical Branch (UTMB) or purchased from SeraCare and Biomex) were tested in the CHIKV-Δ5nsP3 μNT assay as used in the current clinical study. The neutralization titers of convalescent sera from all three sources were comparable (see Table A2). Furthermore, titers were similar to those observed after a single vaccination with CHIKV-Δ5nsP3, which reached GMT values up to 2560 at Day 28 in all dose groups.

TABLE A2

| Neutralization titers from convalescent serum samples from naturally-infected patients. | |
|---|---|
| Sample | $\mu NT_{50}$ |
| Sera Care #2 | 640 |
| Sera Care #8 | 1,280 |
| Sera Care #10 | 2,560 |
| Biomex | 1,280 |
| UTMB #1 | 1,280 |
| UTMB #2 | 2,560 |
| UTMB #3 | 2,560 |
| UTMB #4 | 1,280 |

TABLE A2-continued

Neutralization titers from convalescent serum
samples from naturally-infected patients.

| Sample | $\mu NT_{50}$ |
|--------|---------------|
| UTMB #5 | 2,560 |
| UTMB #6 | 5,120 |
| UTMB #7 | 1,280 |
| UTMB #8 | 1,280 |
| UTMB #9 | 1,280 |
| UTMB #10 | 5,120 |

Example 3. CHIKV Freeze Dried (Lyo) Product
Formulation Development

Definitions & Abbreviations

CHIKV Chikungunya virus

CHIKV-Δ5nsP3-inv an immunogenic mixture comprising CHIKV-Δ5nsP3 particles comprising the RNA genome corresponding to the DNA sequence provided by SEQ ID NO: 1 and CHIKV-Δ5nsP3 variants with an RNA genome at least 99% identical to the corresponding DNA sequence provided by SEQ ID NO: 1, but encoding a viral polyprotein having at least one amino acid difference, preferably in the region encoding envelope protein E2 (also referred to herein as CHIKV-Δ5nsP3)

CTMA CTM Analyitics & Development department

CMO Contract Manufacturing Organization

DLS Differential Light Scattering

DP Drug Product comprising CHIKV-Δ5nsP3-inv

DS Drug Substance comprising CHIKV-Δ5nsP3-inv

DSP Down Stream Process mDSC Modulated Differential Scanning Calorimetry

GCE Genome copy equivalents

HEPES (4-(2-hydroxyethyl)-1-piperazineethanesulfonic acid)

PC Polycarbonate

PD Process Development Department

PETG Polyethylene terephthalate glycol-modified

PS Particle Size rHSA Recombinant Human Serum Albumin

RT-qPCR Reverse Transcription—quantitative Polymerase Chain Reaction

SGP Sucrose gradient pool $TCID_{50}$ Tissue culture infectious dose 50%

TRIS Tris(hydroxymethyl)-aminomethane

TTR Technical Transfer Run (non-GMP)

WFI Water for Injection

Materials and Methods

CHIKV Material

CHIKV-Δ5nsP3-inv with SEQ ID: 1 encoding for E2 (SEQ ID NO: 2) (including the other substantial variant CHIKV-Δ5nsP3 encoding for E2 (SEQ ID NO:3, with E1 and other expressed proteins unchanged) was produced in Vero cells and purified according to a processes described elsewhere (see WO2019057793, WO2017109223, WO2017109224). As used herein, CHIKV-Δ5nsP3-inv is also referred to herein as CHIKV-Δ5nsP3, CHIKV candidate.

Relevant experiments were conducted with representative virus material—produced in several lots—with regard to impurity profile and virus seed passage (P3).

TABLE 9

Sucrose Gradient Pool (SGP) material.

| lot# | Description | $\log_{10}$ $TCID_{50}$/mL |
|------|-------------|-------------------|
| 1 | SGP | 9.0 |
| 2 | SGP | 8.8 |
| 3 | SGP | 8.0 |
| 4 | SGP | 8.4 |
| 5 | SGP | 10.0 |
| 6 | SGP | 9.8 |
| 7 | SGP | 10.0 |

$TCID_{50}$ Assay

Virus infectivity was determined by $TCID_{50}$ assay on vero cells. Virus titers were determined on Vero cells using the $TCID_{50}$ assay. Briefly, cells were seeded in microplates and infected with 10-fold serially diluted virus samples in EMEM supplemented with 0.5% FBS and 2 mM glutamine. After a one week incubation at 35° C./5% C02, virus-induced cytopathic effects were monitored and viral titers were calculated according to the Reed and Muench method (Reed, L. J.; Muench, H. A simple method of estimating fifty percent endpoints (1938) The American Journal of Hygiene 27:493-497). Assay control samples were included in each analysis. The assay variability between individual runs was estimated as ±0.3 $\log_{10}$ $TCID_{50}$.

Dynamic Light Scattering (DLS)

Dynamic light scattering (DLS) is a technique that can be used to determine the size distribution profile of biopolymers including viral particles in solution at a size range from 1 nm to approx. 1000 nm. Since this method can be used with the native sample without any pre-treatment (e.g. no chromatography column that might filter out larger multimers/aggregates), a full picture of all particles in solution can be obtained. For DLS measurements a Malvern Zetasizer system was used. CHIKV-Δ5nsP3-inv sucrose gradient pools (~35% sucrose in Tris/NaCl) were analyzed without any pre-treatment (i.e. dilution) assuming a solution viscosity of 6.15 cP and refractive index 1.4. The virus particle refractive index was assumed as 1.45. For accurate measurement the particle concentration should not fall below a certain threshold which also depends on the size of the particles. For CHIKV-Δ5nsP3-inv the most accurate results are obtained for undiluted SGP. A comparison of representative SGP material (SGP pools in Table 9) showed a viral particle diameter of approximately 60 nm for all analyzed SGP samples (data not shown), which correlates to data referenced in literature.

Chemicals

TABLE 10

Chemicals and sources

| Chemical | Manufacturer | Order # | Quality |
|----------|--------------|---------|---------|
| $MgCl_2$ * 6 $H_2O$ | Merck | 105832 | Multi-compendial |
| L-Methionine | AppliChem | A1340, 0100 | Ph. Eur., USP |
| $K_2HPO_4$ dibasic anhydrous | Sigma | RES20765-A7 | Ph. Eur. |
| | MERCK | 105101 | Ph Eur, BP, E 340 |

TABLE 10-continued

| Chemicals and sources | | | |
|---|---|---|---|
| Chemical | Manufacturer | Order # | Quality |
| $KH_2PO_4$ monobasic | Fluka | 04243 | Ph. Eur. |
| | MERCK | 104871 | Multi-compendial |
| Trisodium citrate dihydrate | Sigma | S1804 | Ph. Eur. |
| | Citrique belge | 04 12325 | Multi-compendial |
| | MERCK | 106432 | Eur, BP, JP, USP |
| Sucrose | JT Baker | 4005 | Ph. Eur. |
| | MERCK | 107653 | Multi-compendial |
| rHSA (20% stock solution) Recombumin ® Alpha (RF20-005) | Novozymes | n.a. | Ph. Eur. |
| D-Sorbitol | AppliChem | A2222, 1000 | Ph. Eur., USP-NF |
| WFI | HALIX B.V. | n.a. | Ph. Eur. |

Preparation of Lyo Formulation Buffer

In short, for preparation of e.g. 5 liter formulation buffer the following procedure is applied:

Fill approximately 4.5 L of WFI into a tared glass bottle with a stirring bar

Add all buffer components under stirring:

36.8 g—Trisodium citrate dihydrate 3.13 g di-Potassium Hydrogen Phosphate 0.975 g Potassium di-Hydrogen Phosphate 250 g Sucrose 25 g Sorbitol 7.46 g L-Methionine 5.08 g Magnesium Chloride hexahydrate 2.5 mL recombinant human Albumin (20% solution)

Stir until a clear solution is obtained.

Fill up to the final volume of 5000 mL with WFI.

The density (ρ) of the final solution is 1.025 g/mL (20° C.). If 5000 mL are prepared the final resulting weight is 5125 g.

Freeze Dryers

Lab Scale:

Lyophilization was performed on an AdVantage Pro bench top shelf tray dryer with Intellitronics Control from SP Scientific (USA):

Three shelves (total 2766 cm²)

Shelf temperature: −60 to +60° C.

Lowest condenser temperature: −70° C.

Condenser capacity of 6 L

Stoppering: top-down pneumatic

Intermediate Scale:

Lyophilization at an intermediate scale was performed with a Lyofast 7 freeze drier from IMA (Industria Macchine Automatiche S.p.A., Italy)

Six shelves (total 6.7 m²)

Shelf temperature minimum: −55° C.

Lowest condenser temperature: −75° C.

Condenser Capacity: 148 Kg

Primary Packaging (Vials and Stoppers)

For phase I:

2R Type I Plus® glass vials (Schott AG), FluroTec stoppers (West Pharmaceutical Services)

Intended Primary Packaging for Further Clinical Phases (Lyophilized DP):

2R Type I glass vials (Schott AG), bromobutyl stoppers (West Pharmaceutical Services)

Results

The liquid formulation buffer of Example 4 (herein, below) was chosen as a starting buffer composition for the further development of a lyophilized formulation which would ensure sterile filterability during DS and DP production:

10 mM potassium phosphate 25 mM sodium citrate

5% sucrose 0.01% rHSA pH 7.3

Most analytical data were generated by $TCID_{50}$ assay as this method not only indicates infectivity of the virus but is also used during release and stability testing. In addition, dynamic light scattering (DLS) for evaluation of the particle size and qPCR for total viral particle determination were used. Results shown in all of FIGS. 2-14 were generated using formulations of the high dose of the CHIKV vaccine.

Justification of Buffer Components

In general, the concentration of buffer ions used in freeze-dried and frozen systems must be low enough to prevent concentration effects during the freezing process, but still high enough to provide adequate buffering capacity at the desired pH. Phosphate ions are generally avoided for freeze drying purposes as concentration effects and precipitation during freezing can lead to significant pH shifts, especially at higher concentrations (Sek, D. Breaking old habits: moving away from commonly used buffers in pharmaceuticals 2012 European Pharmaceutical Review https://www.euro-peanpharmaceuticalreview.com/article/13699/breaking-old-habits-moving-away-from-commonly-used-buffers-in-phar-maceuticals/). Therefore Tris, HEPES and Histidine were tested alongside phosphate (4 mM, 5 mM and 10 mM) as alternative buffer components. The influence of these buffering agents on the stability of the lyophilized product in the presence of 10 mM L-methionine and 25 mM sodium citrate was assessed at 37° C., room temperature and 4° C. storage temperature. Overall, phosphate and HEPES buffer (20 mM) showed comparable stability profiles at all investigated temperatures and outperformed the other buffer compositions (data not shown). Therefore, additional experiments were performed for comparison of these two buffers: 5 mM phosphate buffer or 20 mM HEPES, both formulations including 4% Sucrose, 1% Trehalose, 10 mM L-Methionine, 2 mM EDTA), showing no significant differences in stability of the lyo CHIKV formulation over time (data not shown).

Based on the overall results it was decided to keep phosphate as buffering agent (as in the liquid frozen formulation, also together with a citrate buffer), but at the lower concentration of 5 mM to minimize buffer concentration effects and possible pH shifts during freezing.

Phosphate-Citrate Buffer: Liquid formulation buffer development for early clinical phases was aimed at 0.2 μm sterile filterability of CHIK virus during DS and DP manufacturing. A buffer system consisting of phosphate and citrate at pH 7.3 proved to stabilize the viral particle size of CHIKV and guarantees 0.2 μm filterability, which is crucial for aseptic manufacturing. To minimize possible ion concentration effects and to facilitate lyophilization, the final phosphate concentration in the lyo formulation was reduced to 5 mM.

Sucrose

During downstream processing, a sucrose gradient centrifugation is performed for final concentration and polishing of the CHIKV material, resulting in a sucrose concentration of approximately 35% in the sucrose gradient pool (SGP). As sucrose is a well-known stabilizer during freezing of biological material and also serves as a bulking material, it was kept in the formulation buffer for the freeze dried product. Sucrose at 5% has been shown to protect CHIKV during freeze/thaw stress. By subsequent dilution of SGP to DS (currently 1:60) and DP with formulation buffer a final sucrose concentration of 5% is obtained.

Recombinant Human Albumin

The concentration of rHSA was kept constant for the lyophilized product compared to the liquid formulation at a level of 0.01% (0.1 mg/mL). The incorporation of a minimal amount of rHSA is desired to prevent unspecific adsorption to surfaces of containers. Additionally rHSA at this concentration does not adversely affect the sterile filterability of the CHIKV nor the stability of the freeze dried product.

After these initial studies, the basic formulation of the lyophilized formulation ("basic lyo") was:

5 mM potassium phosphate
    25 mM sodium citrate
    5% sucrose
    0.01% rHSA
    pH 7.3

Additional excipients tested for improved stability of the lyo formulation:

D-Sorbitol

Figure 2:
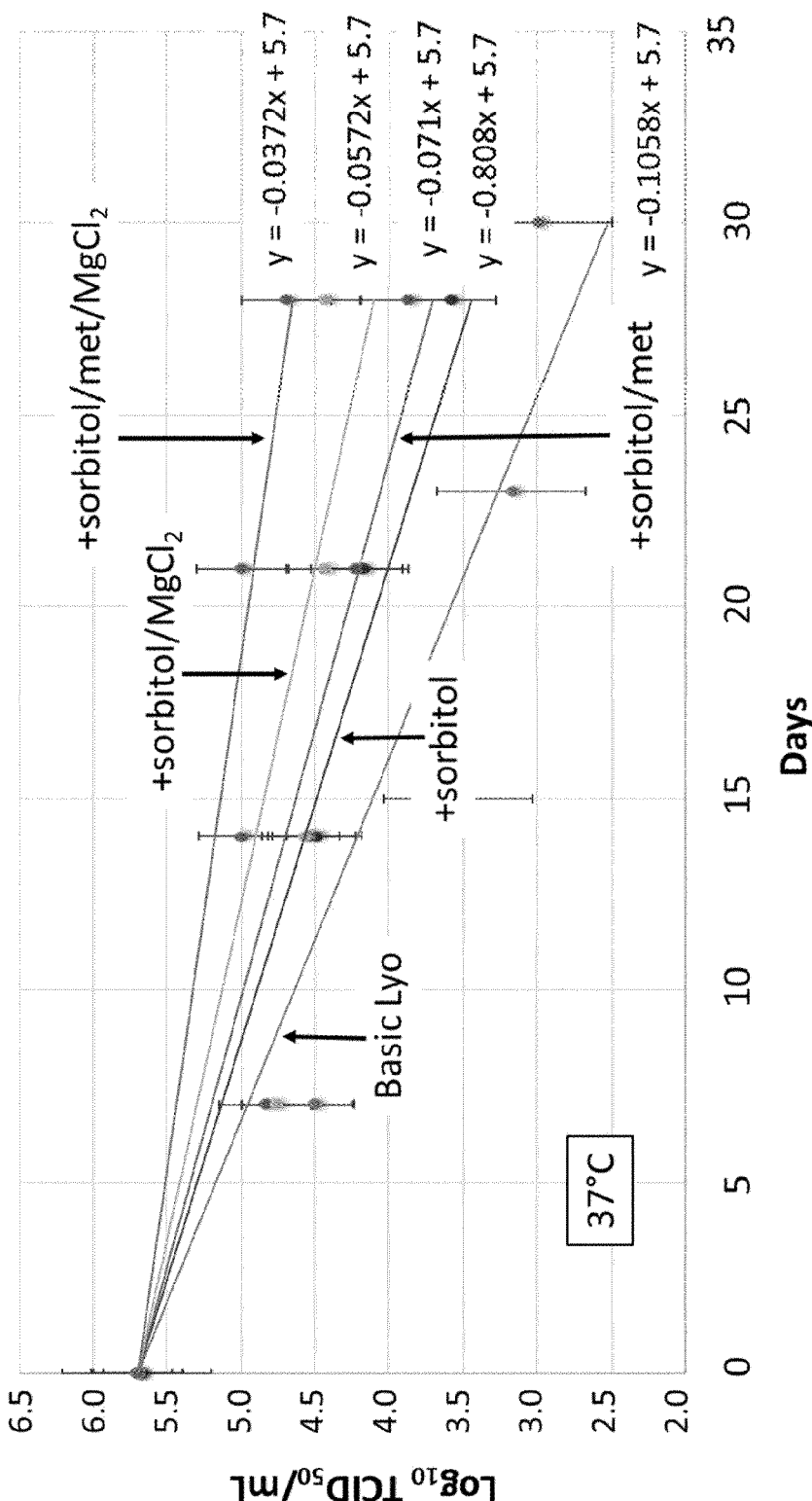
FIG. 2 Effects of sorbitol, magnesium chloride and L-methionine on freeze-dried CHIKV-Δ5nsP3-inv at 37° C. $TCID_{50}$ assay (error bars of ±0.3 log).
Figure 3:
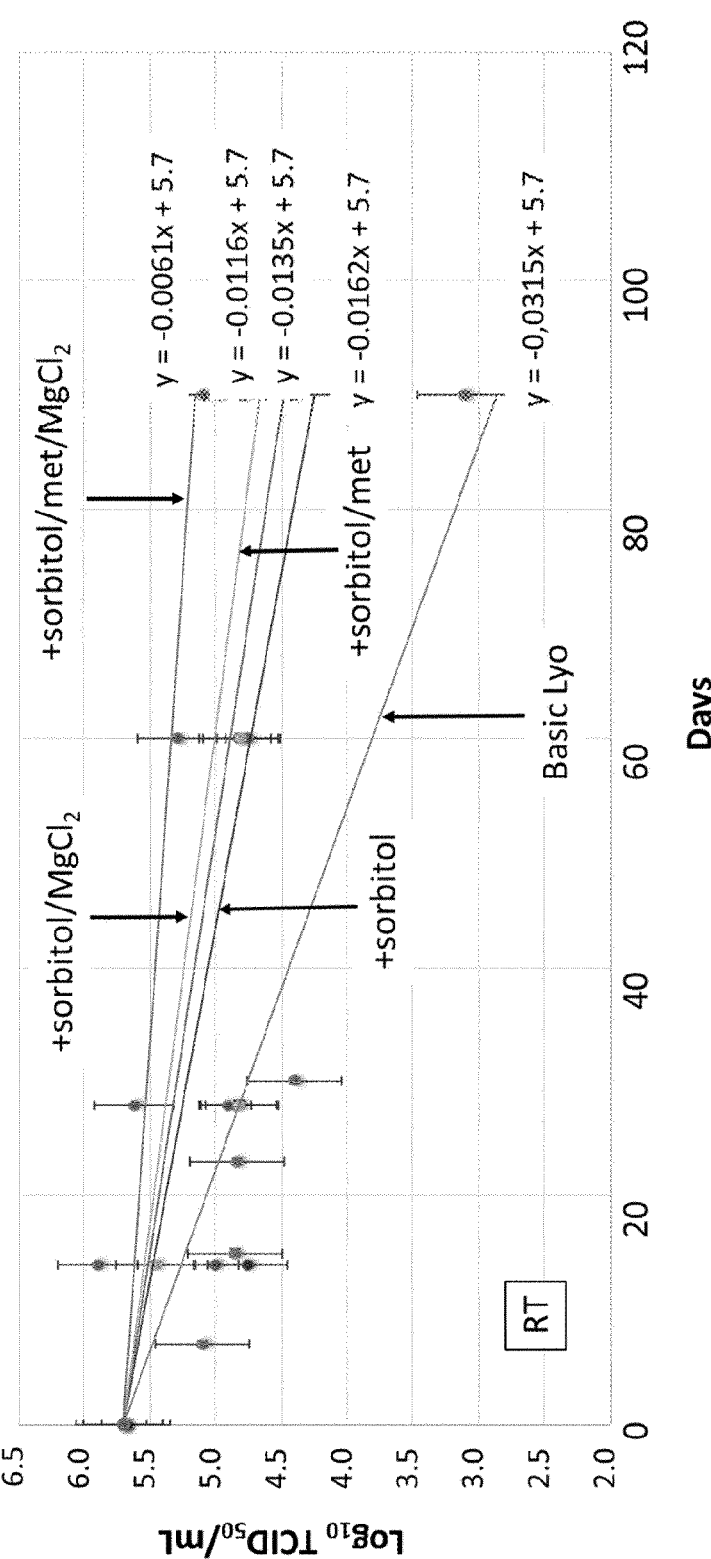
FIG. 3 Effects of sorbitol, magnesium chloride and L-methionine on freeze-dried CHIKV-Δ5nsP3-inv at room temperature. $TCID_{50}$ assay (error bars of ±0.3 log).
Figure 4:
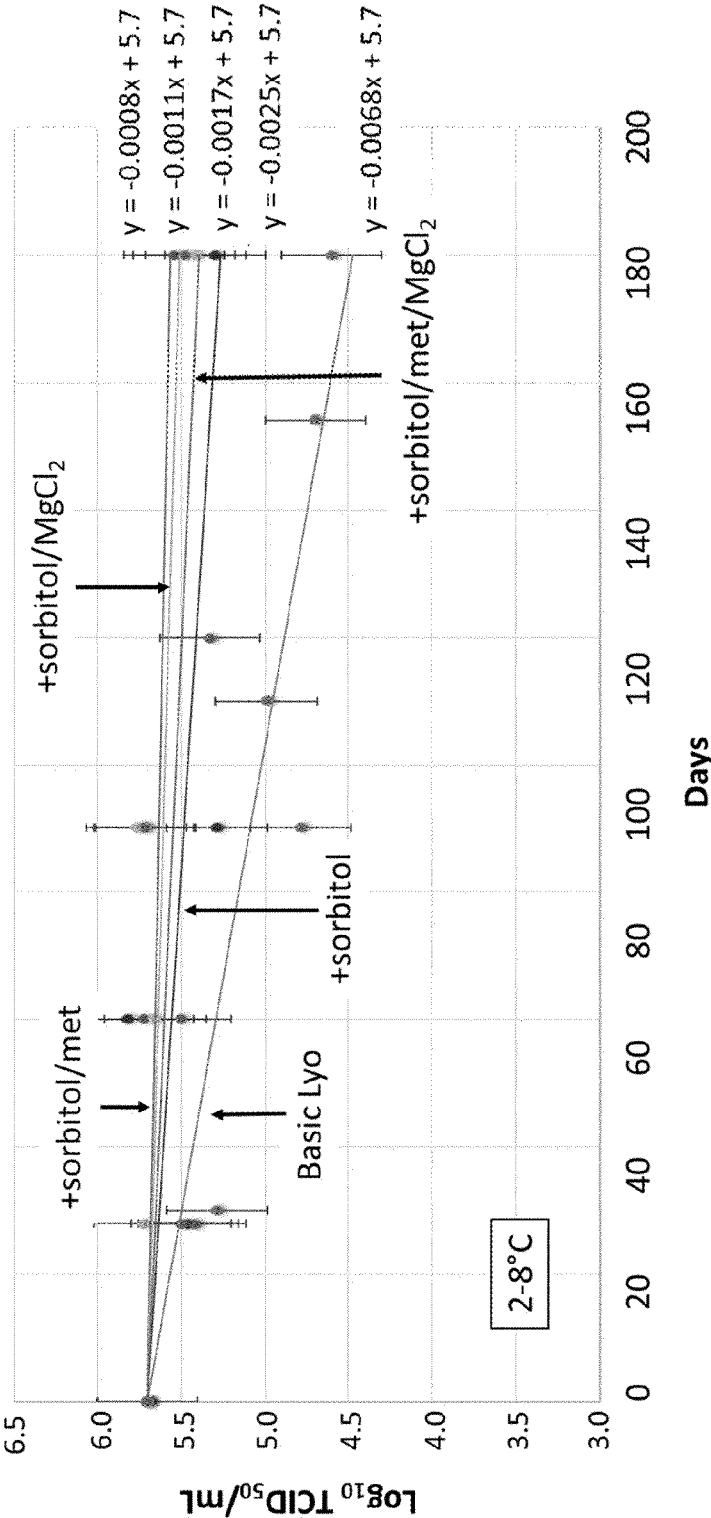
FIG. 4 Effects of sorbitol, magnesium chloride and L-methionine on freeze-dried CHIKV-Δ5nsP3-inv at 2-8° C. $TCID_{50}$ assay (error bars of ±0.3 log).

Lyophilization of CHIKV-Δ5nsP3-inv in the basic lyo buffer showed insufficient stability in the freeze dried state (see FIGS. 2-4). The addition of sorbitol alone exhibited a significant improvement of stability, especially under accelerated storage conditions (37° C., RT; FIGS. 2 and 3, respectively). A positive stabilizing effect of sorbitol on CHIKV was observed for all exploratory formulations tested during development. As sucrose alone already exhibits a rather low collapse temperature ($T_C$) of −32° C. during freeze drying, the concentration of sorbitol ($T_C$−45° C.) was set to 0.5% to prevent an additional significant decrease of the overall $T_C$ but providing significant stabilization of the freeze dried product.

Magnesium Chloride

Magnesium chloride is assumed to stabilize the RNA structure of CHIKV and exhibited a positive effect on infectivity after storage (FIGS. 2-4). It is incorporated into the lyo formulation buffer at a concentration of 5 mM.

L-Methionine

L-Methionine is regarded as an oxidant scavenger applied in protein formulations. When added at a final concentration of 10 mM it increased stability during storage at 2-8° C. (FIG. 4) and more pronounced at accelerated temperatures (37° C., RT; FIGS. 2 and 3, respectively).

Effect of Excipients on CHIKV Stability in the Freeze Dried State

Positive effects the stability of freeze dried CHIKV-Δ5nsP3-inv of addition to the basic lyo formulation of sorbitol (0.5%), magnesium chloride (5 mM) and L-methionine (10 mM) and combinations thereof at various temperatures (37° C., RT and 2-8° C.) are summarized in FIGS. 2-4, respectively (as assessed by $TCID_{50}$ over days of storage).

The one-by-one addition of the respective additives to this basic buffer is indicated in the graphs. As starting point the theoretical $TCID_{50}$ value after dilution to DP concentration (5.7 $\log_{10}$ $TCID_{50}$/mL) was assumed for all formulations.

Compared to lyophilization of CHIKV-Δ5nsP3-inv in basic lyo formulation buffer, a significant stabilization by addition of sorbitol alone and especially in combination with L-methionine and magnesium chloride was observed under accelerated conditions.

At 37° C., the loss of infectivity improved from approximately 3 $\log_{10}$ to 1 $\log_{10}$ per month and at room temperature from approximately 1 $\log_{10}$ to 0.2 $\log_{10}$ per month. When CHIKV-Δ5nsP3-inv was lyophilized in basic lyo formulation buffer without the addition of sorbitol, $MgCl_2$ or L-methionine and stored at 2-8° C. (FIG. 4), a significant difference could be observed (approximately 1 $\log_{10}$ loss after half a year) compared to the other formulations.

Subsequent testing of lyophilized CHIKV was performed in lyophilization buffer (also referred to herein as freeze drying formulation buffer and lyo buffer) as follows:

5 mM potassium phosphate
    25 mM sodium citrate
    5% sucrose
    0.01% rHSA
    5 mM $MgCl_2$
    0.5% D-sorbitol
    10 mM L-methionine
    pH 7.3

Comparison of CHIKV Before and After Freeze Drying

Dynamic Light Scattering (DLS)

Figure 5:
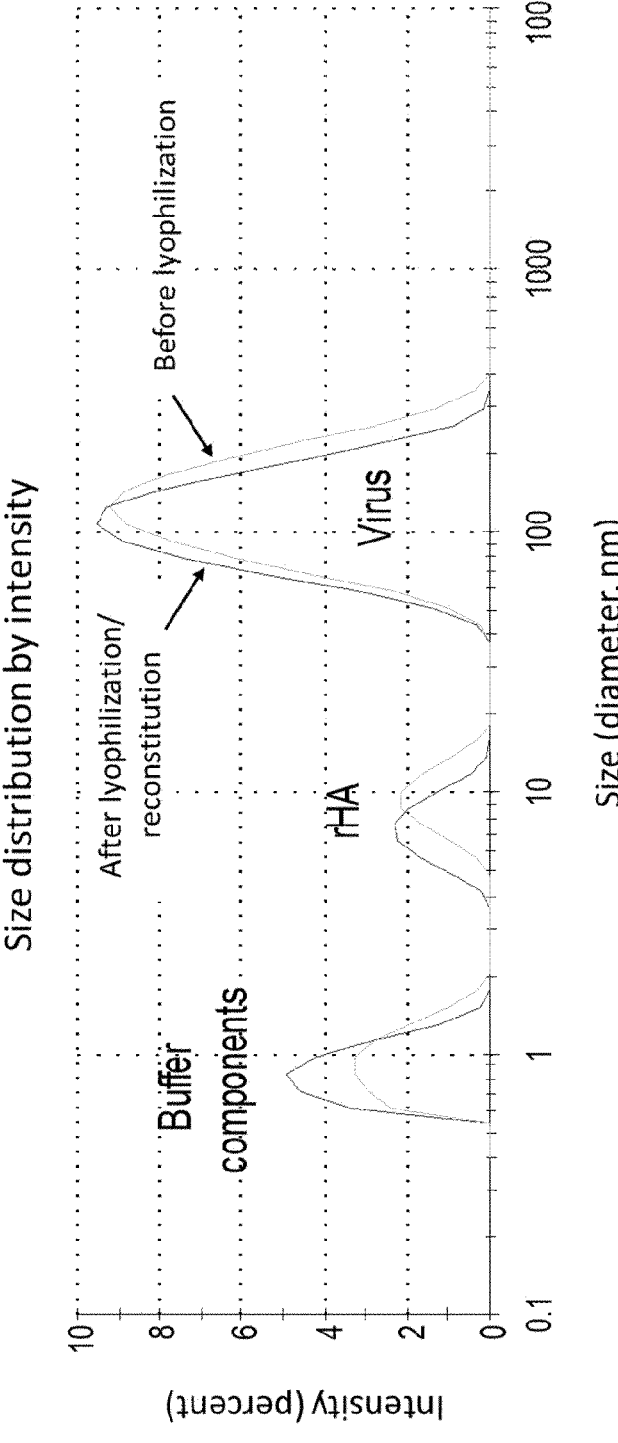
FIG. 5 Overlay of DLS signals obtained from high dose DS before and after lyophilization.

The exact size of CHIKV can only be determined in concentrated samples (e.g. SGP) due to signal interference with buffer excipients (e.g. rHSA) at lower virus content. Comparative results are obtainable for samples diluted in lyo formulation buffer (containing rHSA) as long as the virus concentration is high enough. Therefore, Lot 1 SGP (9.0 $\log_{10}$ $TCID_{50}$/mL) was diluted 1:40 in freeze drying formulation buffer resulting in a virus concentration of approximately 7.4 $\log_{10}$ $TCID_{50}$/mL. This material was measured by DLS both before lyophilization and after lyophilization/reconstitution of the freeze dried virus (FIG. 5). The determined virus size before freeze drying (135 nm) and after reconstitution (118 nm) were comparable.

Plaque Assay RT-qPCR

When propagated in host cells, CHIKV show minor genetic heterogeneities at defined positions in the RNA genomic sequence, resulting in different populations of virus in any given preparation. Some of these defined heterogeneities are characterized by reduced immunogenicity of the virus (e.g., an E168K point mutation in the CHIKV E2 protein). Therefore, it was important to identify any potential change of virus composition due to different stability profiles of the individual viral genetic populations during lyophilization.

Figure 6:
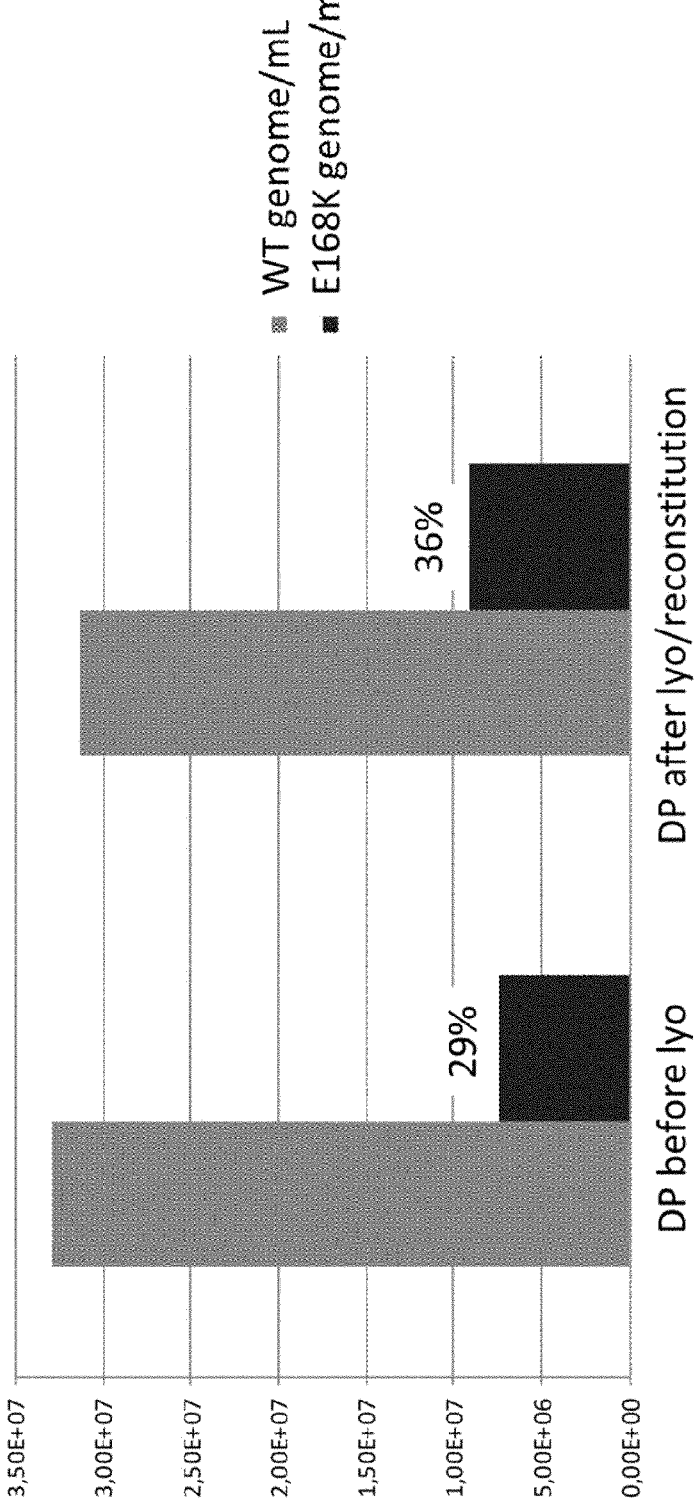
FIG. 6 RT-qPCR data of DP before and after lyophilization. WT sequence in the respective region compared to E168K mutation.

DP with a nominal concentration of 5.7 $\log_{10}$ $TCID_{50}$/mL was prepared from Lot 3 SGP by dilution in lyophilization buffer and subsequent freeze drying. Samples were taken before (5.69 $\log_{10}$ $TCID_{50}$/mL) and after lyophilization (5.61 $\log_{10}$ $TCID_{50}$/mL) and analyzed in a plaque assay to determine plaque morphology (data not shown) and by RT-qPCR for quantification of E168K heterogeneity compared to the wild type sequence of the respective region (FIG. 6). Lyophilization and reconstitution had no substantial effect on the ratio of the two populations.

CHIKV Stability Lyophilized DP
CHIKV Material

Relevant experiments (n=4) summarized in this report were conducted with representative DP material.

Table 11 below summarizes the investigated DP formulations and the CHIKV material used, which included both lab and intermediate scale (TTR) formulations.

TABLE 11

| Residual moisture content of lab and intermediate (technical transfer) scale lyophilized DP. | |
| --- | --- |
| Run | Residual Moisture % |
| Lab Scale Run F59B | 1.7 |
| Lab Scale Run F72 | 1.4 |
| TTR2 intermediate scale | 1.7 |
| TTR3 intermediate scale | 1.6 |

Figure 7:
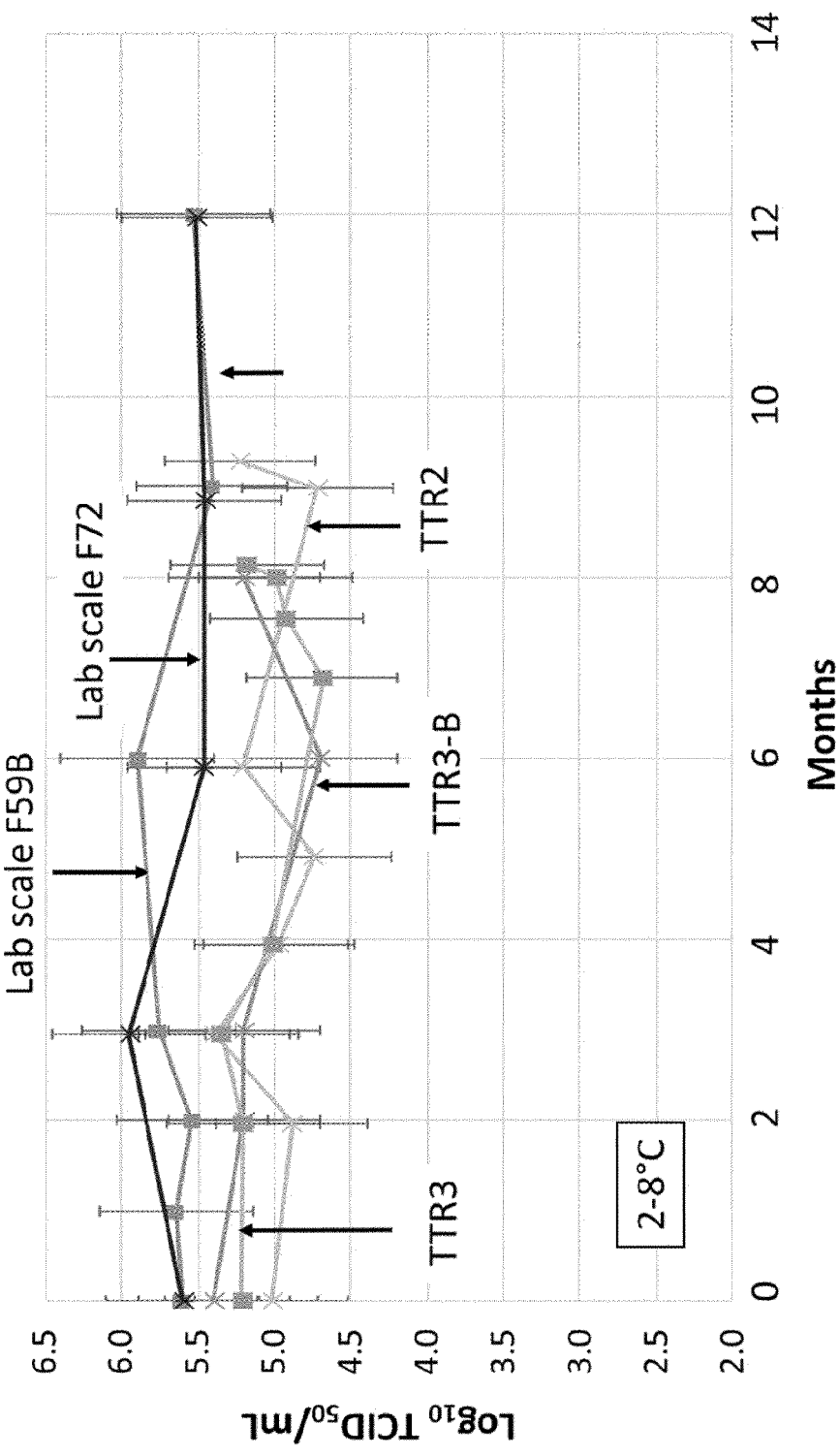
FIG. 7 Stability of CHIKV-Δ5nsP3-inv DP formulations (at lab and intermediate scale) at 2-8° C. Results of $TCID_{50}$ assay (error bars of ±0.5 log).
Figure 24:
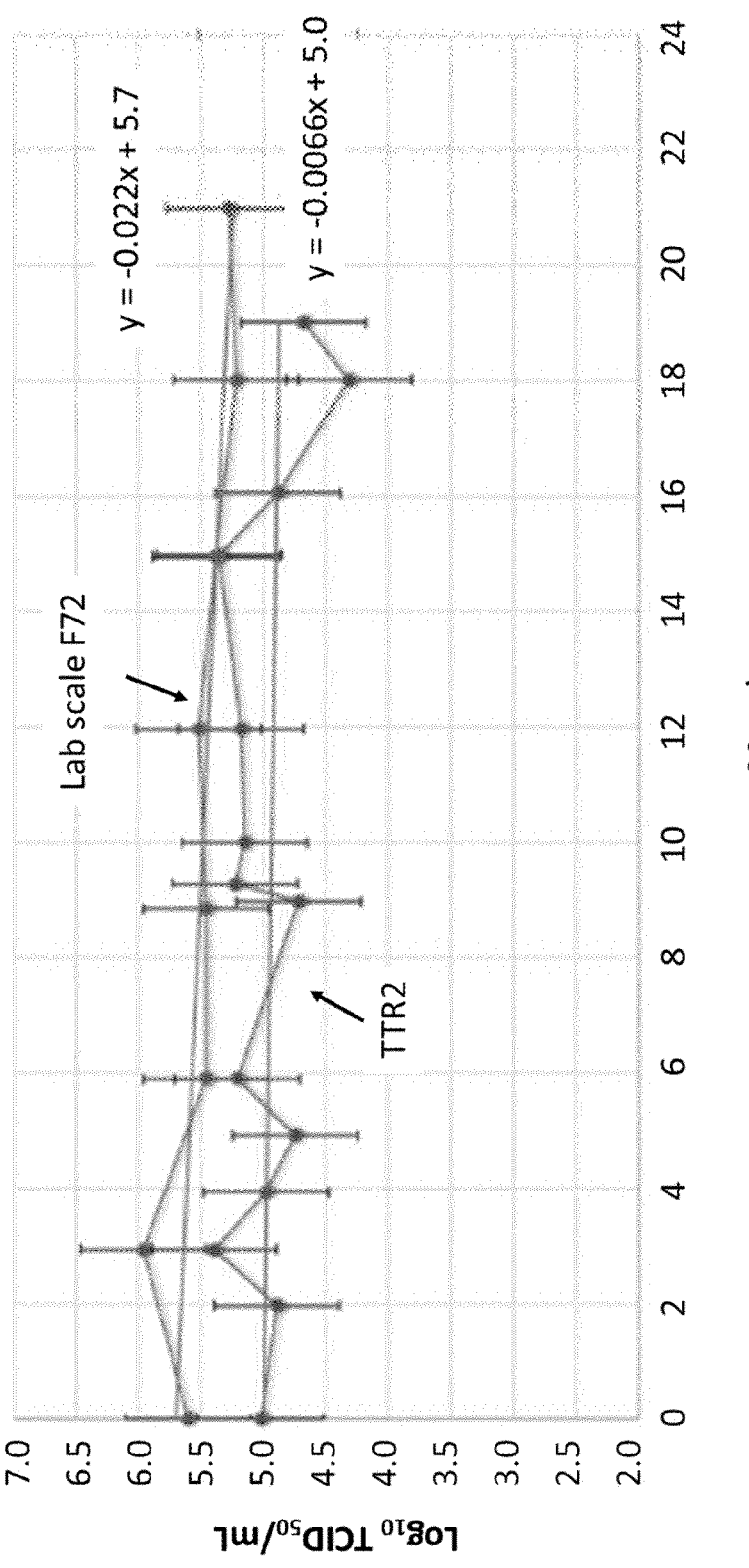
FIG. 24 Stability comparison of lyophilized DP produced at intermediate (technical transfer) and lab scales at 2-8° C. storage up to 19 and 21 months, respectively, as assessed by $TCID_{50}$ at each timepoint directly after reconstitution in WFI.

The standard storage condition of lyophilized CHIKV DP is 2-8° C. FIG. 7 shows stability data of different lots, i.e. TTR2, TTR3, F59B and F72, stored at 2-8° C. Data are shown as $\log_{10}$ TCID$_{50}$/mL values. Longer stability data are available for Lab sample F72 (21 months) and TTR2 (19 months) (see FIG. 24). As expected, the titer loss of the lyophilized formulation at refrigerated temperatures was minimal.

Figure 8:
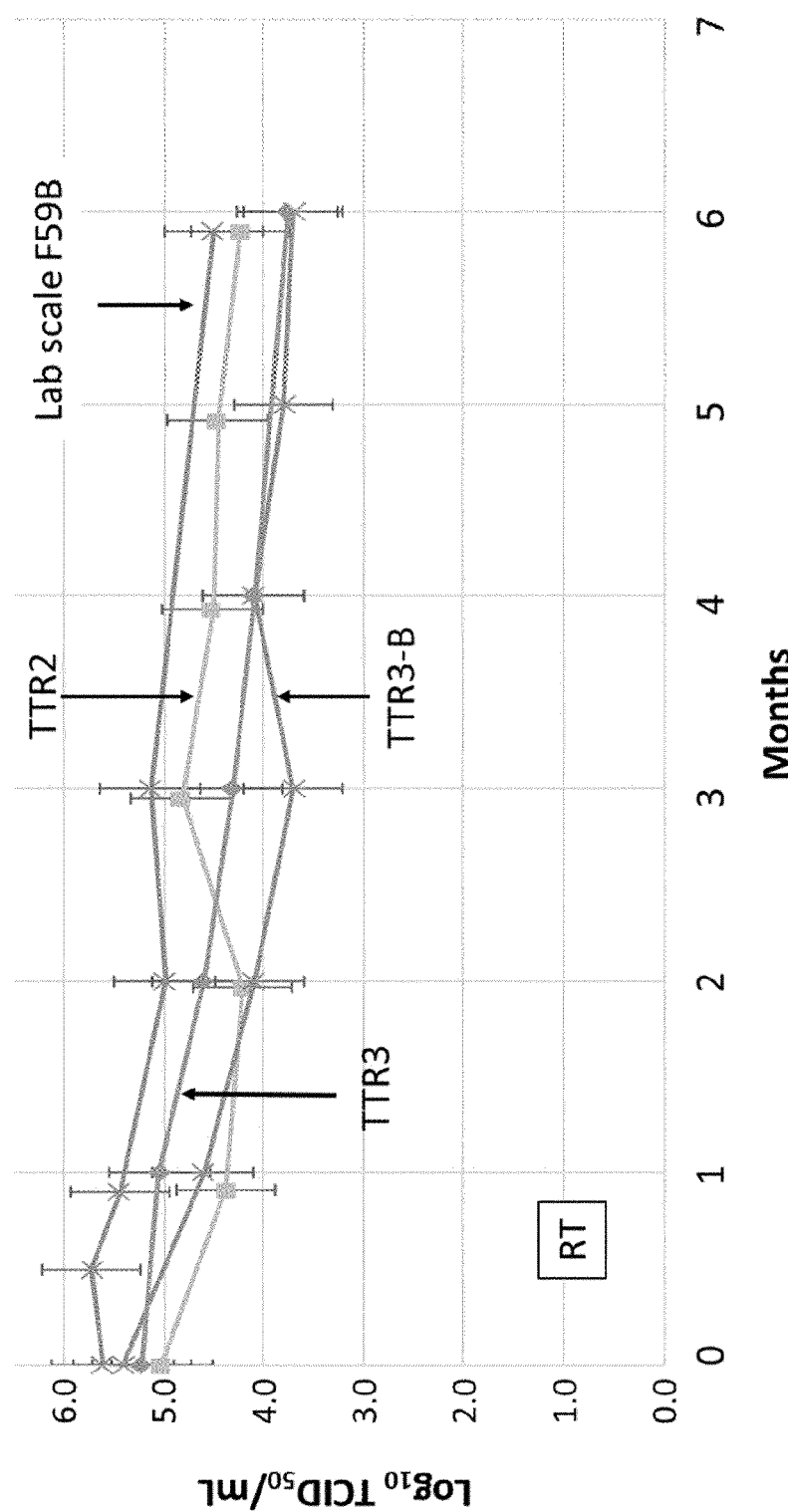
FIG. 8 Stability of CHIKV-Δ5nsP3-inv DP formulations (at lab and intermediate scale) at room temperature. $TCID_{50}$ assay (error bars of ±0.5 log).
Figure 9:
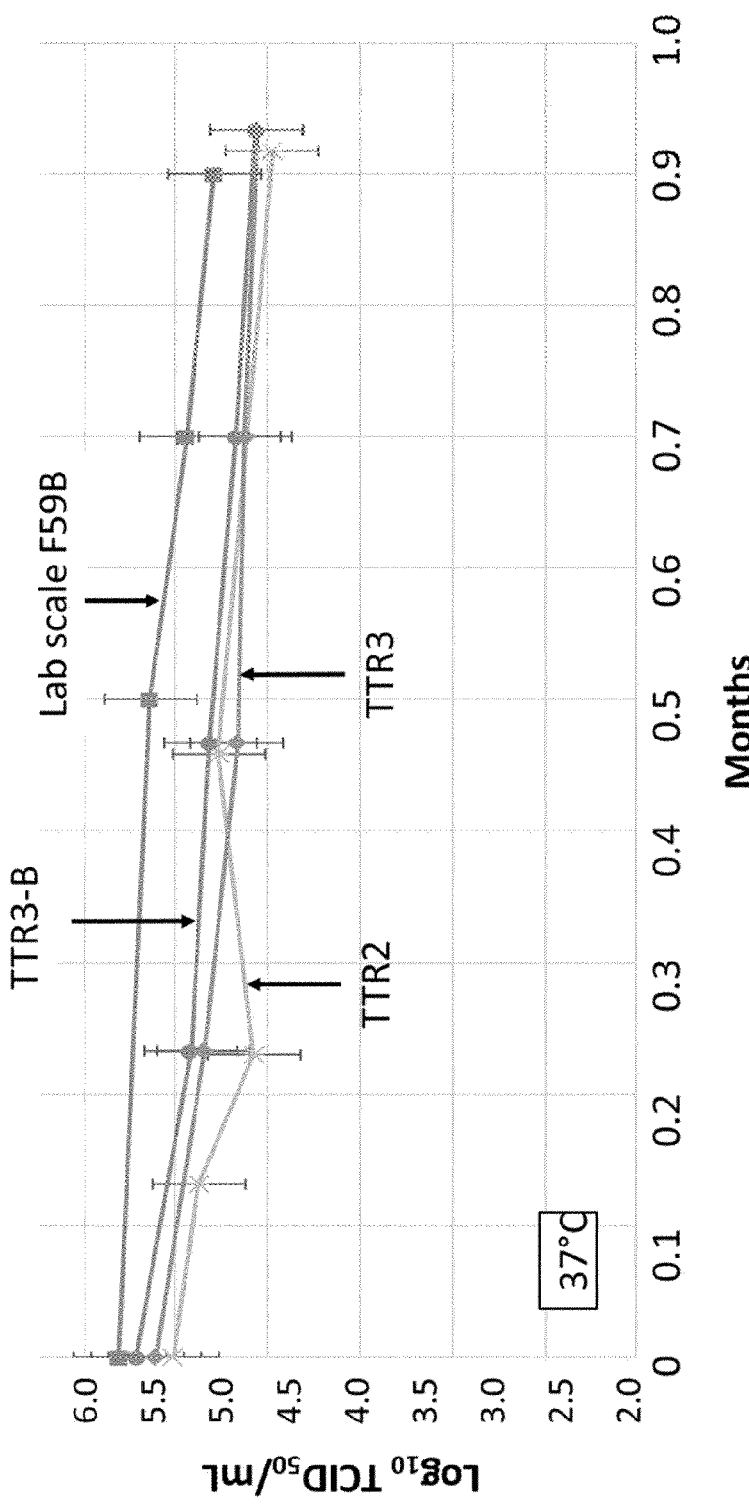
FIG. 9 Stability of CHIKV-Δ5nsP3-inv DP formulations (at lab and intermediate scale) at 37° C. $TCID_{50}$ assay (error bars of ±0.5 log).

Accelerated stability studies conducted by the incubation of samples at elevated temperatures provides information with respect to stability differences within a shorter time frame. FIG. 8 shows stability data of TTR2, TTR3 and F59B stored at room temperature. The stability of TTR3 was also assess in parallel by a different internal department as a further control (TTR3-B). FIG. 9 depicts the stability data of the same formulations at 37° C. All data represent $\log_{10}$ TCID$_{50}$/mL values as assessed directly after reconstitution.

Figure 25:
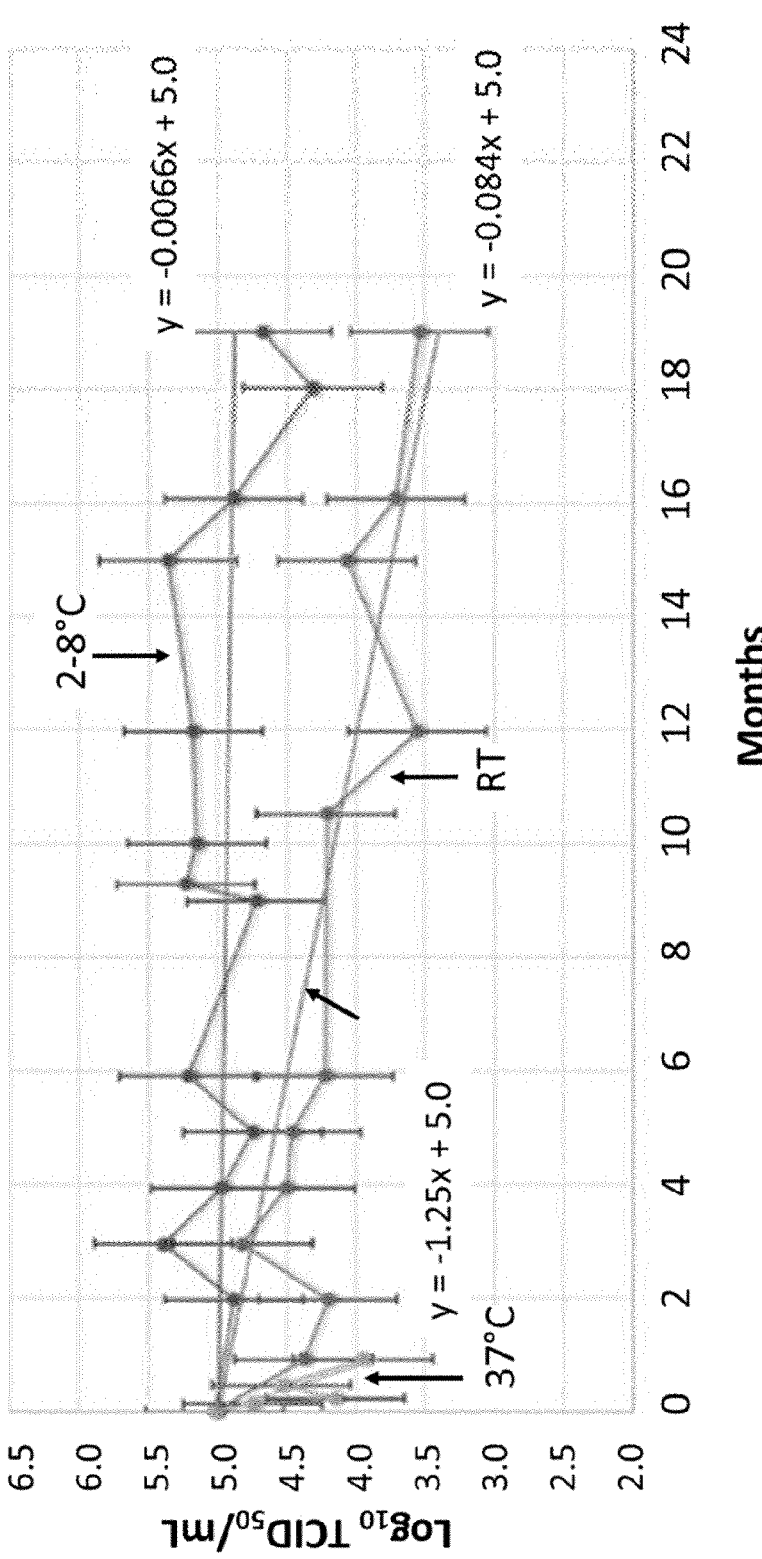
FIG. 25 Stability of lyophilized DP produced at intermediate scale (technical transfer; TTR2) at 2-8° C., room temperature (RT) and 37° C., as assessed by $TCID_{50}$ at each timepoint directly after reconstitution in WFI.

At both accelerated storage temperatures, no significant differences between lab and intermediate scale material were observed. At 37° C., the loss of infectivity was approximately 1 $\log_{10}$ per month and at room temperature approximately 1 $\log_{10}$ in 6 months. Results from a longer study with one of the intermediate scale samples (TTR2) comparing stability at all three temperatures indicated good stability at 2-8° C. up to 19 months (FIG. 25).

To illustrate the influence of TCID$_{50}$ assay variability on the predictability of long term stability at 2-8° C. a lab scale formulation is shown in Table 12.

TABLE 12

| Stability results (TCID$_{50}$) of lyophilized DP at 2-8° C., RT and 37° C. | | | | | | | | | | |
| --- | --- | --- | --- | --- | --- | --- | --- | --- | --- | --- |
| | $\log_{10}$ TCID$_{50}$/mL Days | | | | | | | | | |
| | 0 | 14 | 21 | 28 | 60 | 90 | 120 | 150 | 180 | 270 | 365 |
| 2-8° C. | 5.7 | n.a. | n.a. | 5.5 | 5.5 | 5.7 | 5.3 | n.a. | 5.5 | 5.7 | 5.3 |
| RT (22° C.) | | 5.9 | n.a. | 5.6 | 5.3 | 5.1 | 4.8 | n.a. | n.a. | n.a. | n.a. |
| 37° C. | | 5.0 | 5.0 | 4.7 | n.a. | n.a. | n.a. | n.a. | n.a. | n.a. | n.a. |

CHIKV-Δ5nsP3-inv showed excellent stability at 2-8° C. and room temperature based on the currently available data for lab and intermediate scales. An acceptable loss of infectivity of approximately 1 $\log_{10}$ TCID$_{50}$/mL was observed when stored for 28 days at 37° C. Studies are currently ongoing to confirm long-term storage stability of CHIKV-Δ5nsP3-inv at 2-8° C. with an anticipated stability profile of less than 1 $\log_{10}$ TCID$_{50}$/mL loss after two years storage.

It should also be noted that slight variations of lyophilization parameters (e.g., temperature and duration during primary and secondary drying) did not significantly alter the stability profile of CHIKV-Δ5nsP3-inv after lyophilization at various storage temperatures (data not shown).

Overall conclusion on stability of the CHIKV lyo formulation: Loss of infectivity over time when batches were stored at 2-8° C. was minimal considering a potential TCID$_{50}$ assay variability of 0.3 $\log_{10}$. In other words, significant differences at 2-8° C. may be better assessed after long term storage. Extrapolation of stability up to two years based on the existing data estimates a loss in infectivity of up to 1 $\log_{10}$ TCID$_{50}$/mL at 2-8° C.

Stability data generated at accelerated temperatures provides information on stability differences between batches in a shorter time frame. In this regard, no significant differences between lyophilized DP derived from lab and intermediate scale were observed from studies carried out at 25° C. and 37° C. Based on the data obtained, the loss of infectivity at 37° C. is approximately 1 $\log_{10}$ TCID$_{50}$/mL per month and at 25° C. approximately 1 $\log_{10}$ TCID$_{50}$/mL in 6 months.

Example 4. CHIKV Liquid Frozen Formulation Development

During the development of the Chikungunya vaccine candidate CHIKV-Δ5nsP3-inv, the generation of specific mutations in the virus genome could be observed in response to the adaption required for growing on Vero cells (see also WO2019057793, which is incorporated herein by reference in its entirety). One of these mutations is located in the structural E2 protein at position 168, changing a glutamic acid residue to lysine (E168K). This mutation is the dominant phenotype in later passages on vero cells (P6 and higher) and correlated with a loss of immunogenicity of the attenuated CHIKV in the mouse model. To reduce the risk of producing non-immunogenic batches, a virus master bank was generated as P1 and a working bank as P2, resulting in production passage P3. Interestingly, it was found that different virus passages need different buffer compositions with regard to stability and degradation effects, apparently due to different surface charges introduced by mutations.

Most of the initial formulation development work was done using Passage 8 material. The following formulation was developed:

The optimal pH range is 6.5 to 7.3 with higher stability at lower pH

Human Serum Albumin (rHSA) is required at concentrations of between 0.01-1%

Sucrose is needed to improve freeze/thaw stability (5% final concentration)

Histidine is best buffering compound (20 mM final concentration)

Composition of Initial Liquid Formulation Buffer:

20 mM Histidine pH 6.8, 5% sucrose, 0.1% rHSA

Additionally, during initial development, buffers were prepared with MilliQ water of high purity. However, when Passage 3 (P3) material was diluted using the same formulation buffer but prepared in water for injection (WFI), it was found that this virus passage was not compatible with the buffer any more. Upon dilution the virus size increased immediately (larger than 200 nm in diameter) most probably because of aggregation. This virus solution was therefore not sterile filterable (0.2 μm filter) which is a prerequisite for vaccine production. Phosphate-citrate buffering systems have been reported to be compatible with CHIKV VLPs (Richard Schwartz, Formulation and Stability of a Chikungunya Virus-Like Particle (ChikV VLP) Based Vaccine" in "Vaccine Technology IV", B. Buckland, University College London, UK; J. Aunins, Janis Biologics, LLC; P. Alves, ITQB/IBET; K. Jansen, Wyeth Vaccine Research Eds, ECI Symposium Series, (2013). http://dc.engconfintl.org/vaccine_iv/17).

Therefore, the following phosphate-citrate buffered formulation was developed, guided by extensive previous experience with the histidine-buffered CHIKV formulation, and evaluated for its suitability to formulate CHIKV and to ensure sterile filterability during DS and DP production:

10 mM potassium phosphate 25 mM sodium citrate

5% sucrose 0.01% rHSA pH 7.3

The useful concentration range of its components was investigated and is summarized in the following sections. As the final rHSA concentration was not fixed in most experiments 0.02% rHSA was chosen at the beginning to prevent unspecific adsorption at surfaces. Most analytical data were generated by DLS as this method provides a fast evaluation of the particle size, which is critical for filterability.

Influence of Phosphate Concentration

Figure 10:
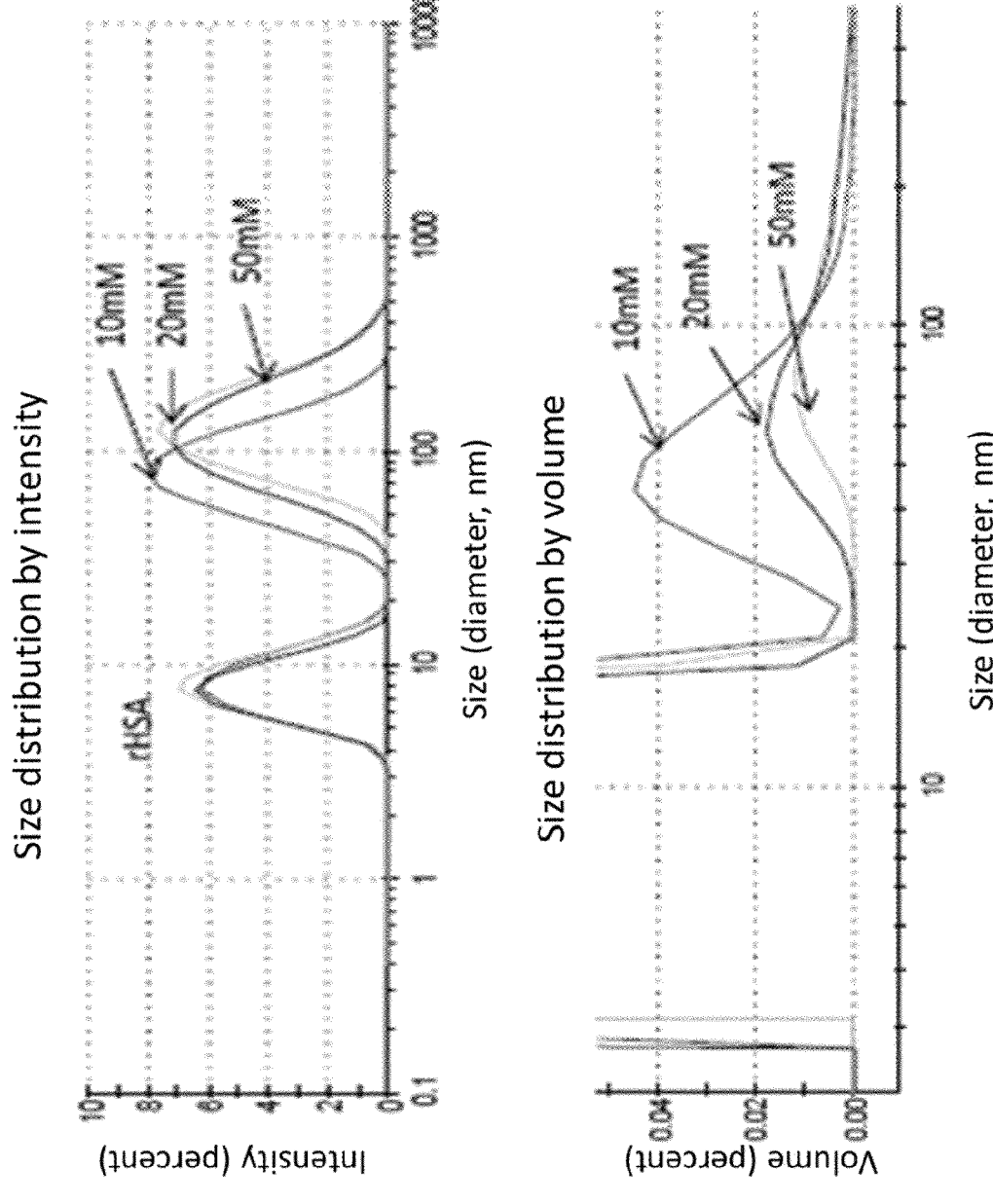
FIG. 10 Influence of increasing phosphate concentration on CHIKV-Δ5nsP3-inv size.

The buffering component—potassium phosphate—was tested in the range of 10 to 50 mM. As shown in FIG. 10, the DLS data generated indicated that higher phosphate concentrations led to an increase in particle size of CHIKV-Δ5nsP3-inv (~90 nm at 10 mM to ~140 nm at 50 mM phosphate). A concentration of 10 mM was chosed for phosphate.

Influence of NaCl Concentration in Phosphate Buffered Solution

Figure 11:
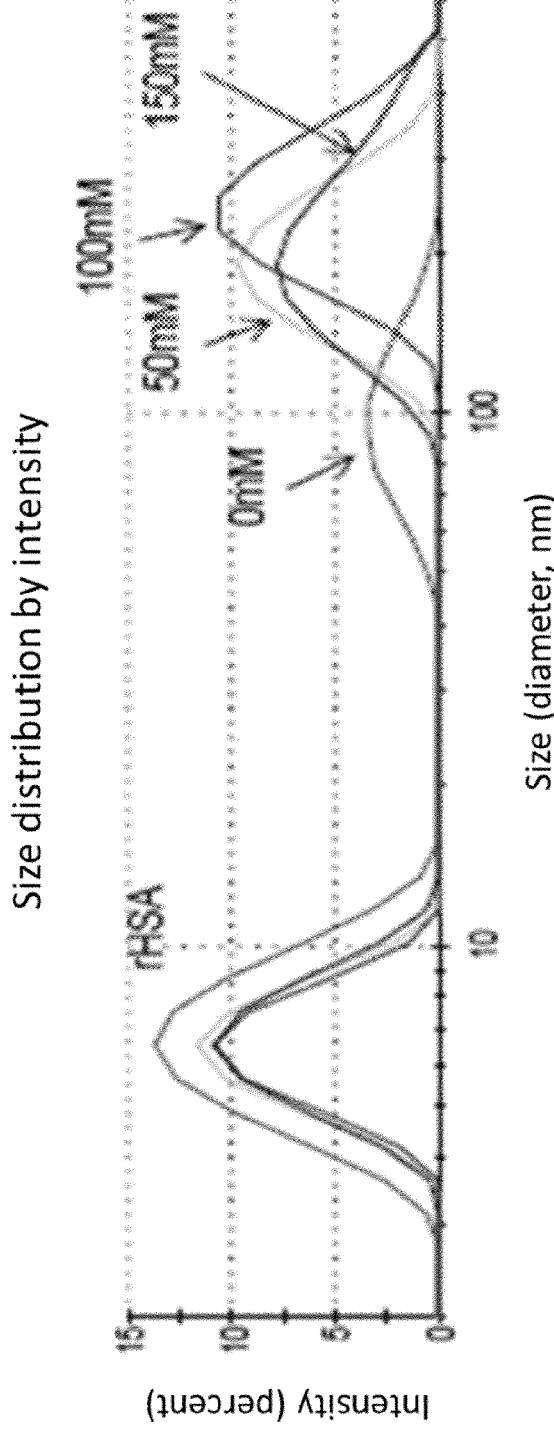
FIG. 11 Influence of increasing NaCl concentration on CHIKV-Δ5nsP3-inv size in phosphate buffer.

In order to evaluate if sodium chloride exhibits a similar effect as citrate with regard to virus size, it was investigate between 0 and 150 mM (no citrate present). All measurements were done within 15 minutes after addition of SGP to the buffer. FIG. 11 clearly shows that NaCl in phosphate buffered solution significantly increases the virus size from approximately 100 nm (no NaCl) to ~200 nm at 150 mM NaCl. Therefore, NaCl was not further investigated and was excluded as an additional excipient.

Influence of Citrate Concentration

Figure 12:
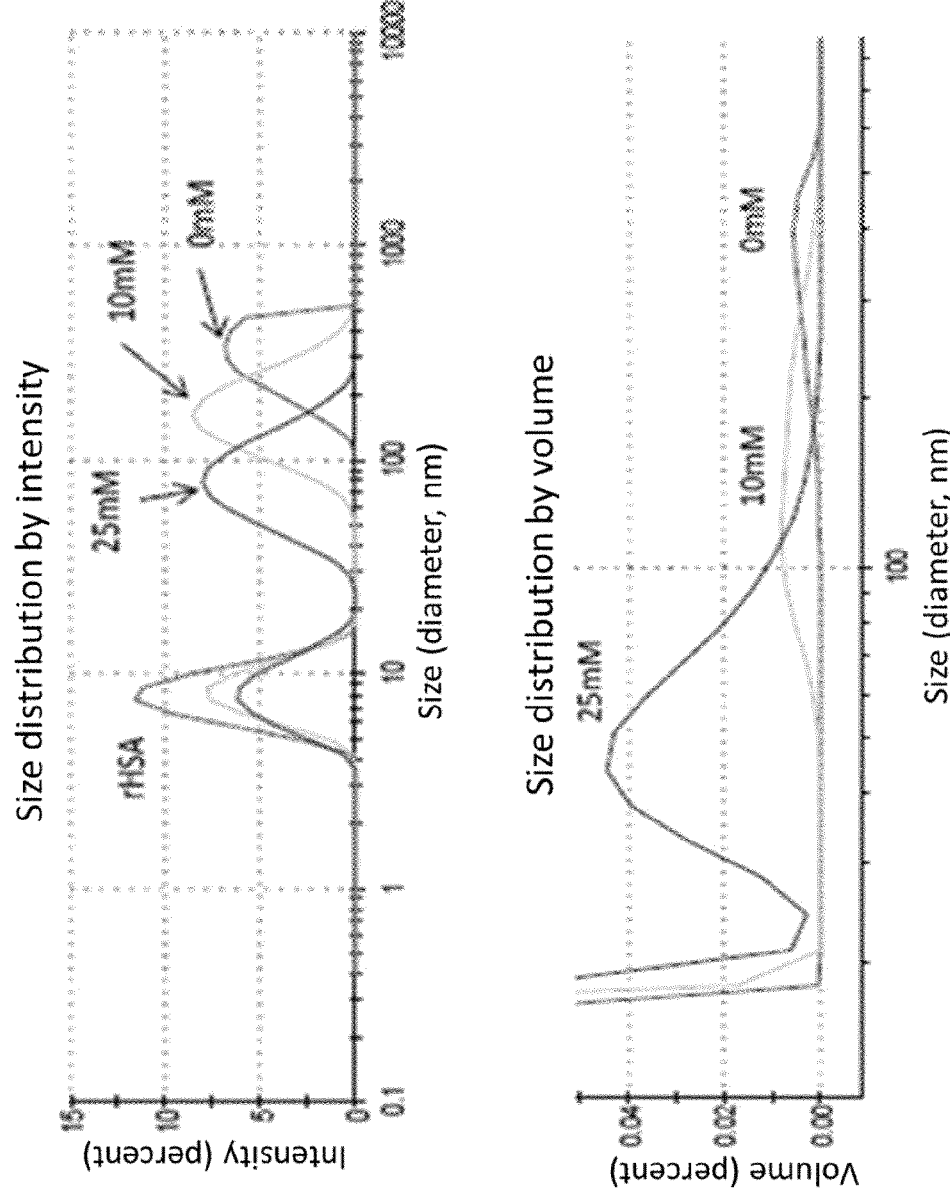
FIG. 12 Influence of increasing citrate concentration on CHIKV-Δ5nsP3-inv size.

Citrate has been reported to inhibit aggregation of CHIKV VLPs (Kramer R M, et al. Development of a Stable Virus-Like Particle Vaccine Formulation against Chikungunya Virus and Investigation of the Effects of Polyanions. 2013 J Pharm Sci. 102(12): 4305-4314. doi:10.1002/jps.23749). Reasoning that whole CHIK virus particles may behave similarly in solution to CHIKV VLPs, different concentrations of citrate were tested to evaluate its influence on virus size. Indeed, a significant and dose-dependent reduction in particle size was observed by addition of citrate (FIG. 12). Virus in phosphate formulation buffer without citrate showed a size of ~300 nm compared to ~90 nm with 25 mM citrate. Therefore, the citrate concentration was fixed at 25 mM in the formulation buffer to keep the virus size as small as possible to facilitate 0.2 m sterile filtration.

Influence of pH

Depending on the extent of mutations of viral proteins, the charges presented at the surface might change. With respect to this changed surface charge, also pH changes might significantly change the aggregation behavior of the virus. pH was investigated in the range of 7.0 to 7.6 (10 mM potassium phosphate, 25 mM sodium citrate, 5% sucrose, 0.02% rHSA). The influence of pH changes in this range seems not to be significant regarding the particle size with approximately 100 nm (data not shown).

Influence of Other Additives

Various additional buffer additives were investigated for potential stabilizing effects on CHIKV-Δ5nsP3-mv size:

10 mM $CaCl_2$ 10 mM $MgCl_2$ 5 mM EDTA 25 mM KCl 25 mM alanine 2.5% sorbitol

Components were added at the indicated concentrations to the formulation buffer (10 mM $PO_4$, 25 mM citrate, 5% sucrose, 0.02% rHSA, pH 7.3). DLS measurement was performed within 30 minutes after virus addition. No major influences on CHIKV diameter caused by the different buffer additives were observed compared to the original buffer (data not shown). As CHIKV diameter was already stable in the basic formulation buffer, no further advantages of the incorporation of these additional excipients could be determined. Apart from that, also no negative effect was determined. Therefore, the buffer additives tested represent an opportunity if further components are needed within the formulation buffer system for later CHIKV formulation optimization.

Influence of rHSA

In order to evaluate which effect rHSA exerts on CHIKV-Δ5nsP3-inv size, different amounts of rHSA (0-0.1%) were added to the formulation buffer (10 mM potassium phosphate, 25 mM sodium citrate, 5% sucrose, pH 7.3) and measured by DLS immediately after virus addition (SGP, 1:40 in respective buffer). Increasing rHSA concentrations caused CHIKV aggregation from 79 nm (without rHSA) to >250 nm in diameter (0.1% rHSA). The same result was observed when analyzing DLS data for size distribution by volume. Observed CHIKV diameters at the respective rHSA concentrations are listed in Table 13. The effect of rHSA on CHIKV diameters over time is shown in Table 14.

TABLE 13

Influence of rHSA on CHIKV-Δ5nsP3-inv diameter (size distribution by intensity).

| rHSA (%) | CHIKV Diameter (nm) |
|---|---|
| 0 | 79 |
| 0.01 | 141 |
| 0.02 | 203 |
| 0.05 | 188 |
| 0.1 | 266 |

Based on these data, it was concluded that an rHSA concentration up to 0.01% is still suitable for 0.2 μm filtration, whereas rHSA concentrations ≥0.02% would lead to significant losses of virus during sterile filtration.

The incorporation of a minimal amount of rHSA is desired to prevent unspecific adsorption to surfaces of containers. Therefore, 0.01% rHSA in the formulation buffer is desirable and may be present without significantly reducing recovery during 0.2 μm sterile filtration of DS or DP as virus diameter is still below 200 nm.

TABLE 14

| | CHIKV-Δ5nsP3-inv diameter at different rHSA concentrations over time. | | |
|---|---|---|---|
| | | CHIKV Diameter (nm) | |
| Time (h) | 0% rHSA | 0.01% rHSA | 0.1% rHSA |
| 0 | 79 | 141 | 266 |
| 2 | 87 | 149 | 434 |
| 3 | 99 | 153 | 499 |
| 22 | 94 | 175 | 459 |

Therefore, the rHSA concentration present in the formulation buffer was set to 0.01%, resulting in the following buffer composition for the liquid (frozen) formulation:

10 mM potassium phosphate
25 mM sodium citrate
5% sucrose
0.01% rHSA
pH 7.3

Stability Studies of DS and DP

Buffer: 10 mM potassium phosphate ($K_2HPO_4$ and $KH_2PO_4$), 25 mM sodium citrate ($Na_3CH_5O_7$), 5% sucrose, 0.01% rHSA, pH 7.3 (conductivity 6.0 mS/cm). Before usage, formulation buffer was 0.2 m sterile filtered. SGP-lot was diluted 1:40 in this buffer (195 mL buffer+5 mL SGP lot) stirred for 3 minutes and left at RT for 15 minutes (to simulate later manufacturing process in larger scale). Thereafter, virus solution was 0.2 μm filtered (PALL Mini Kleenpak, sterilized by gamma irradiation) into a 250 mL PETG bottle. DS after filtration was aliquoted in 60 mL PETG bottles (25 mL filling volume) when stored frozen at –80° C. (stability study ongoing) or in 1.5 mL Eppendorf tubes when stored in liquid form (2-8° C., RT, 37° C.).

Figure 13:
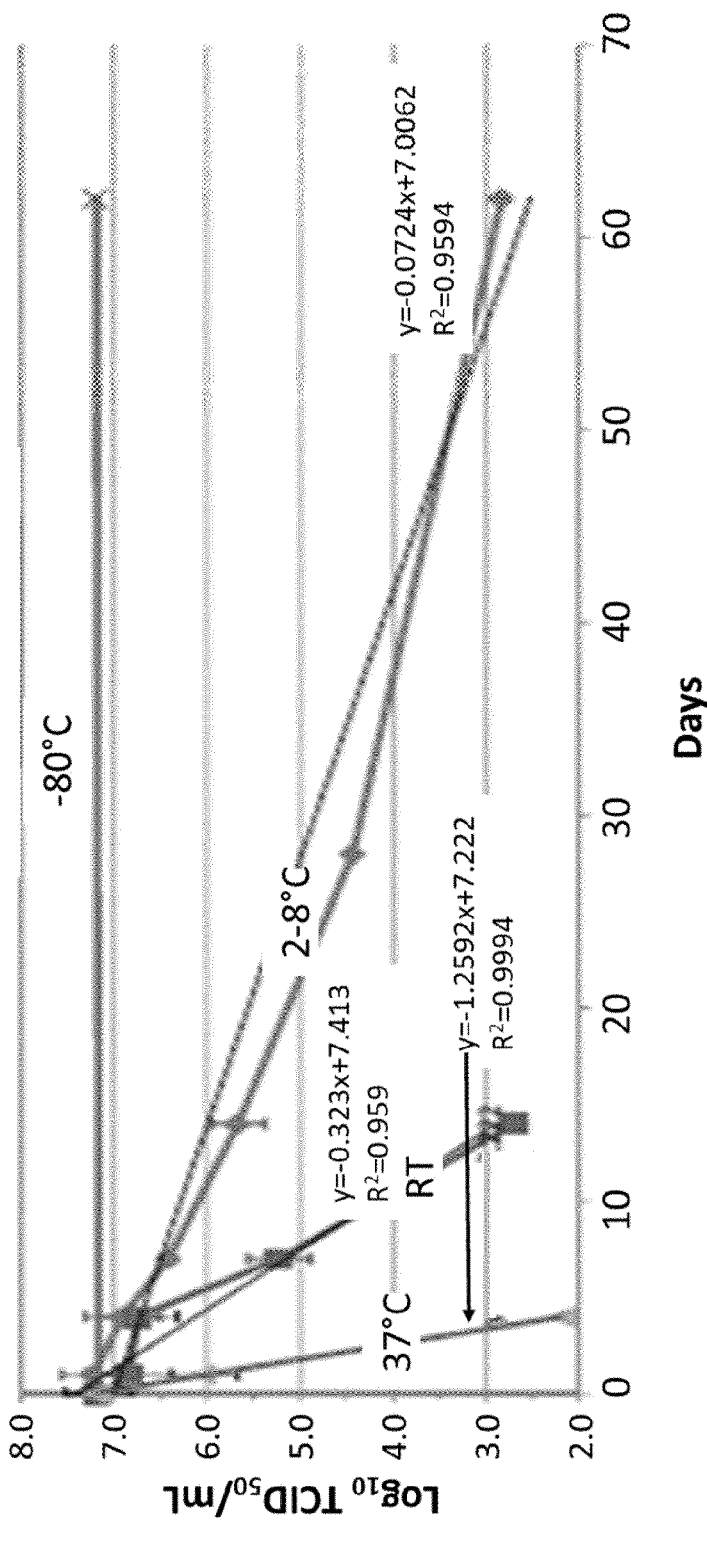
FIG. 13 Stability of CHIKV-Δ5nsP3-inv DS at various temperatures.
Figure 14:
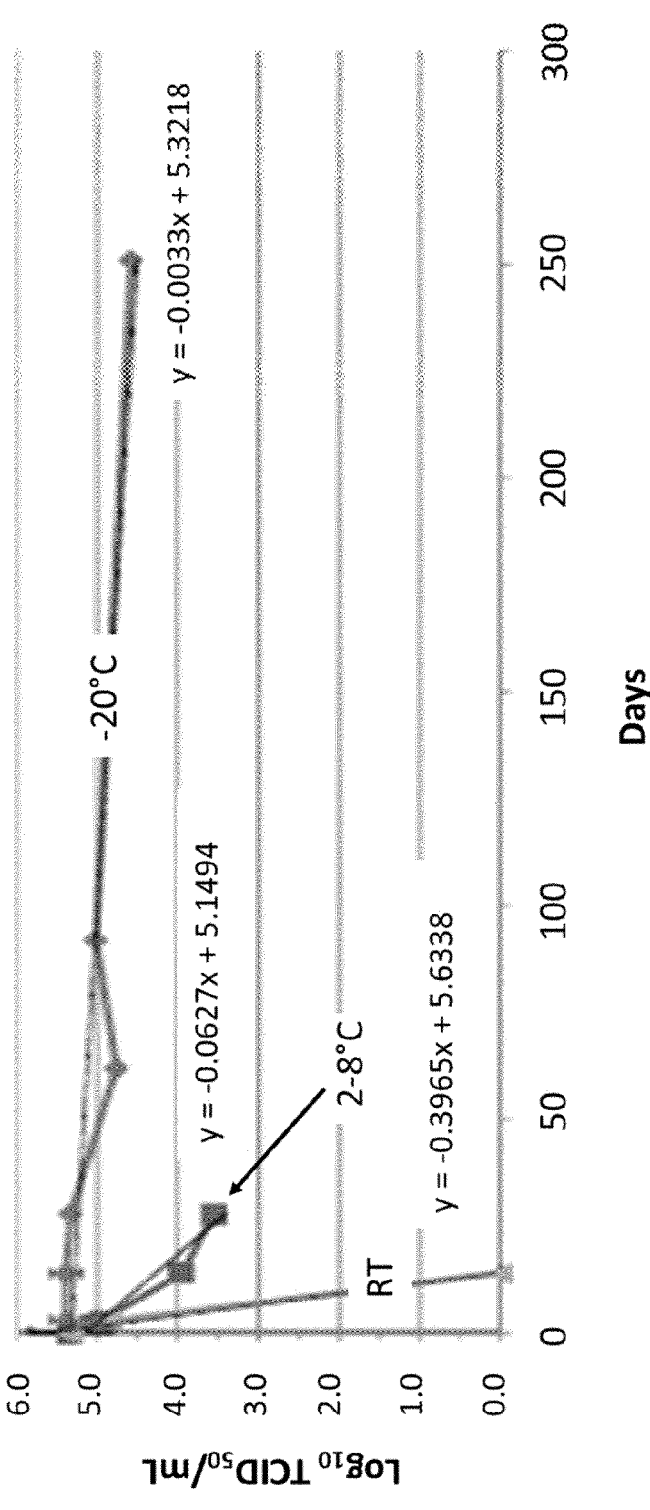
FIG. 14 Stability of CHIKV-Δ5nsP3-inv DP high dose at various temperatures. Material stored in glass vials.

As expected, DS in the liquid (frozen) formulation stored at –80° C. remained stable at the day 60 time point (FIG. 13). When stored at 2-8° C. a decline of infectivity of approximately 0.5 log $TCID_{50}$/mL per week was observed. A complete loss of infectivity within a short time frame was observed when the material was stored at room temperature (after approx. two weeks) and at 37° C. (less than one week).

This DS was further processed to DP by a 1:50 dilution (196 mL formulation buffer+4 mL CHIKV DS). After mixing for 3 minutes and incubation for 15 minutes at room temperature, DP was filtered into a PETG bottle (Mini Kleenpak EKV membrane) and filled into glass vials (1 mL filling volume) closed with Flurotec stoppers. Stability studies were undertaken on vials stored at –20° C. (normal storage temperature) and under accelerated conditions (2-8° C. and RT). The results after approx. 8 months storage are shown in the FIG. 14.

As Expected CHIKV-Δ5nsP3-Inv Presented in the Liquid (Frozen) Formulation was Unstable at 2-8° C. (~0.5 $log_{10}$ loss per week) and especially if stored at room temperature (complete loss of infectivity within two weeks).

Further preferred aspects of the invention:

1. A liquid frozen or lyophilized live chikungunya vaccine formulation comprising: a) an effective amount of at least one strain of live chikungunya virus; b) about 1 to 50% (w/v) sugar; c) about 1 mM to about 20 mM phosphate; d) about 1 mM to about 50 mM of at least one carboxylate; e) optionally about 1 mM to about 10 mM MgCl2; f) optionally about 0.1% to about 5% (w/v) D-sorbitol; g) optionally about 1 mM to 20 mM L-methionine; and h) optionally about 0.001% to about 1% (w/v) human serum albumin.

2. The formulation of aspect 1, wherein the human serum albumin is a recombinant human serum albumin.

3. The formulation according to any preceding aspect, wherein said at least one carboxylate is selected from the group consisting of succinate, citrate, fumarate, tartarate, maleate and lactate.

4. The formulation according to any preceding aspect, wherein said sugar is selected from the group consisting of sucrose, mannitol, lactose, sorbitol, dextrose, fucose and trehalose.

5. The formulation according to any preceding aspect, wherein the concentration of sugar is between about 1 to about 10%; the concentration of phosphate is between about 1 to about 10 mM; and said at least one carboxylic acid is citrate or succinate at a concentration between about 10 to about 30 mM.

6. The formulation according to any preceding aspect, further comprising: k) at least one diluent selected from the group consisting of tissue culture medium, saline and water to volume.

7. The formulation according to any preceding aspect, wherein the pH is between about pH 5.0 to about pH 8.0, preferably between pH 7.0 and pH 7.5, most preferred pH 7.3.

8. The formulation according to any preceding aspect, wherein said phosphate is selected from the group consisting of monophosphates, polyphosphates and phosphorylated compounds.

9. The formulation according to aspect 8, wherein said monophosphate is potassium phosphate.

10. The formulation according to any preceding aspect, wherein formulation comprises an effective amount of at least one strain of chikungunya virus; b) sucrose at a concentration of about 5% (w/v); c) potassium phosphate at a concentration of about 5 mM to about 10 mM; d) sodium citrate at a concentration of about 25 mM; e) MgCl2 at a concentration of about 10 mM; f) D-sorbitol at a concentration of about 0.5% (w/v), g) L-methionine at a concentration of about 10 mM; and h) recombinant human serum albumin at a concentration of about 0.01% (w/v).

11. The formulation according to any preceding aspect, wherein formulation comprises an effective amount of at least one strain of chikungunya virus; b) about 5% (w/v) sucrose; c) about 5 mM potassium phosphate; d) about 25 mM sodium citrate; e) about 10 mM $MgCl_2$; f) about 0.5% (w/v) D-sorbitol, g) about 10 mM L-methionine; and h) about 0.01% (w/v) recombinant human serum albumin.

12. The formulation according to any preceding aspect, wherein said chikungunya virus is selected from an attenuated chikungunya virus of SEQ ID NO: 1; variants with 99% sequence identity to SEQ ID NO: 1 of which all are lacking the 60 nt deletion; and/or combinations thereof.

13. The formulation according to any preceding aspect, wherein said chikungunya virus comprises essentially an attenuated chikungunya virus of SEQ ID NO: 1 and a variant with 99% sequence identity to SEQ ID NO: 1 and lacking the 60 nt deletion.

14. The formulation according to any preceding aspect, wherein said at least one strain of chikungunya virus is selected from an attenuated chikungunya virus population that comprises substantially 2 variants, said variants expressing the E1 wild type amino acid sequence as encoded in the relevant part of nucleic acid sequence SEQ ID NO: 1 and wherein one variant expressing the wild type E2 structural protein as defined in SEQ ID NO: 2 and wherein the other variant expressing the E168K mutation in the E2 structural protein as defined in SEQ ID NO: 3.

15. The lyophilized chikungunya vaccine formulation according to any preceding aspect, wherein said chikungunya virus is an attenuated chikungunya virus population that comprises substantially 2 variants, said variants expressing E2 structural proteins as defined by the amino acid sequences of SEQ ID NO: 2 and SED ID NO: 3 (with E168K) and wherein said 2 variants have a combined dose between about $10^3$ and $2 \times 10^4$ $TCID_{50}$/dose and a target potency of about $5 \times 10^3$ $TCID_{50}$/dose.

16. The lyophilized chikungunya vaccine formulation according to any preceding aspect, wherein said chikungunya virus is an attenuated chikungunya virus population that comprises one or more variants and wherein the variant has one or more mutations in E2 which mutations are shown in the group of variants encoding for an E2 amino acid sequence with E168K (SEQ ID NO: 3), G55R (SEQ ID NO: 4), E247K (SEQ ID NO: 5), G82R (SEQ ID NO: 6) and/or H232Y (SEQ ID NO: 7).

17. A method of preparing chikungunya virus vaccine formulations, comprising:
   (a) cultivating a chikungunya virus and mixing the chikungunya virus with a concentrated stabilizing solution to form a virus bulk; and, optionally,
   (b) dialyzing the virus bulk to form a chikungunya virus vaccine solution; wherein the vaccine solution comprises a) about 1 to 50% (w/v) sugar; b) about 1 mM to about 20 mM phosphate; c) about 1 mM to about 50 mM of at least one carboxylate; d) about 1 mM to about 10 mM MgCl2; e) about 0.1% to about 5% (w/v) D-sorbitol; g) about 1 mM to 20 mM L-methionine; and f) about 0.001% to about 1% (w/v) human serum albumin.

18. The method of aspect 17, wherein the stabilizing solution comprises a) about 5% (w/v) sugar; b) about 20 mM phosphate; c) about 25 mM citrate; d) about 10 mM MgCl2; e) about 0.5% (w/v) D-sorbitol; f) about 10 mM L-methionine; and g) about 0.01% (w/v) human serum albumin.

19. The method of aspect 17 or 18, wherein the dialyzing is done to form a formulation of any of aspects 1 to 16.

20. The method of any of aspects 17 to 19, further comprising the step of lyophilizing the vaccine solution.

---

SEQUENCES

---

SEQ ID NO: 1
Nucleotide sequence of CHIKV-Δ5nsP3
GATGGCTGCGTGAGACACACGTAGCCTACCAGTTTCTTACTGCTCTACTCTGCAAAGCAAGAGATTA
ATAACCCATCATGGATCCTGTGTACGTGGACATAGACGCTGACAGCGCCTTTTTGAAGGCCCTGCAA
CGTGCGTACCCCATGTTTGAGGTGGAACCAAGGCAGGTCACACCGAATGACCATGCTAATGCTAGA
GCGTTCTCGCATCTAGCTATAAAACTAATAGAGCAGGAAATTGACCCCGACTCAACCATCCTGGATAT
CGGCAGTGCGCCAGCAAGGAGGATGATGTCGGACAGGAAGTACCACTGCGTCTGCCCGATGCGCA
GTGCGGAAGATCCCGAGAGACTCGCCAATTATGCGAGAAAGCTAGCATCTGCCGCAGGAAAAGTCC
TGGACAGAAACATCTCTGGAAAGATCGGGGACTTACAAGCAGTAATGGCCGTGCCAGACACGGAGA
CGCCAACATTCTGCTTACACACAGACGTCTCATGTAGACAGAGAGCAGACGTCGCTATATACCAAGA
CGTCTATGCTGTACACGCACCCACGTCGCTATACCACCAGGCGATTAAAGGGGTCCGAGTGGCGTA
CTGGGTTGGGTTCGACACAACCCCGTTCATGTACAATGCCATGGCGGGTGCCTACCCCTCATACTC
GACAAACTGGGCAGATGAGCAGGTACTGAAGGCTAAGAACATAGGATTATGTTCAACAGACCTGACG
GAAGGTAGACGAGGCAAGTTGTCTATTATGAGAGGGAAAAAGCTAAAACCGTGCGACCGTGTGCTG
TTCTCAGTAGGGTCAACGCTCTACCCGGAAAGCCGCAAGCTACTTAAGAGCTGGCACCTGCCATCG
GTGTTCCATTTAAAGGGCAAACTCAGCTTCACATGCCGCTGTGATACAGTGGTTTCGTGTGAGGGCT
ACGTCGTTAAGAGAATAACGATGAGCCCAGGCCTTTATGGAAAAACCACAGGGTATGCGGTAACCCA
CCACGCAGACGGATTCCTGATGTGCAAGACTACCGACACGGTTGACGGCGAAAGAATGTCATTCTC
GGTGTGCACATACGTGCCGGCGACCATTTGTGATCAAATGACCGGCATCCTTGCTACAGAAGTCAC
GCCGGAGGATGCACAGAAGCTGTTGGTGGGGCTGAACCAGAGAATAGTGGTTAACGGCAGAACGC
AACGGAATACGAACACCATGAAAAATTATCTGCTTCCCGTGGTCGCCCAAGCCTTCAGTAAGTGGGC
AAAGGAGTGCCGGAAAGACATGGAAGATGAAAAACTCCTGGGGGTCAGAGAAAGAACACTGACCTG
CTGCTGTCTATGGGCATTCAAGAAGCAGAAAACACACACGGTCTACAAGAGGCCTGATACCCAGTCA
ATTCAGAAGGTTCAGGCCGAGTTTGACAGCTTTGTGGTACCGAGTCTGTGGTCGTCCGGGTTGTCAA
TCCCTTTGAGGACTAGAATCAAATGGTTGTTAAGCAAGGTGCCAAAAACCGACCTGATCCCATACAG
CGGAGACGCCCGAGAAGCCCGGGACGCAGAAAAAGAAGCAGAGGAAGAACGAGAAGCAGAACTGA
CTCGCGAAGCCCTACCACCTCTACAGGCAGCACAGGAAGATGTTCAGGTCGAAATCGACGTGGAAC
AGCTTGAGGACAGAGCGGGCGCAGGAATAATAGAGACTCCGAGAGGAGCTATCAAAGTTACTGCCC
AACCAACAGACCACGTCGTGGGAGAGTACCTGGTACTCTCCCCGCAGACCGTACTACGTAGCCAGA
AGCTCAGTCTGATTCACGCTTTGGCGGAGCAAGTGAAGACGTGCACGCACAACGGACGAGCAGGGA
GGTATGCGGTCGAAGCGTACGACGGCCGAGTCCTAGTGCCCTCAGGCTATGCAATCTCGCCTGAAG
ACTTCCAGAGTCTAAGCGAAAGCGCAACGATGGTGTATAACGAAAGAGAGTTCGTAAACAGAAAGCT
ACACCATATTGCGATGCACGGACCAGCCCTGAACACCGACGAAGAGTCGTATGAGCTGGTGAGGGC
AGAGAGGACAGAACACGAGTACGTCTACGACGTGGATCAGAGAAGATGCTGTAAGAAGGAAGAAGC
CGCAGGACTGGTACTGGTGGGCGACTTGACTAATCCGCCCTACCACGAATTCGCATATGAAGGGCT
AAAAATCCGCCCTGCCTGCCCATACAAAATTGCAGTCATAGGAGTCTTCGGAGTACCGGGATCTGGC
AAGTCAGCTATTATCAAGAACCTAGTTACCAGGCAGGACCTGGTGACTAGCGGAAAGAAAGAAAACT
GCCAAGAAATCACCACCGACGTGATGAGACAGAGAGGTCTAGAGATATCTGCACGTACGGTTGACT
CGCTGCTCTTGAATGGATGCAACAGACCAGTCGACGTGTTGTACGTAGACGAGGCGTTTGCGTGCC
ACTCTGGAACGCTACTTGCTTTGATCGCCTTGGTGAGACCAAGGCAGAAAGTTGTACTTTGTGGTGA
CCCGAAGCAGTGCGGCTTCTTCAATATGATGCAGATGAAAGTCAACTATAATCACAACATCTGCACC

| SEQUENCES |
| --- |

```
CAAGTGTACCACAAAAGTATCTCCAGGCGGTGTACACTGCCTGTGACCGCCATTGTGTCATCGTTGC
ATTACGAAGGCAAAATGCGCACTACGAATGAGTACAACAAGCCGATTGTAGTGGACACTACAGGCTC
AACAAAACCTGACCCTGGAGACCTCGTGTTAACGTGCTTCAGAGGGTGGGTTAAACAACTGCAAATT
GACTATCGTGGATACGAGGTCATGACAGCAGCCGCATCCCAAGGGTTAACCAGAAAAGGAGTTTAC
GCAGTTAGACAAAAGTTAATGAAAACCCGCTCTATGCATCAACGTCAGAGCACGTCAACGTACTCC
TAACGCGTACGGAAGGTAAACTGGTATGGAAGACACTTTCCGGCGACCCGTGGATAAAGACGCTGC
AGAACCCACCGAAAGGAAACTTCAAAGCAACTATTAAGGAGTGGGAGGTGGAGCATGCATCAATAAT
GGCGGGCATCTGCAGTCACCAAATGACCTTCGATACATTCCAAATAAAGCCAACGTTTGTTGGGCT
AAGAGCTTGGTCCCTATCCTCGAAACAGCGGGGATAAAACTAAATGATAGGCAGTGGTCTCAGATAA
TTCAAGCCTTCAAAGAAGACAAAGCATACTCACCTGAAGTAGCCCTGAATGAAATATGTACGCGCAT
GTATGGGGTGGATCTAGACAGCGGGCTATTTTCTAAACCGTTGGTGTCTGTGTATTACGCGGATAAC
CACTGGGATAATAGGCCTGGAGGGAAAATGTTCGGATTTAACCCCGAGGCAGCATCCATTCTAGAAA
GAAAGTATCCATTCACAAAAGGGAAGTGGAACATCAACAAGCAGATCTGCGTGACTACCAGGAGGAT
AGAAGACTTTAACCCTACCACCAACATCATACCGGCCAACAGGAGACTACCACACTCATTAGTGGCC
GAACACCGCCCAGTAAAAGGGGAAAGAATGGAATGGCTGGTTAACAAGATAAACGGCCACCACGTG
CTCCTGGTCAGTGGCTATAACCTTGCACTGCCTACTAAGAGAGTCACTTGGGTAGCGCCGTTAGGTG
TCCGCGGAGCGGACTACACATACAACCTAGAGTTGGGTCTGCCAGCAACGCTTGGTAGGTATGACC
TAGTGGTCATAAACATCCACACACCTTTTCGCATACACCATTACCAACAGTGCGTCGACCACGCAAT
GAAACTGCAAATGCTCGGGGGTGACTCATTGAGACTGCTCAAACCGGGCGGCTCTCTATTGATCAG
AGCATATGGTTACGCAGATAGAACCAGTGAACGAGTCATCTGCGTATTGGGACGCAAGTTTAGATCG
TCTAGAGCGTTGAAACCACCATGTGTCACCAGCAACACTGAGATGTTTTTCCTATTCAGCAACTTTGA
CAATGGCAGAAGGAATTTCACAACTCATGTCATGAACAATCAACTGAATGCAGCCTTCGTAGGACAG
GTCACCCGAGCAGGATGTGCACCGTCGTACCGGGTAAAACGCATGGACATCGCGAAGAACGATGAA
GAGTGCGTAGTCAACGCCGCTAACCCTCGCGGGTTACCGGGTGGCGGTGTTTGCAAGGCAGTATAC
AAAAAATGGCCGGAGTCCTTTAAGAACAGTGCAACACCAGTGGGAACCGCAAAAACAGTTATGTGCG
GTACGTATCCAGTAATCCACGCTGTTGGACCAAACTTCTCTAATTATTCGGAGTCTGAAGGGGACCG
GGAATTGGCAGCTGCCTATCGAGAAGTCGCAAAGGAAGTAACTAGGCTGGGAGTAAATAGTGTAGC
TATACCTCTCCTCTCCACAGGTGTATACTCAGGAGGGAAAGACAGGCTGACCCAGTCACTGAACCAC
CTCTTTACAGCCATGGACTCGACGGATGCAGACGTGGTCATCTACTGCCGCGACAAAGAATGGGAG
AAGAAAATATCTGAGGCCATACAGATGCGGACCCAAGTAGAGCTGCTGGATGAGCACATCTCCATAG
ACTGCGATATTGTTCGCGTGCACCCTGACAGCAGCTTGGCAGGCAGAAAAGGATACAGCACCACGG
AAGGCGCACTGTACTCATATCTAGAAGGGACCCGTTTTCATCAGACGGCTGTGGATATGGCGGAGAT
ACATACTATGTGGCCAAAGCAAACAGAGGCCAATGAGCAAGTCTGCCTATATGCCCTGGGGGAAAG
TATTGAATCGATCAGGCAGAAATGCCCGGTGGATGATGCAGACGCATCATCTCCCCCCAAAACTGTC
CCGTGCCTTTGCCGTTACGCTATGACTCCAGAACGCGTCACCCGGCTTCGCATGAACCACGTCACA
AGCATAATTGTGTGTTCTTCGTTTCCCCTCCCAAAGTACAAAATAGAAGGAGTGCAAAAAGTCAAATG
CTCTAAGGTAATGCTATTTGACCACAACGTGCCATCGCGCGTAAGTCCAAGGGCTTATAGAGGTGCC
GCTGCCGGTAACCTTGCGGCCGTGTCTGATTGGGTAATGAGCACCGTACCTGTCGCGCCGCCCAGA
AGAAGGCGAGGGAGAAACCTGACTGTGACATGTGACGAGAGAGAAGGGAATATAACACCCATGGCT
AGCGTCCGATTCTTTAGGGCAGAGCTGTGTCCGGTCGTACAGAAACAGCGGAGACGCGTGACACA
GCAATGTCTCTTCAGGCACCACCGAGTACCGCCACGGAACCGAATCATCCGCCGATCTCCTTCGGA
GCATCAAGCGAGACGTTCCCCATTACATTTGGGGACTTCAACGAAGGAGAAATCGAAAGCTTGTCTT
CTGAGCTACTAACTTTCGGAGACTTCTTACCAGGAGAAGTGGATGACTTGACAGACAGCGACTGGTC
CACGTGCTCAGACACGGACGACGAGTTAAGACTAGACAGGGCAGGTGGGTATATATTCTCGTCGGA
CACCGGTCCAGGTCATTTACAACAGAAGTCAGTACGCCAGTCAGTGCTGCCGGTGAACACCCTGGA
GGAAGTCCACGAGGAGAAGTGTTACCCACCTAAGCTGGATGAAGCAAAGGAGCAACTATTACTTAAG
AAACTCCAGGAGAGTGCATCCATGGCCAACAGAAGCAGGTATCAGTCGCGCAAAGTAGAAAACATG
AAAGCAGCAATCATCCAGAGACTAAAGAGAGGCTGTAGACTATACTTAATGTCAGAGACCCCAAAAG
TCCCTACTTACCGGACTACATATCCGGCGCCTGTGTACTCGGCTCCGATCAACGTCCGATTGTCCAA
TCCCGAGTCCGCAGTGGCAGCATGCAATGAGTTCTTAGCTAGAAACTATCCAACTGTCTCATCTACAC
CAAATTACCGACGAGTATGATGCATATCTAGACATGGTGGACGGGTCGGAGAGTTGCCTGGACCGA
GCGACATTCAATCCGTCAAAACTCAGGAGCTACCCGAAACAGCACGCTTACCACGCGCCCTCCATCA
GAAGCGCTGTACCGTCCCCATTCCAGAACACACTACAGAATGTACTGGCAGCAGCCACGAAAAGAA
ACTGCAACGTCACACAGATGAGGGAATTACCCACTTTGGACTCAGCAGTATTCAACGTGGAGTGTTT
CAAAAAAATTCGCATGCAACCAAGAATACTGGGAAGAATTTGCTGCCAGCCCTATTAGGATAACAACT
GAGAATTTAGCAACCTATGTTACTAAACTAAAAGGGCCAAAAGCAGCAGCGCTATTCGCAAAAACCC
ATAATCTACTGCCACTACAGGAAGTACCAATGGATAGGTTCACAGTAGATATGAAAAAGGGACGTAAA
GGTGACTCCTGGTACAAAGCATACAGAGGAAAGACCTAAGGTGCAGGTTATACAGGCGGCTGAACC
CTTGGCGACAGCATACCTATGTGGGATTCACAGAGAGCTGGTTAGGAGGCTGAACGCCGTCCTCCT
ACCCAATGTACATACACTATTTGACATGTCTGCCGAGGATTTCGATGCCATCATAGCCGCACACTTTA
AGCCAGGAGACACTGTTTTGGAAACGGACATAGCCTCCTTTGATAAGAGGCCAAGATGATTCACTTGC
GCTTACTGCTTTGATGCTGTTAGAGGATTTAGGGGTGGATCACTCCCTGCTGGACTTGATAGAGGCT
GCTTTCGGAGAGATTTCCAGCTGTCACCTACCGACAGGTACGCGCTTCAAGTTCGGCGCCATGATG
AAATCAGGTATGTTCCTAACTCTGTTCGTCAACACATTGTTAAACATCACCATCGCCAGCCGAGTGCT
GGAAGATCGTCTGACAAAATCCGCGTGCGCGGCCTTCATCGGCGACGACAACATAATACATGGAGT
CGTCTCCGATGAATTGATGGCAGCCAGATGTGCCACTTGGATGAAGATGGAAGTGAAGATCATAGAT
GCAGTTGTATCCTTGAAAGCCCCCTTACTTTTGTGGAGGGTTTATACTGCACGATACTGTGACAGGAA
CAGCTTGCAGAGTGGCAGACCCGCTAAAAAAGGCTTTTTAAACTGGGCAAACCGCTAGCGGCAGGTG
ACGAACAAGATGAAGATAGAAGACGAGCGCTGGCTGACGAAGTGATCAGATGGCAACGAACAGGGC
TAATTGATGAGCTGGAGAAAGCGGTATACTCTAGGTACGAAGTGCAGGGTATATCAGTTGTGGTAAT
GTCCATGGCCACCTTTGCAAGCTCCAGATCCAACTTCGAGAAGCTCAGAGGACCCGTCATAACTTTG
TACGGCGGTCCTAAATAGGTACGCACTACAGCTACCTATTTTGCAGAAGCCGACAGCAAGTATCTAA
ACACTAATCAGCTACAATGGAGTTCATCCCAACCCAAACTTTTTACAATAGGAGGTACCAGCCTCGAC
CCTGGACTCCGCGCCCTACTATCCAAGTCATCAGGCCCAGACCGCGCCCTCAGAGGCAAGCTGGG
CAACTTGCCCAGCTGATCTCAGCAGTTAATAAACTGACAATGCGCGCGGTACCACAACAGAAGCCAC
GCAGGAATCGGAAGAATAAGAAGCAAAAGCAAAAACAACAGGCGCCACAAAACAACACAAATCAAAA
GAAGCAGCCACCTAAAAAGAAACCGGCTCAAAAGAAAAAGAAGCCGGGCCGCAGAGAGAGGATGTG
```

SEQUENCES

```
CATGAAAATCGAAAATGATTGTATTTTCGAAGTCAAGCACGAAGGTAAGGTAACAGGTTACGCGTGC
CTGGTGGGGGACAAAGTAATGAAACCAGCACACGTAAAGGGGACCATCGATAACGCGGACCTGGCC
AAACTGGCCTTTAAGCGGTCATCTAAGTATGACCTTGAATGCGCGCAGATACCCGTGCACATGAAGT
CCGACGCTTCGAAGTTCACCCATGAGAAACCGGAGGGGTACTACAACTGGCACCACGGAGCAGTAC
AGTACTCAGGAGGCCGGTTCACCATCCCTACAGGTGCTGGCAAACCAGGGGACAGCGGCAGACCG
ATCTTCGACAACAAGGGACGCGTGGTGGCCATAGTCTTAGGAGGAGCTAATGAAGGAGCCCGTACA
GCCCTCTCGGTGGTGACCTGGAATAAAGACATTGTCACTAAAATCACCCCCGAGGGGGCCGAAGAG
TGGAGTCTTGCCATCCCAGTTATGTGCCTGTTGGCAAACACCACGTTCCCCTGCTCCCAGCCCCTT
GCACGCCCTGCTGCTACGAAAAGGAACCGGAGGAAACCCTACGCATGCTTGAGGACAACGTCATGA
GACCTGGGTACTATCAGCTGCTACAAGCATCCTTAACATGTTCTCCCCACCGCCAGCGACGCAGCAC
CAAGGACAACTTCAATGTCTATAAAGCCACAAGACCATACTTAGCTCACTGTCCCGACTGTGGAGAA
GGGCACTCGTGCCATAGTCCCGTAGCACTAGAACGCATCAGAAATGAAGCGACAGACGGGACGCTG
AAAATCCAGGTCTCCTTGCAAATCGGAATAAAGACGGATGACAGCCACGATTGGACCAAGCTGCGTT
ATATGGACAACCACATGCCAGCAGACGCAGAGAGGGCGGGGCTATTTGTAAGAACATCAGCACCGT
GTACGATTACTGGAACAATGGGACACTTCATCCTGGCCCGATGTCCAAAAGGGGAAACTCTGACGGT
GGGATTCACTGACAGTAGGAAGATTAGTCACTCATGTACGCACCCATTTCACCACGACCCTCCTGTG
ATAGGTCGGGAAAAATTCCATTCCCGACCGCAGCACGGTAAAGAGCTACCTTGCAGCACGTACGTG
CAGAGCACCGCCGCAACTACCGAGGAGATAGAGGTACACATGCCCCCAGACACCCCTGATCGCACA
TTAATGTCACAACAGTCCGGCAACGTAAAGATCACAGTCAATGGCCAGACGGTGCGGTACAAGTGTA
ATTGCGGTGGCTCAAATGAAGGACTAACAACTACAGACAAAGTGATTAATAACTGCAAGGTTGATCAA
TGTCATGCCGCGGTCACCAATCACAAAAAGTGGCAGTATAACTCCCCTCTGGTCCCGCGTAATGCTG
AACTTGGGGACCGAAAAGGAAAAATTCACATCCCGTTTCCGCTGGCAAATGTAACATGCAGGGTGCC
TAAAGCAAGGAACCCCACCGTGACGTACGGGAAAAACCAAGTCATCATGCTACTGTATCCTGACCAC
CCAACACTCCTGTCCTACCGGAATATGGGAGAAGAACCAAACTATCAAGAAGAGTGGGTGATGCATA
AGAAGGAAGTCGTGCTAACCGTGCCGACTGAAGGGCTCGAGGTCACGTGGGGCAACAACGAGCCG
TATAAGTATTGGCCGCAGTTATCTACAAACGGTACAGCCCATGGCCACCCGCATGAGATAATTCTGT
ATTATTATGAGCTGTACCCCACTATGACTGTAGTAGTTGTGTCAGTGGCCACGTTCATACTCCTGTCG
ATGGTGGGTATGGCAGCGGGGATGTGCATGTGTGCACGAACGCATCACACCGTATGAACTG
ACACCAGGAGCTACCGTCCCTTTCCTGCTTAGCCTAATATGCTGCATCAGAACAGCTAAAGCGGCCA
CATACCAAGAGGCTGCGATATACCTGTGGAACGAGCAGCAACCTTTGTTTTGGCTACAAGCCCTTAT
TCCGCTGGCAGCCCTGATTGTTCTATGCAACTGTCTGAGACTCTTACCATGCTGCTGTAAAACGTTG
GCTTTTTTAGCCGTAATGAGCGTCGGTGCCCACACTGTGAGCGCGTACGAACACGTAACAGTGATCC
CGAACACGGTGGGAGTACCGTATAAGACTCTAGTCAATAGACCTGGCTACAGCCCCATGGTATTGGA
GATGGAACTACTGTCAGTCACTTTGGAGCCAACACTATCGCTTGATTACATCACGTGCGAGTACAAA
ACCGTCATCCCGTCTCCGTACGTGAAGTGCTGCGGTACAGCAGAGTGCAAGGACAAAAACCTACCT
GACTACAGCTGTAAGGTCTTCACCGGCGTCTACCCATTTATGTGGGGCGGCGCTACTGCTTCTGC
GACGCTGAAAACACGCAGTTGAGCGAAGCACACGTGGAGAAGTCCGAATCATGCAAAACAGAATTT
GCATCAGCATACAGGGCTCATACCGCATCTGCATCAGCTAAGCTCCGCGTCCTTTACCAAGGAAATA
ACATCACTGTAACTGCCTATGCAAACGGCGACCATGCCGTCACAGTTAAGGACGCCAAATTCATTGT
GGGGGCCAATGTCTTCAGCCTGGACACCTTTCGACAACAAAATTGTGGTGTACAAAGGTGACGTCTAT
AACATGGACTACCCGCCCTTTGGCGCAGGAAGACCAGGACAATTGGCGATATCCAAAGTCGCACA
CCTGAGAGTAAAGACGTCTATGCTAATACACAACTGGTACTGCAGAGACCGGCTGTGGGTACGGTA
CACGTGCCATACTCTCAGGCACCATCTGGCTTTAAGTATTGGCTAAAAGAACGCGGGGCGTCGCTG
CAGCACACAGCACCATTTGGCTGCCAAATAGCAACAAACCCGGTAAGAGCGGTGAACTGCGCCGTA
GGGAACATGCCCATCTCCATCGACATACCGGAAGCGGCCTTCACTAGGGTCGTCGACGCCCTCT
TTAACGGACATGTCGTGCGAGGTACCAGCCTGCACCCATTCCTCAGACTTTGGGGGCGTCGCCATT
ATTAAATATGCAGCCAGCAAGAAAGGCAAGTGTGCGGTGCATTCGATGACTAACGCCGTCACTATTC
GGGAAGCTGAGATAGAAGTTGAAGGGAATTCTCAGCTGCAAATCTCTTTCTCGACGGCCTTAGCCAG
CGCCGAATTCCGCGTACAAGTCTGTTCTACACAAGTACACTGTGCAGCCGAGTGCCACCCCCCGAA
GGACCACATAGTCAACTACCCGGCGTCACATACCACCCTCGGGGTCCAGGACATCTCCGCTACGGC
GATGTCATGGGTGCAGAAGATCACGGGAGGTGTGGGACTGGTTGTTGCTGTTGCCGCACTGATTCT
AATCGTGGTGCTATGCGTGTCGTTCAGCAGGCACTAACTTGACAATTAAGTATGAAGGTATATGTGTC
CCCTAAGAGACACACTGTACATAGCCAAATAATCTATAGATCAAAGGGCTACGCAACCCCTGAATAGTA
ACAAAATACAAAATCACTAAAAATTATAAAAACAGAAAAATACATAAATAGGTATACGTGTCCCCTAAG
AGACACATTGTATGTAGGTGATAAGTATAGATCAAAGGGCCGAATAACCCCTGAATAGTAACAAAATA
TGAAAATCAATAAAAATCATAAAATAGAAAAACCATAAACAGAAGTAGTTCAAAGGGCTATAAAACCC
CTGAATAGTAACAAAACATAAAATTAATAAAAATCAAATGAATACCATAATTGGCAAACGGAAGAGATG
TAGGTACTTAAGCTTCCTAAAAGCAGCCGAACTCACTTTGAAGAGTAGGCATAGCATACCGAACTCTT
CCACGATTCTCCGAACCCACAGGGACGTAGGAGATGTTATTTTGTTTTTAATATTTCAAAAAAAAAAA
AAAAAAAAAAA
```

SEQ ID NO: 2
Amino acid sequence of E2 protein from LR2006_OPY1 Chikungunya virus strain-
amino acids 339-742 from structural polyprotein; GenBank Accession: ABD95938.1
(1-1248 aa)
STKIDNFNVYKATRPYLAHCPDCGEGHSCHSPVALERIRNEATDGTLKIQVSLQIGIKTDDSHDWTKLRYM
DNHMPADAERAGLFVRTSAPCTITGTMGHFILARCPKGETLTVGFTDSRKISHSCTHPFHHDPPVIGREKF
HSRPQHGKELPCSTYVQSTAATTEEIEVHMPPDTPDHTLMSQQSGNVKITVNGQTVRYKCNCGGSNEG
LTTTDKVINNCKVDQCHAAVTNHKKWQYNSPLVPRNAELGDRKGKIHIPFPLANVTCRVPKARNPTVTYG
KNQVIMLLYPDHPTLLSYRNMGEEPNYQEEWVMHKKEVVLTVPTEGLEVTWGNNEPYKYWPQLSTNGT
AHGHPHEIILYYYELYPTMTVVVVSVATFILLSMVGMAAGMCMCARRRCITPYELTPGATVPFLLSLICCIR
TAKA SEQ ID NO: 3
E168K variant of E2 protein from Chikungunya virus
STKIDNFNVYKATRPYLAHCPDCGEGHSCHSPVALERIRNEATDGTLKIQVSLQIGIKTDDSHDWTKLRYM
DNHMPADAERAGLFVRTSAPCTITGTMGHFILARCPKGETLTVGFTDSRKISHSCTHPFHHDPPVIGREKF

SEQUENCES

```
HSRPQHGKELPCSTYVQSTAATTEEIKVHMPPDTPDHTLMSQQSGNVKITVNGQTVRYKCNCGGSNEG
LTTTDKVINNCKVDQCHAAVTNHKKWQYNSPLVPRNAELGDRKGKIHIPFPLANVTCRVPKARNPTVTYG
KNQVIMLLYPDHPTLLSYRNMGEEPNYQEEVMHKKEVVLTVPTEGLEVTWGNNEPYKYWPQLSTNGT
AHGHPHEIILYYYELYPTMTVVVVSVATFILLSMVGMAAGMCMCARRRCITPYELTPGATVPFLLSLICCIR
TAKA

SEQ ID NO: 4
G55R variant of E2 protein from Chikungunya virus
STKDNFNVYKATRPYLAHCPDCGEGHSCHSPVALERIRNEATDGTLKIQVSLQIRIKTDDSHDWTKLRYM
DNHMPADAERAGLFVRTSAPCTITGTMGHFILARCPKGETLTVGFTDSRKISHSCTHPFHHDPPVIGREKF
HSRPQHGKELPCSTYVQSTAATTEEIEVHMPPDTPDHTLMSQQSGNVKITVNGQTVRYKCNCGGSNEG
LTTTDKVINNCKVDQCHAAVTNHKKWQYNSPLVPRNAELGDRKGKIHIPFPLANVTCRVPKARNPTVTYG
KNQVIMLLYPDHPTLLSYRNMGEEPNYQEEVMHKKEVVLTVPTEGLEVTWGNNEPYKYWPQLSTNGT
AHGHPHEIILYYYELYPTMTVVVVSVATFILLSMVGMAAGMCMCARRRCITPYELTPGATVPFLLSLICCIR
TAKA SEQ ID NO: 5
E247K variant of E2 protein from Chikungunya virus
STKIDNFNVYKATRPYLAHCPDCGEGHSCHSPVALERIRNEATDGTLKIQVSLQIGIKTDDSHDWTKLRYM
DNHMPADAERAGLFVRTSAPCTITGTMGHFILARCPKGETLTVGFTDSRKISHSCTHPFHHDPPVIGREKF
HSRPQHGKELPCSTYVQSTAATTEEIEVHMPPDTPDHTLMSQQSGNVKITVNGQTVRYKCNCGGSNEG
LTTTDKVINNCKVDQCHAAVTNHKKWQYNSPLVPRNAKLGDRKGKIHIPFPLANVTCRVPKARNPTVTYG
KNQVIMLLYPDHPTLLSYRNMGEEPNYQEEVMHKKEVVLTVPTEGLEVTWGNNEPYKYWPQLSTNGT
AHGHPHEIILYYYELYPTMTVVVVSVATFILLSMVGMAAGMCMCARRRCITPYELTPGATVPFLLSLICCIR
TAKA SEQ ID NO: 6
G82R variant of E2 protein from Chikungunya virus
STKIDNFNVYKATRPYLAHCPDCGEGHSCHSPVALERIRNEATDGTLKIQVSLQIGIKTDDSHDWTKLRYM
DNHMPADAERARLFVRTSAPCTITGTMGHFILARCPKGETLTVGFTDSRKISHSCTHPFHHDPPVIGREKF
HSRPQHGKELPCSTYVQSTAATTEEIEVHMPPDTPDHTLMSQQSGNVKITVNGQTVRYKCNCGGSNEG
LTTTDKVINNCKVDQCHAAVTNHKKWQYNSPLVPRNAELGDRKGKIHIPFPLANVTCRVPKARNPTVTYG
KNQVIMLLYPDHPTLLSYRNMGEEPNYQEEVVVMHKKEVVLTVPTEGLEVTWGNNEPYKYWPQLSTNGT
AHGHPHEIILYYYELYPTMTVVVVSVATFILLSMVGMAAGMCMCARRRCITPYELTPGATVPFLLSLICCIR
TAKA SEQ ID NO: 7
H232Y variant of E2 protein from Chikungunya virus
STKIDNFNVYKATRPYLAHCPDCGEGHSCHSPVALERIRNEATDGTLKIQVSLQIGIKTDDSHDWTKLRYM
DNHMPADAERAGLFVRTSAPCTITGTMGHFILARCPKGETLTVGFTDSRKISHSCTHPFHHDPPVIGREKF
HSRPQHGKELPCSTYVQSTAATTEEIEVHMPPDTPDHTLMSQQSGNVKITVNGQTVRYKCNCGGSNEG
LTTTDKVINNCKVDQCHAAVTNYKKWQYNSPLVPRNAELGDRKGKIHIPFPLANVTCRVPKARNPTVTYG
KNQVIMLLYPDHPTLLSYRNMGEEPNYQEEVMHKKEVVLTVPTEGLEVTWGNNEPYKYWPQLSTNGT
AHGHPHEIILYYYELYPTMTVVVVSVATFILLSMVGMAAGMCMCARRRCITPYELTPGATVPFLLSLICCIR
TAKA
```

What is claimed is:

1. A lyophilized pharmaceutical unit dosage composition lyophilized from a composition comprising a) an attenuated Chikungunya virus (CHIKV); b) 5% (w/v) sucrose; c) 5 mM potassium phosphate; d) 25 mM sodium citrate; e) 5 mM $MgCl_2$; f) 0.5% (w/v) D-sorbitol; g) 10 mM L-methionine; and h) 0.01% (w/v) recombinant human serum albumin (rHSA), wherein said unit dosage composition comprises $10^3$ to $5 \times 10^4$ $TCID_{50}$/dose, and wherein said attenuated CHIKV comprises an RNA genome corresponding to the DNA sequence as defined by SEQ ID NO: 1 (CHIKV-$\Delta$5nsP3) and/or one or more variants thereof, wherein said variant has a nucleic acid sequence that is at least 99% identical to SEQ ID NO: 1 and has the entire 60 amino acid deletion in nsP3 as in SEQ ID NO: 1.

2. The pharmaceutical composition according to claim 1, wherein said unit dosage comprises $10^3$ to $2 \times 10^4$ $TCID_{50}$/dose.

3. The pharmaceutical composition according to claim 1, wherein said dosage is $5 \times 10^3$ $TCID_{50}$/dose.

4. The pharmaceutical composition according to claim 1, wherein said attenuated CHIKV variant expresses an E2 protein with at least one mutation compared with the wild-type E2 protein as defined by SEQ ID NO: 2.

5. The pharmaceutical composition according to claim 1, wherein said attenuated CHIKV variant expresses an E2 protein with an E168K mutation as defined by SEQ ID NO: 3.

6. The pharmaceutical composition according to claim 1 for use as a one-shot vaccine for the prevention or treatment of CHIKV infection.

7. The pharmaceutical composition according to claim 1, wherein said CHIKV variant expresses an E2 protein as defined by any of SEQ ID Nos: 3-7.

8. The pharmaceutical composition according to claim 1, wherein said composition is able to increase serum antibody titers to said virus in a human by at least 1 log relative to a control within 14 days from primary immunization.

9. The pharmaceutical composition according to claim 1, wherein said composition is able to increase serum antibody titers to said virus in a human by at least 1 log relative to a control within 7 days from primary immunization.

10. The pharmaceutical composition according to claim 1, wherein said composition is able to stimulate seroconversion in at least 25%, at least 30%, at least 40%, at least 50%, at least 60%, at least 70%, at least 80%, at least 90%, at least 91%, 92%, 93%, 94%, 95%, 96%, 97%, 98%, 99%, up to 100% of vaccinated subjects within 7 days of vaccination, wherein seroconversion is defined as reaching a neutralizing CHIKV antibody titer of at least 10.

11. The pharmaceutical composition according to claim 1, wherein said composition is able to stimulate seroconversion in at least 25%, at least 30%, at least 40%, at least 50%, at least 60%, at least 70%, at least 80%, at least 90%, at least 91%, 92%, 93%, 94%, 95%, 96%, 97%, 98%, 99%, up to 100% of vaccinated subjects within 14 days of vaccination, wherein seroconversion is defined as reaching a neutralizing CHIKV antibody titer of at least 10.

12. The pharmaceutical composition according to claim 1, wherein said composition is able to induce a protective immune response which lasts for at least 6 months.

13. The pharmaceutical composition according to claim 1, wherein said composition is able to induce a protective immune response which lasts for at least 12 months.

14. The pharmaceutical composition according to claim 1, wherein said composition is able to induce a protective immune response which lasts for at least 24 months.

15. The pharmaceutical composition according to claim 1, wherein said composition is able to induce a protective immune response which confers life-long protection against CHIKV disease.

16. The pharmaceutical composition according to claim 1, for use in a method of treating or preventing a CHIKV infection.

17. The pharmaceutical composition according to claim 10, wherein seroconversion is defined as reaching a neutralizing CHIKV antibody titer of at least 20.

18. The pharmaceutical composition according to claim 11, wherein seroconversion is defined as reaching a neutralizing CHIKV antibody titer of at least 20.

\*    \*    \*    \*    \*